(12) United States Patent
Li et al.

(10) Patent No.: US 8,754,013 B2
(45) Date of Patent: Jun. 17, 2014

(54) OPEN-READING-FRAME (ORF) PHAGE DISPLAY

(75) Inventors: Wei Li, Miami Beach, FL (US); Xiaoyu Jiang, Miami, FL (US); Nora Blanca Caberoy, Miami, FL (US)

(73) Assignee: University of Miami, Miami, FL (US)

( * ) Notice: Subject to any disclaimer, the term of this patent is extended or adjusted under 35 U.S.C. 154(b) by 509 days.

(21) Appl. No.: 13/062,860

(22) PCT Filed: Jun. 9, 2009

(86) PCT No.: PCT/US2009/046696
§ 371 (c)(1),
(2), (4) Date: Apr. 26, 2011

(87) PCT Pub. No.: WO2010/030425
PCT Pub. Date: Mar. 18, 2010

(65) Prior Publication Data
US 2011/0207628 A1    Aug. 25, 2011

Related U.S. Application Data

(60) Provisional application No. 61/096,015, filed on Sep. 11, 2008.

(51) Int. Cl.
*C40B 30/04* (2006.01)
(52) U.S. Cl.
USPC ............................................................. 506/9
(58) Field of Classification Search
None
See application file for complete search history.

(56) References Cited

U.S. PATENT DOCUMENTS

2005/0255608 A1    11/2005    Bohannon et al.
2006/0068421 A1 *   3/2006    Gray et al. ................... 435/6
2007/0197444 A1     8/2007    Herman et al.

OTHER PUBLICATIONS

Ansuini et al. (Aug. 2002) Nucleic Acids Research vol. 30 article e78 pp. 1 to 10.*
Chen et al. (Aug. 20, 2004) Chemistry and Biology vol. 11 pp. 1081 to 1091.*

* cited by examiner

*Primary Examiner* — Christian Boesen
(74) *Attorney, Agent, or Firm* — Novak Druce Connolly Bove + Quigg LLP

(57) ABSTRACT

A dual display phage system for the identification of protein interaction networks and therapeutic targets.

5 Claims, 33 Drawing Sheets

FIG. 6
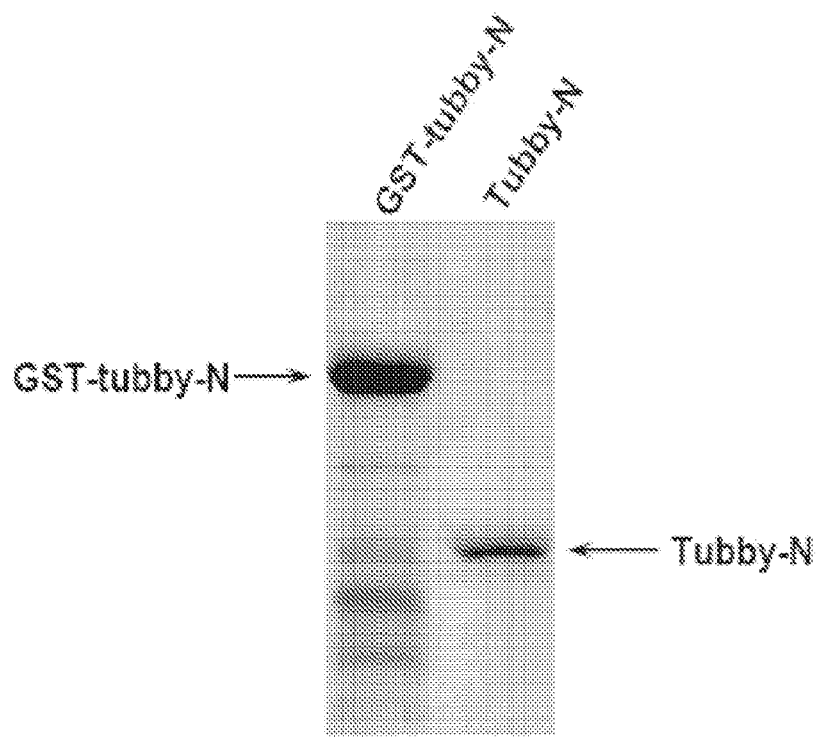
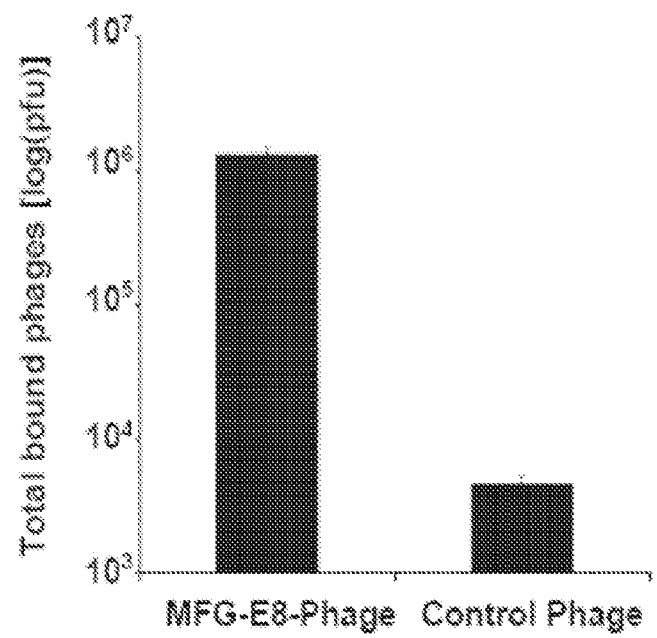
FIG. 7

FIG. 12
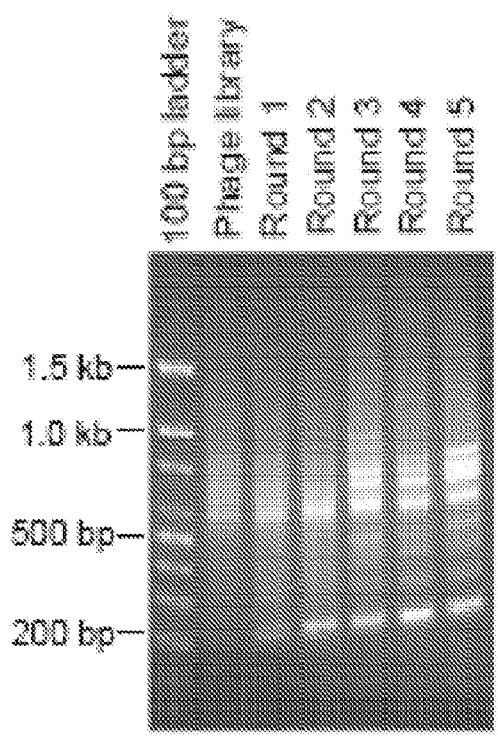
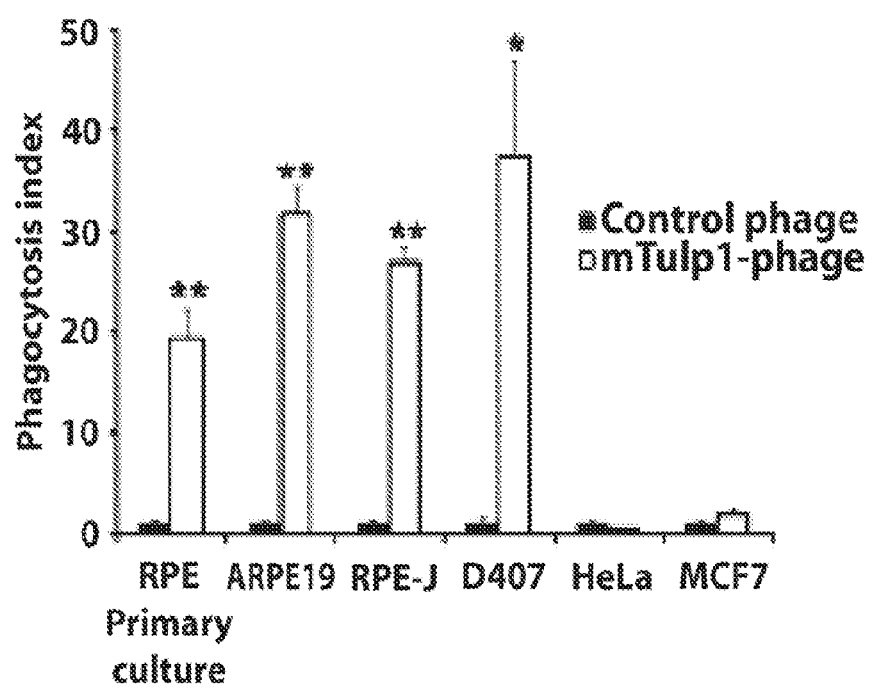
FIG. 13A

Capsid 10B
```
       Val Met Leu Gly Asp Ile Phe Glu Ala Gln Lys Ile Glu Trp His Leu Glu Gly Ser Gly
... GTG ATG CTC GGG GAT CCG CGG CCG CTA TAA GAATTC AACGTT GTCGAG ....
           BamHI  NotI              XhoI                   EcoRI HindIII
```

OPEN-READING-FRAME (ORF) PHAGE DISPLAY

CROSS-REFERENCE TO RELATED APPLICATIONS

The present application claims the priority of U.S. provisional patent application No. 61/096,015 filed Sep. 11, 2008, which is incorporated herein by reference in its entirety.

STATEMENT REGARDING FEDERALLY SPONSORED RESEARCH

This invention was made with U.S. government support under grant number R01EY016211 awarded by the National Institutes of Health/National Eye Institute. The U.S. government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 18, 2011, is named 72301021.txt and is 14,020 bytes in size.

FIELD OF THE INVENTION

Embodiments of this invention relate to an open reading frame phage display system and compositions thereof.

BACKGROUND

Given that proteins regulate almost every biological process, the exploration of protein interaction networks is expected to have major impacts on the understanding of biological systems, disease mechanisms and drug discovery. As a result, development of technologies to identify binding proteins is of major importance in functional proteomics. Yeast two-hybrid system (Y2H) and mass spectrometry coupled with tandem affinity purification (MS-TAP) are two examples. However, these systems are limited by technical complexity, instrument requirements, labor and time commitments. Furthermore, their application is narrowly restricted to bait proteins, but not to other biological molecules.

Since its first description in 1985, phage display has been widely used to identify bait-binding antibodies (Abs) or short peptides from antibody or random peptide libraries. However, phage display with cDNA libraries is rare and inefficient. Although antibody libraries with predictable reading frames can be conveniently fused to the N-terminus of filamentous phage gene III capsid protein (pIII) without reading frame shift, a cDNA library with unpredictable reading frames and stop codons may interfere with pIII expression. To circumvent the problem, various strategies of C-terminal display have been explored. However, C-terminal display cannot ensure that the cDNA library is expressed in the correct reading frames. Unlike Y2H, non-open-reading-frame (non-ORF) phage clones encoding unnatural short peptides tend to outgrow ORF clones through multiple rounds of selection and amplification. Consequently, most of identified phage clones encode out-of-frame unnatural short peptides, rather than real proteins, with minimal implication in protein biological networks. It, thus, remains a daunting challenge for the technology to be applied to functional proteomics with an efficiency comparable to Y2H and MS-TAP.

SUMMARY

This Summary is provided to briefly indicate the nature and substance of the invention. It is submitted with the understanding that it will not be used to interpret or limit the scope or meaning of the claims.

Efficient identification of the physical association of proteins is crucial for elucidation of protein interaction networks and therapeutic targets. The open-reading-frame (ORF) phage display was developed to identify unknown bait-binding proteins in as fast as ~2-7 days. The system comprises major breakthroughs including: high-quality ORF phage display cDNA library, specific phage elution by protease cleavage and dual phage display for sensitive high throughput screening. ORF phage display is a versatile technology capable of identifying proteins binding to immobilized proteins, non-protein molecules or multimolecular baits. The ORF phage display can be fully automated for high throughput screening to delineate biological networks and therapeutic protein targets.

The invention further comprises a system for rapid cloning of full-length open reading frame (ORF) cDNA sequences and other polynucleotides. A phage display vector was engineered, so that when ORF cDNA sequence is inserted into the vector, a C-terminal biotinylation tag or any other tag, is expressed, biotinylated and displayed on phage surface. Conversely, if an out-of-frame cDNA sequence is inserted into the phage vector, no biotin or any other tag that is selected for use in the system, is displayed on phage surface. The surface display of biotin allows for the rapid cloning of full-length ORF cDNA sequences, or any other polynucleotide sequences for individual proteins from tissues.

Compared with commercially available cloning kits or cloning methods, this technology has the following advantages: this procedure takes only a couple of days; high ligation efficiency, guaranteed cloning of full-length ORF cDNA sequences with streptavidin enrichment, and rapid re-verification for ORF cDNA sequences by streptavidin binding assay.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 1A shows the sequence of the T7Bio3C phage display vector (SEQ ID NO: 37). FIG. 1A discloses the protein sequences as SEQ ID NOS 38-39, respectively. FIG. 1B is a schematic representation showing that each engineered phage has 415 copies of capsid 10A and/or 10B, including ~5-15 copies of the ORF cDNA library protein fused to the C-terminus of capsid 10B. A 3C protease cleavage site is located between capsid 10B and the library protein. A. biotinylation tag is expressed at the C-terminus of the library proteins. FIG. 1C is a schematic representation showing that phages bound through the displayed protein can be released by 3C protease cleavage at 4° C.

vs, streptavidin/1% SDS elution; throughout). FIG. 1F is a graph showing elution of non-specifically bound phages by SDS, but not by 3C protease. As an illustration, the phage library was amplified in BLT7Bio bacteria to label capsid 10A with biotin (see FIG. 2A for detail), bound to immobilized streptavidin, washed and eluted with either 1% SDS or 3C protease. FIG. 1G is a graph showing the size distribution of cDNA inserts in the eye library.

FIG. 2E is a scan of a blot showing the verification of Hmgb2-tubby interaction by protein pull-down assay. Cell lysate was prepared from FLAG-Hmgb2-expressing HEK293 cells, incubated with purified glutathione S-transferase (GST) or GST-tubby, followed by glutathione resin. After washing, the resin was analyzed by Western blot using anti-FLAG mAb. FIG. 2F is a scan of a blot showing the verification of phosphatidylserine (PS)-binding proteins. GST-tagged PS-binding proteins and GST control were incubated with PS or PC liposomes. After washing, liposome pellets were analyzed by Western blot using anti-GST mAb.

FIG. 6 is a photograph of a blot showing the purification of GST-free tubby-N. GST-tubby-N was expressed in BL21 (DE3) bacteria and purified using a glutathione column. Purified GST-tubby-N was digested with GST-tagged 3C protease. After dialysis, GST, GST-3C and minor glutathione-binding impurities were depleted with a new glutathione column. Samples were analyzed for their purity by SDS-PAGE. Lane 1, purified GST-tubby-N; Lane 2, GST-free tubby-N.

FIG. 7 is a graph showing that milk fat globule epidermal growth factor 8 (MFG-E8)-phage binds to immobilized PS. PS was coated onto the ELISA plates, blocked and incubated with clonal phage displaying full-length MFG-E8 or control phage with no cDNA insert. After washing, the bound phages were eluted with 3C protease and quantified by plaque assay. Mean±SEM; n=3; *p<0.001; vs. control.

FIG. 10A discloses 'KGVKKK,' 'KGVKAA,' 'KGKGKKK,' 'KGKGKAA,' 'AGAGKKK' and 'AGAGAKK' as SEQ ID NOS 40-45, respectively, in order of appearance.

FIG. 11A is a blot showing the co-immunoprecipitation of Mer with tubby or Tulp1, but not Tulp2, Tulp3 or MPD-null Tulp1. Mer-Fc was incubated with the cell lysates of FLAG-tagged Tulps or MPD-null Tulp1, co-immunoprecipitated with protein G-agarose, analyzed by Western blot using anti-FLAG mAb. FIG. 11B is a blot showing that Mer autophosphorylation induced by membrane vesicles expressing different Tulps during phagocytosis in RPE cells was analyzed by Western blot using anti-phospho-Mer, anti-Mer or anti-RPE65 antibodies. Gas6 was included as a positive control. FIG. 11C is a graph showing that pre-incubation of Mer-Fc with tubby- or Tulp1-membrane vesicles followed by washing blocks vesicle phagocytosis in ARPE19 cells (±SEM; *p<0.001; vs. pcDNA3; throughout). FIG. 11D is a blot showing that Tubby is present in human serum. Serum tubby was enriched by binding to anti-tubby antibody affinity column, eluted, analyzed by Western blot using anti-tubby antibody. A mock column conjugated with pre-immune antibody was included as a negative control. FIG. 11E is a graph showing that extracellular tubby and Tulp1 stimulate RPE phagocytosis. Tubby- or Tulp1-conditioned medium was collected and pre-incubated with control membrane vesicles. After washing, the vesicles were analyzed for RPE phagocytosis and quantified as in FIGS. 8D and E. FIG. 11F is a schematic illustration showing a model of tubby- and Tulp1-mediated synergistic RPE phagocytosis of shed POS. Extracellular tubby and Tulp1 facilitate phagocytosis of shed POS vesicles as bridging molecules by simultaneously associating with shed POS vesicles and binding to Mer RTK on RPE cells. The interaction of tubby and Tulp1 is necessary for synergistic RPE phagocytosis. Mutations in either protein abolish the synergy, leading to autosomal recessive retinal degeneration despite their functional redundancy.

FIG. 12 is a scan of a photograph of a gel showing phage enrichment by phagocytosis selection. The phage library was selected by 5 rounds of phagocytosis in ARPE19 cells as described in Materials and Methods. Phage enrichment at different rounds was analyzed by PCR using T7SelectUp and T7SelectDown primers. The unselected phage library with cDNA inserts in various lengths yielded diffuse PCR products without dominant bands. After selections, several dominant PCR bands emerged at round 3-5, suggesting enrichment of specific phage clones.

FIGS. 13A and 13B show that both tubby and Tulp1 stimulate RPE phagocytosis. FIG. 13A is a graph showing Tulp1-Phage stimulates phagocytosis in RPE cells, but not in non-RPE epithelium cells. Clonal phage expressing full-length mouse Tulp1 (mTulp1) was analyzed for phage internalization in indicated RPE cell lines, RPE primary cells and non-RPE cells. HeLa and MCF7 are human cervix epithelial and mammary gland epithelial cell lines, respectively. Mean±SEM; n=3; *p<0.05, **p<0.001; vs. control phage. FIG. 13B is a graph showing clonal phages expressing Tulp179-199, full-length mouse Tulp1 (mTulp1), human Tulp1 (hTulp1) and mouse tubby (mTubby) facilitates phage uptake in ARPE19 cells. Mean±SEM; n=3; *p<0.001.

FIG. 14A is a scan of a photograph showing phagocytosed microbeads (yellow signals) which were analyzed by confocal microscopy. Nuclei were stained with DAPI (blue signals). FIG. 14B is a graph showing that the relative fluorescence intensity per cells is quantified. Mean±SEM; n>100; *p<0.001; vs. GST.

FIG. 15A: Tubby-Phage and Tulp1-Phage bind to immobilized Mer-Fc. Mer-Fc was directly immobilized on ELISA plates, blocked and incubated with Tubby-Phage, Tulp1-Phage or control phage. After washing, bound phages were eluted by 3C protease cleavage, quantified by plaque assay and expressed as relative binding activity, which is the pfu ratio of (total bound tubby-Phage)/(total bound control phage). Mean±SEM; n=3; *p<0.001; vs. control phage. FIG. 15B: Mer-Fc binds specifically to membrane vesicles expressing tubby or Tulp1, but not Tulp2, Tulp3, MPD-null Tulp1 or pcDNA3 control. Membrane vesicles were prepared from Neuro-2a cells expressing indicated recombinant Tulps, immobilized on ELISA plates, blocked and incubated with Mer-Fc. After washing, bound Mer-Fc was detected with biotin-conjugated goat anti-human antibody, followed by streptavidin-labeled HRP and colorimetric assay. Mean±SEM; n=3; *p<0.001; vs. pcDNA3.

FIG. 19A discloses the amino acid sequences as SEQ ID NOS 47-48, respectively. This vector had an in-frame stop codon between NotI and XhoI sites to prevent the expression of the biotinylation tag in T7Bio phage without cDNA insert.

FIG. 20A: The expression of Gas6 and MFG-E8 on phage surface is verified by the detection of C-terminal biotin displayed on both Gas6-phage and MFG-E8-phage. Control T7Bio phage had an internal stop codon to prevent the expression of C-terminal biotinylation tag. All phages were analyzed for their binding activity to immobilized streptavidin. Bound phages were quantified by plaque assay (±s.d., *p<0.001, vs. T7Bio phage, n=5).

(FIG. 24C) Phage lysates at each round were analyzed with gene-specific primers to detect Gas6-phage and MFG-E8 phage.

DETAILED DESCRIPTION

Figure 1A:
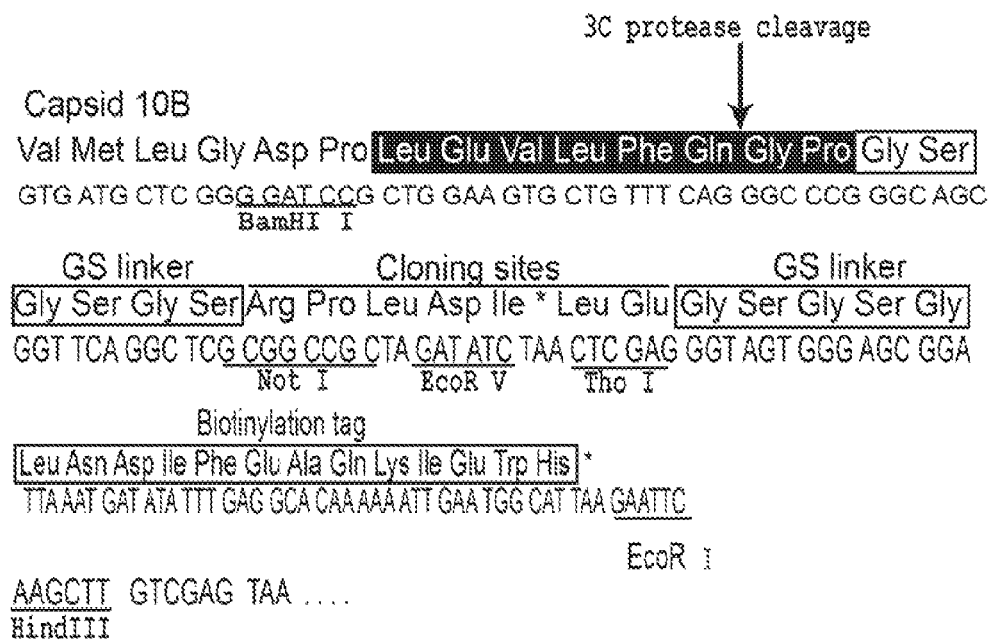
FIGS. 1A-1C show the ORF phage display cDNA libraries.
Figure 1B:
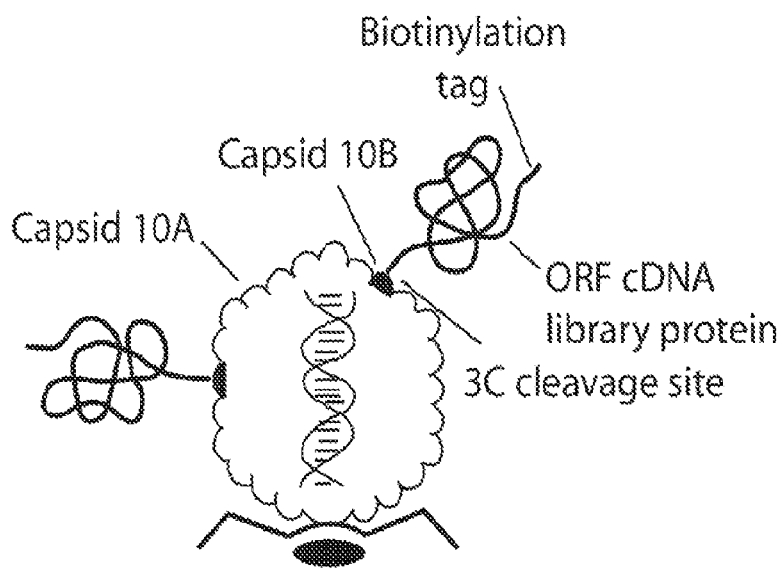
Figure 1C:
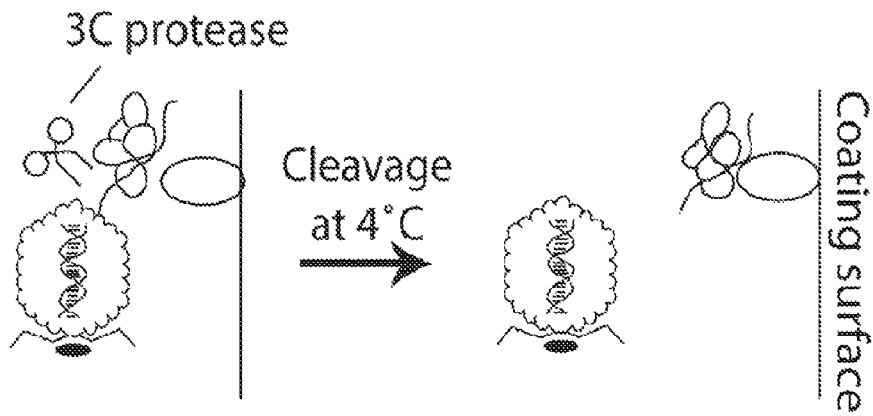
Figure 1D:
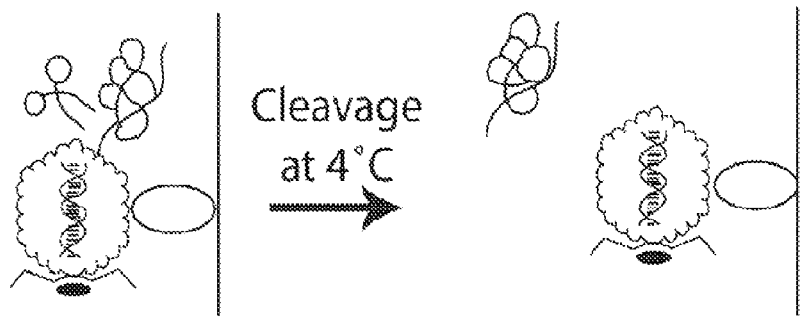
FIG. 1D is a schematic representation illustrating that phages bound through other surface proteins cannot be eluted by 3C protease.
Figure 1E:
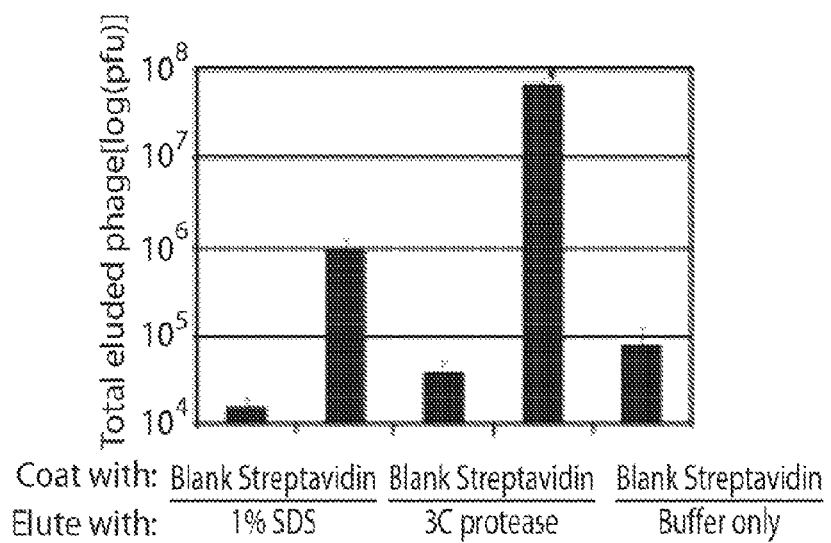
FIG. 1E is a graph showing specific elution by 3C protease. ORF phage display library bound to immobilized streptavidin through the biotin tag at the C-terminus of the library protein, washed and eluted with 1% SDS or 3C protease. (±SEM; n=3; *p<0.001.

Embodiments of the invention comprise an open reading frame phage display and compositions thereof. In particular, the invention comprises a phage display vector having a tag tethered to the vector. PCR products of full-length protein coding sequences without a stop codon can be digested with proper restriction enzymes and ligated into the phage vector, so that the tag is expressed at the C-terminus of the proteins and displayed on phage surface. The phage system has a much higher ligation and packaging efficiency than plasmid ligation and often yields 10,000 to 10,000,000 phage plaques. Among these plaques some may have no cDNA insert, whereas others may have out-of-frame or ORF cDNA inserts. Only those phage clones with ORF cDNA insert express biotin tag and can be further enriched by a binding procedure with, for example, immobilized streptavidin on a 96-well plate. The streptavidin bound phages can be eluted by proteases or typical elutors such as for example, 0.1% SDS solution. Individual streptavidin-enriched phage plaques on bacterial plates can be screened by PCR for cDNA insert with one primer annealing to the phage vector and the other primer annealing to the cDNA insert. Most of the positive clones have full-length ORF cDNA insert due to the streptavidin enrichment. The enrichment procedure may be repeated.

DEFINITIONS

Prior to describing the invention in greater detail the following definitions are set forth to illustrate and define the meaning and scope of the terms used to describe the invention herein:

As used herein, the singular forms "a," "an," and "the" include plural referents unless the context clearly dictates otherwise.

As used herein, a "tag" refers to a moiety that is inserted in the C-terminal end of the nucleic acid sequences so that the tag is displayed on the phage surface. The tag is encoded and displayed on the phage surface only when an in-frame open reading frame nucleic acid sequence is expressed by the vector. The phage vectors comprising the ORF are enriched by binding to a capture element. The tag specifically binds to a capture element or binding partner as a result of attractive forces that exist between the tag and the capture element. "Specifically binds" as it refers to a "tag" and a capture element means via covalent or hydrogen bonding or electrostatic attraction or via an interaction between, for example a protein and a ligand, an antibody and an antigen, protein subunits, or a nucleic acid binding protein and a nucleic acid binding site. A tag does not interfere with the ability of a probe to anneal to a target nucleic acid. Tags include but are not limited to biotin, streptavidin, avidin, an antibody, an antigen, a hapten, a protein, a peptide epitope, or a chemically reactive moiety. A "tag" as defined herein can bind to a "capture element" as defined herein. According to the invention, a "tag" and a "capture element" function as a binding pair. For example, in one embodiment, if a tag is biotin, the corresponding capture element is streptavidin. Alternatively, in another embodiment, if a tag is an antibody, the corresponding capture element is an antigen. Or if a tag is an antigenic peptide epitope, the corresponding capture elements is an cognate antibody.

A "binding pair" or "binding partners" refer to a first and second moiety that specifically bind to each other. Exemplary binding pairs include, but are not limited to, biotin and either streptavidin, avidin or neutravidin; a hapten and an antibody thereto; and an enzyme and an inhibitor.

Although biotin/streptavidin is a preferred binding pair, other binding pairs can be used for recovery of samples and are known in the art. Other examples of binding pairs include, but are not limited to, antigen/antibody, sugar/lectin, apoenzyme/cofactor, hormone/receptor, enzyme/inhibitor, and complementary homopolymeric oligonucleotides. Examples of solid supports to which second members of the binding pairs can be attached include, but are not limited to, plastic, magnetic beads, glass beads, filter membranes, filter papers and polymeric beads.

As used herein, "target nucleic acid" or "template nucleic acid sequence" refers to a region of a nucleic acid, for example, a full length open reading frame, that is to be either replicated, amplified, and/or detected.

Open Reading Frame (ORF) Phage Display

Phage display is a technology to identify proteins with specific binding activity. FIGS. 1A to 1E show a schematic representation of an embodiment showing some general steps in phage selection. In phage display, foreign cDNA is genetically fused to a phage coat (capsid) protein in phage genome, so that library proteins are expressed as coat (capsid) fusion proteins and displayed on phage surface. Each phage clone displays multiple copies of the same protein. Two unique features of phage display, the physical linkage of a polypeptide's phenotype to its corresponding genotype and the rescue of bait-binding phages, enable enrichment of phages with specific bait-binding activity through multiple rounds of selection. Enrichment substantially improves the efficiency of identifying unknown binding polypeptides. Briefly, the steps of the ORF phage display are as follows: Purified bait is immobilized, for example, on 96-well ELISA plates (or microbeads), blocked, and incubated with phage display library. After washing, bound phages are eluted. A small aliquot of eluted phages are used for phage quantification by plaque assay. The remaining eluted phages are amplified in host bacteria and used as input for the next round of selection. After multiple rounds of selection, bait-binding phages are enriched and can be individually characterized for their bait-binding activity.

Any phage can be used in the methods described herein and embodiments of the invention are not limited to one type of phage, for example, filamentous phage display, lambda phage display. In one embodiment, the phage is T-phage. T-phage are a series of 7 virulent phages which infect *E. coli*. The T-even phages T2, T4; (bacteriophage T4), and T6, and the phage T5 are called "autonomously virulent" because they cause cessation of all bacterial metabolism on infection. Phages T1, T3; (bacteriophage T3), and T7; (bacteriophage T7) are called "dependent virulent" because they depend on continued bacterial metabolism during the lytic cycle. The T-even phages contain 5-hydroxymethylcytosine in place of ordinary cytosine in their DNA.

In another preferred embodiment, the phage is a T7 phage. Unlike the filamentous systems, peptides or proteins displayed on the surface of T7 phage do not need to be capable of secretion through the cell membrane, a necessary step in filamentous phage assembly. Lambda phage display has similar properties to T7 phage display. T7 phage is very easy to grow and replicates much more rapidly than either lambda (λ) phage or filamentous phage, decreasing the time needed to perform multiple rounds of growth for phage selection. T7 phage particle is extremely robust, and is stable to harsh condition. More importantly, C-terminal display of T7 phage is advantageous for cDNA library with unpredictable reading frames. On the other hand, bait-bound filamentous phages in 96-well plates can be easily quantified by ELISA using HRP (horseradish peroxidase)-conjugated phage-specific Abs. Due to lack of phage-specific antibodies, T7 phage quantification has to be determined by tedious phage plaque assay, substantially limiting T7 phage application with high throughput screening by pharmaceutical and biotech industries. As a result, filamentous phage display is far more widely adapted by academic and industrial users than T7 phage display.

Phage display has been extensively used to identify antigen (Ag)-specific antibodies [Fab or single chain fragment variable (scFv)] from antibody libraries or short peptides from random peptide libraries. However, its successful application of identifying endogenous proteins from cDNA libraries is rare and inefficient, because the majority of identified bait-binding clones encode out-of-frame unnatural short peptides (i.e. non-ORFS or defective inserts). The results are unpredictable reading frames and stop codons in the cDNA repertoires fused to the N-terminus of filamentous phage gene III coat protein (pIII). Random peptide libraries encoding only 7-12 amino acids (aa) have minimal concern in the reading frame.

However, N-terminal fusion of cDNA library with stop codons may interfere with pIII expression. To circumvent the problem, various display strategies with C-terminal cDNA fusion libraries were explored, including C-terminal pVI display in a filamentous phage. In pJuFo vector, cDNA library was fused to the C-terminus of Fos that was displayed on phage surface by forming a heterodimer with Jun-pIII fusion protein. Moreover, T7 phage display vectors were engineered with cDNA library fused to the C-terminus of phage capsid 10B protein. Although C-terminal display does not interfere with phage coat protein expression, it cannot ensure that the cDNA library inserts are expressed in correct reading frames. Thus, the issue of unpredictable reading frames of cDNA fusion libraries remains with C-terminal display strategy. For example, only less than 10% of sequenced clones (24 out of 243) identified from T7 phage display cDNA library were ORFs. Although automated robot technology for high throughput screening has been proposed and may help identify a few more ORFs out of large number of non-ORFs, the charm of phage display with enrichment for enhanced cloning efficiency over regular cDNA cloning strategies is lost. Thus, despite tenacious efforts and sporadic reports of identifying a few endogenous binding proteins with ORFs over the past 25 years, cDNA phage display is in general inefficient and unsuccessful.

ORF Library Generation:

ORF cDNA libraries were generated based on the fact that non-ORF cDNA has many stop codons, whereas ORF has none. An analysis of GenBank databases showed that 96% of 200-bp non-ORF cDNAs have at least one stop codon. This number drastically increases to 99.2% for non-ORF cDNAs with 300 bp. Several ORF phage display cDNA libraries were recently constructed according to this principle. However, only one ORF library has been characterized for its cDNA inserts with merely 43% of the inserts longer than 300 bp. Consequently, no study has demonstrated a reasonable percentage of ORFs among total sequenced clones for cDNA phage display.

Embodiments of the Open Reading Frame (ORF) phage display system comprise: a) a uniquely engineered phage display vector for specific phage elution by protease cleavage, b) high-quality ORF phage display cDNA library, c) effective blocking reagents to minimize non-specific phage enrichment, and d) dual phage display for sensitive high throughput screening.

General examples include any protease comprising, for example: serine proteases, threonine proteases, cysteine proteases, aspartate proteases, metalloproteases, glutamic acid proteases. Examples of further proteases and their cleavage sites comprise: TEV protease and its site; thrombin and its cleavage site; enterokinase and enterokinase cleavage site, Factor Xa and its cleavage site, and the like. The enzyme cleavage sites are not limited proteases but includes any type of enzyme-cleavage site.

Design and Engineering of Phage Vector for Specific Phage Elution:

An example of the engineering of the phage vector is described in detail in the examples section which follows. The example is not to be construed as a limitation to the instant invention but to provide an understanding of the compositions and methods described in various embodiments.

Briefly, to optimize T7 phage display, T7Select10-3b (Novagen) was engineered to generate T7bio3C and T7his3C vectors. A cleavage site for human rhinovirus (HRV) 3C protease was followed by GS linker, NotI, EcoRV, stop codon, XhoI, GS linker, biotinylation tag (or polyhistidine tag for T7his3C vector) and stop codon. A cDNA library was inserted at NotI and XhoI sites, both of which have low frequency in the human genome. The internal stop codon was to prevent the expression of downstream biotinylation tag in the empty vector without a cDNA insert. The biotinylation tag (or polyhistidine tag) was expressed only if the cDNA insert was an ORF. Thus, ORF phage clones, but not non-ORF phages, were spontaneously biotinylated by E. coli BirA ligase and enriched by binding to immobilized streptavidin (or anti-polyhistidine mAb or $Ni^{2+}$ or $Co^{2+}$ resin) to yield ORF library. The EcoRV site was to minimize the possible self-ligation of the vector by co-digestion with NotI, EcoRV and XhoI. The 3C protease cleavage at 4° C. specifically eluted the phages bound to immobilized bait through the library proteins, but not through other phage surface proteins. Two flexible GS linkers were designed to improve the accessibility of the 3C cleavage site, library proteins and biotin tag. Cleavage with 3C protease eluted more bound phages than standard elution by 1% SDS, indicating that the protease cleavage site was fully accessible in the library. Furthermore, non-specifically bound phages were not eluted by 3C cleavage.

Size-Defined, C-Terminal Tagged ORF Phage Display cDNA Libraries.

An illustrative example, which is not meant to be construed or limit the invention in any way is as follows. Two high-quality ORF libraries were generated: one from mouse eyes and the other from mouse E18 embryos. Briefly, total RNA was extracted from the tissues, and mRNA was purified using an mRNA extraction kit (Qiagen). Orientation-directed double-stranded cDNA was generated using tagged random primers. cDNA fragments between about 300 bp and 2 kb were purified from agarose gel, digested with NotI and XhoI, ligated into T7bio3C vectors at NotI and XhoI sites, and packaged into T7 phage using T7 phage packaging extract. The titer of the packaged cDNA libraries was quantified by plaque assay to determine the initial library diversity. Total packaged phage titers were $2\times10^7$ p.f.u for the eye library and $1\times10^8$ p.f.u for the embryo library, sufficient diversities to cover each of ~25,000 mouse genes up to 4,000 times. Both libraries were amplified once, bound to immobilized streptavidin and eluted by 3C cleavage to generate ORF libraries. To characterize the qualities of the ORF libraries, $10^5$ phage clones were randomly picked from the libraries and analyzed the size distribution of their cDNA inserts by PCR. The results showed that more than 75% of the library inserts had cDNA inserts longer than 300 bp. Furthermore, immunoblot analysis revealed that more than 90% of the streptavidin-enriched ORF library expressed biotin tag.

The quality of the ORF libraries were defined by two parameters: the initial diversity of the libraries and the size distribution of the cDNA inserts. Generating high-quality, size-defined ORF phage display cDNA library with minimal amount of small inserts (<300 bp) has been, heretofore, technically challenging. There is only one characterized ORF N-terminal display library with >57% of the cDNA inserts smaller than 300 bp.

Effective Blocking Reagents.

Multiple rounds of phage selection often lead to substantial increase in total bound phages, but not specificity (i.e. bait vs. blank). Most phage selection schemes use the same blocking reagents [bovine serum albumin (BSA) or dry milk] to reduce non-specific phage binding to ELISA plates. It was observed that phage selection also enriched BSA-binding phages, which may be responsible for minimal specificity for some baits. Dependent on the nature of baits and their concentration for immobilization, BSA often failed to block the unoccupied non-specific sites completely. In order to overcome such problems, more than two dozen of putative blocking reagents were tested with polyvinylpyrrolidone (PVA) as the best blocking reagent for ORF phage display with either protein baits or non-protein baits. Blocking with PVA is most likely to result in maximal bait-specific phage enrichment with no detectable PVA-binding phages. It would also be applied to antibody phage display and random peptide display with filamentous phage display systems.

In a preferred embodiment, any blocker or combinations of blockers can be used as long as the blocker increases specific phage enrichment and efficiency of ORF phage display, preferably with minimal binding protein and low affinity.

In a preferred embodiment, the invention provides a new blocking reagent of PVA to maximize specific phage enrichment for any difficult bait.

Dual Phage Display for High Throughput Screening.

A major rate-limiting step in phage display has, heretofore, been to quantify eluted phages by plaque assay. The tedious procedure of plaque assay includes serial dilution of phages, infecting the host cells, plating, culturing and plaque counting.

In one preferred embodiment, a dual phage display is provided, and bound phages are measured by a machine readable and quantifiable format. An example would be, an ELISA-like colorimetric assay. An illustrative example, which is not meant to be construed or limit the invention in any way is as follows. For binding analysis of individual T7 phage clones, T7 phages were amplified in a host cells expressing capsid 10A protein with a C-terminal tag. In the examples section which follows, E. coli BLT7FLAG and BLT7Bio strains were developed which expressed 10A with C-terminal FLAG tag and biotinylation tag, respectively. Phages amplified in BLT7FLAG bacteria displayed not only 5-15 copies of biotinylated 10B-library fusion protein, but also more than 400 copies of 10A-FLAG on its surface which was sensitively detected by anti-FLAG mAb, followed by HRP-conjugated goat anti-mouse IgG and colorimetric assay. The colorimetric assay had sensitivity similar to plaque assay.

In another preferred embodiment, methods of determining whether a specific bait-binding clone has ORF cDNA insert or not, are provided. For example, a phage clone expressing tubby-N-binding protein is amplified in BLT7FLAG bacteria and is capable of binding to immobilized tubby-N. Bound ORF phages were sensitively detected with anti-FLAG mAb. If necessary, the phage clones in 96-well plates may be replicated with a 96-well plate replicator, re-amplified in BLT5615, BLT7FLAG or BLT7Bio bacteria in new 96-well plates to conveniently switch their surface tag labeling for different detection methods.

The dual phage display technology converts the cumbersome phage plaque assay into a convenient colorimetric assay. This conversion is pivotal for high throughput screening of large number of individual phage clones for T7 phage display system and allows the ORF phage display to be fully automated for the elucidation of biological networks and drug discovery in an industrial scale.

ORF Phage Display Technology.

The ORF phage display systems described herein are efficient, convenient, versatile and can identify unknown bait-binding proteins in less than 7 days. An embodiment of the methods comprises the following steps. Multiple rounds (usually 3-5 rounds) of phage selection are performed with immobilized baits in ELISA plates, followed by one round of selection with immobilized streptavidin to enrich phages with ORFs. Individual clones are randomly picked from the plates of enriched phages, amplified in BLT7FLAG bacteria, and analyzed for their bait-specific binding activities by high throughput screening with colorimetric assay in ELISA plates using anti-FLAG monoclonal antibody. cDNAs of positive clones are amplified by PCR and identified by sequencing.

Some Features of ORF Phage Display.

The technology is efficient because it can rapidly screen unknown bait-binding proteins from >$10^{10}$ p.f.u library in less than 7 days, whereas it is labor-intensive and time consuming for Y2H to screen only $10^6$-$10^7$ library clones. ORF phage display is sensitive enough to detect and identify single copy of rare phage clone, whereas MS-based functional proteomics can only detect binding proteins at subfemtomole level (i.e. at least $10^8$ molecules). Embodiments of the technology described herein, are convenient because the entire functional cloning method is an ELISA-like procedure. Thus, it can be fully automated for high throughput screening to elucidate biological pathways and for drug discovery. On the other hand, individual laboratories with minimal experience in bacterial culture, ELISA assay and PCR can perform ORF phage display as well. The technology is versatile because it can identify not only protein-protein interactions (PPIs), but also protein interactions with non-protein molecules, whole cells or even tissues and organs in in vitro or in vivo settings.

Versatile Applications of ORF Phage Display:

ORF phage display is a versatile tool for functional proteomics (i.e. to study protein function globally) and drug discovery.

In a preferred embodiment, the ORF phage display screens for proteins with a cDNA library.

In another preferred embodiment, the ORF phage display screens for proteins binding to antibodies, peptides, organic molecules, inorganic molecules, organisms, and the like.

Protein-Protein Interactions (PPIs):

Given that protein regulates nearly every biological process, the exploration of global and pathway-specific protein interaction networks is expected to have major implications in the understanding of disease mechanisms and for drug discovery. Consequently, development of technologies that address physical associations of proteins, either with other proteins or with non-protein molecules, is of major importance in functional proteomics (or functional genomics). Y2H, MS-based approach, surface plasmon resonance spectroscopy, NMR and fluorescence-based technologies are a few examples. However, these systems are limited by technical complexity, instrument requirement, enormous labor and time commitment. Furthermore, their application is narrowly restricted to PPIs, but not protein interactions with non-protein molecules, virus, cells or tissues.

Protein-"Non-Protein Molecule" Interactions (PNIs):

Non-protein molecules, such as lipids, polysaccharides, antibodies, RNA, DNA, can also be used as bait molecules directly or indirectly immobilized on ELISA plates for ORF phage display. Y2H and MS-based functional proteomics cannot be used to study PNIs. In contrast, as long as a non-protein bait molecule can be immobilized either directly or indirectly, it can be used for ORF phage display. For example, biotinylated DNA or RNA may be indirectly immobilized through coated streptavidin. Other non-protein molecules, such as carbohydrates or glycosylated biomolecules, may be covalently immobilized on 96-well plates or microbeads.

Protein-Antibody Interaction (PAIs):

Disease-specific antibodies (Abs) in patient blood, such as tumor-specific antibodies or autoreactive antibodies in autoimmune diseases, are important probes for non-invasive disease profiling and diagnosis. These antibodies can be immobilized on ELISA plates or microbeads to identify Ab-specific proteins or antigens by ORF phage display. Identified proteins or antigens can be used as disease biomarkers to detect the cognate antibody in patient serum for disease diagnosis.

Protein-Virus Interactions (PVIs):

Virus interaction with host cell surface receptors is critical for virus entrance and drug discovery. ORF phage display will be a valuable tool to identify endogenous proteins with binding activity to viral envelope. This will accelerate the identification of virus receptors and the development of anti-viral drugs by blocking viral entrance. Purified viruses may be directly immobilized on ELISA plates and used as baits to identify viral receptors by ORF phage display.

Protein-Cell Interaction (PCIs).

ORF phage display can identify endogenous molecules specifically binding to different cell surface. This will help drug development for cancer therapy and identification of possible surrogate biomarkers for stem cells, differentiated cells, etc. ORF phage display can also be used to identify endogenous eat-me signals in professional phagocytes, as described in the examples section which follows.

Protein-Tissue Interaction (PTIs):

Previous studies have demonstrated that phage display is a powerful tool to identify peptides and scFvs with binding activity to tumor neovascular vessels in animals. In the in vivo selection, intravenously-administered phage library circulated in the blood and bound to tumor neovascular vessels. Bound phages were recovered from the tumor tissues, amplified in host bacteria and reselected for multiple rounds to enrich phage clones capable of binding to the endothelium of tumor neovascular vessels. Identified scFvs with specific binding activity to tumor neovascular vessels are valuable for guided cancer therapy. ORF phage display can be used to identify endogenous proteins with binding activity to various tissues or organs in in vitro or in vivo settings. These identified proteins not only will elucidate biological networks in different tissues, but also may be used for targeted therapy or as surrogate biomarkers for diagnosis.

Protein-Enzyme Interaction (PEIs).

The importance of proteases has been illustrated not only by the fact that an estimated 2% of human genome encodes for proteases, but also by their roles in a variety of biological processes. For example, angiotensin-converting enzyme (ACE) catalyses the conversion of angiotensin I to angiotensin II, a potent vasoconstrictor. ACE inhibitors have been developed to treat hypertension. Thus far, only a small fraction of these enzymes has been well-characterized for their functions. The formidable challenge in protease biology has been how to elucidate protease-regulated pathways by identifying protease-specific substrates. Phage display with random peptide libraries has been used to identify unnatural short peptides, which has minimal biological implications and cannot help elucidate the biological pathways for the protease. However, ORF phage display can identify real proteins as substrates for a specific protease with biological implications. Identified substrates will help define the pathways that are regulated by the protease.

In a preferred embodiment, a method of cloning a full length open reading frame nucleic acid sequences comprises isolating total RNA from a biological sample, reverse transcribing the target nucleic acid sequence of interest using oligoT priming method and amplifying the resulting cDNA of the target nucleic acid sequence using specific primers. The primers can be specific for different regions of the target nucleic acid sequence; however, the downstream primer does not contain a C-terminal stop codon. The reverse transcriptase polymerase chain reaction (RT-PCR) product is purified digested with appropriate enzymes and ligated into a vector, preferably the vector is a phage vector, and packaged into the phage. See the examples which follow for specific methodologies. The packaged phages are amplified in host bacteria (such as BLT5615) The amplified phages are preferably screened by binding to immobilized streptavidin (a capture element) to identify the phage clones containing the desired open reading frame nucleic acid sequence. Screening can be accomplished in many different ways known to those of ordinary skill in the art, for example, use of a sequence specific probe.

Detectable Tags:

In a preferred embodiment, the phage vector encodes a tag molecule which is displayed on the surface of the phage when the full length open reading frame is inserted in-frame.

In another preferred embodiment, the tag molecule is at the C-terminal end of the nucleic acid sequences.

In another preferred embodiment, the tag molecule comprises a biotinylated tag encoded on the C-terminal ends of proteins. Other examples of tags include, but not limited to a poly histidine tag e.g. His6X (SEQ ID NO: 1), His8x (SEQ ID NO: 51) etc, influenza HA tag, Herpes Simplex virus glycoprotein D (gD) tag, c-myc tag, FLAG tags, and Strep-tag. Non-limiting examples of the peptide sequences of some tag polypeptides are shown in Table 1. This list is by no means exhaustive and is not to be construed as limiting but is merely set forth to provide some examples of tag molecules.

TABLE 1

| Tag | Sequence |
|-----|----------|
| HIS | HHHHHH (SEQ ID NO: 1) |
| c-MYC | EQKLISEEDL (SEQ ID NO: 2) |
| HA | YPYDVPDYA (SEQ ID NO: 3) |
| VSV-G | YTDIEMNRLGK (SEQ ID NO: 4) |
| HSV | QPELAPEDPED (SEQ ID NO: 5) |
| V5 | GKPIPNPLLGLDST (SEQ ID NO: 6) |
| FLAG | DYKDDDDK (SEQ ID NO: 7) |

In another preferred embodiment, the invention provides for the binding partners of each respective tag. For example, in the case of a biotin tag, the binding partner would be streptavidin, avidin or neutravidin. Thus, the binding partners or capture elements are useful, inter alia, in the purification and enrichment of phage displaying the tag on their surface. As discussed, only phage expressing a full length, in-frame, open reading frame nucleic acid sequence display the tag on the surface.

A variety of peptide tags with different functions and affinities can be used in the invention to facilitate the purification and enrichment of phage. A variety of peptide tag known in the art may be used, such as but not limited to the immunoglobulin constant regions, polyhistidine sequence (Petty, 1996, Metal-chelate affinity chromatography, in Current Protocols in Molecular Biology, Vol. 2, Ed. Ausubel et al., Greene Publish. Assoc. & Wiley Interscience), glutathione S-transferase (GST; Smith, 1993, Methods Mol. Cell Bio. 4:220-229), the $E.\ coli$ maltose binding protein (Guar et al., 1987, Gene 67:21-30), and various cellulose binding domains (U.S. Pat. Nos. 5,496,934; 5,202,247; 5,137,819; Tomme et al., 1994, Protein Eng. 7:117-123), protein A, protein G, calmodulin binding peptide (CBP) etc. Other peptide tags are recognized by specific binding partners and thus facilitate isolation by affinity binding to the binding partner, which is preferably immobilized and/or on a solid support. As will be appreciated by those skilled in the art, many methods can be used to obtain the coding region of the above-mentioned peptide tags, including but not limited to, DNA cloning, DNA amplification, and synthetic methods. Some of the peptide tags and reagents for their detection and isolation are available commercially.

In examples where a peptide tag is a non-variable portion of the immunoglobulin molecule, such portions comprise at least a functionally $CH_2$ and $CH_3$ domains of the constant region of an immunoglobulin heavy chain. Fusions are also made using the carboxyl terminus of the Fc portion of a constant domain, or a region immediately amino-terminal to the $CH_1$ of the heavy or light chain. Suitable immunoglobulin-based peptide tag may be obtained from IgG-1, -2, -3, or -4 subtypes, IgA, IgE, IgD, or IgM, but preferably IgG1. Many DNA encoding immunoglobulin light or heavy chain constant regions is known or readily available from cDNA libraries. See, for example, Adams et al., *Biochemistry*, 1980, 19:2711-2719; Gough et al., 1980, *Biochemistry*, 19:2702-2710; Dolby et al., 1980, *Proc. Natl. Acad. Sci. U.S.A.*, 77:6027-6031; Rice et al., 1982, *Proc. Natl. Acad. Sci. U.S.A.*, 79:7862-7865; Falkner et al., 1982, *Nature*, 298:286-288; and Morrison et al., 1984, *Ann. Rev. Immunol*, 2:239-256. Because many immunological reagents and labeling systems are available for the detection of immunoglobulins, the phage can readily be detected and quantified by a variety of immunological techniques known in the art, such as the use of enzyme-linked immunosorbent assay (ELISA), immunoprecipitation, fluorescence activated cell sorting (FACS), etc. Similarly, if the peptide tag is an epitope with readily available antibodies, such reagents can be used with the techniques mentioned above to detect, quantitate, and isolate phage expressing the peptide tag. In many instances, there is no need to develop specific antibodies to the expressed tag.

DNA sequences encoding desired peptide tag which are known or readily available from libraries or commercial suppliers are suitable in the practice of this invention.

Described below are several methods based on specific molecular interactions of a tag and its binding partner.

A method that is generally applicable to purifying phage expressing the constant regions of immunoglobulin is protein A affinity chromatography, a technique that is well known in the art. *Staphylococcus* protein A is a 42 kD polypeptide that binds specifically to a region located between the second and third constant regions of heavy chain immunoglobulins. Because of the Fc domains of different classes, subclasses and species of immunoglobulins, affinity of protein A for human Fc regions is strong, but may vary with other species. Subclasses that are less preferred include human IgG-3, and most rat subclasses. For certain subclasses, protein G (of Streptococci) may be used in place of protein A in the purification. Protein-A sepharose (Pharmacia or Biorad) is a commonly used solid phase for affinity purification of antibodies, and can be used essentially in the same manner for the purification of the phage.

Alternatively, a polyhistidine tag may be used, in which case, the phage can be purified by metal chelate chromatography. The polyhistidine tag, usually a sequence of six histidines, (SEQ ID NO: 1), has a high affinity for divalent metal ions, such as nickel ions ($Ni^{2+}$), which can be immobilized on a solid phase, such as nitrilotriacetic acid-matrices. Polyhistidine has a well characterized affinity for $Ni^{2+}$-NTA-agarose, and can be eluted with either of two mild treatments: imidazole (0.1-0.2 M) will effectively compete with the resin for binding sites; or lowering the just below 6.0 will protonate the histidine side chains and disrupt the binding. Antibodies that recognize the polyhistidine tag are also available. Polyhistidine can also bind to immobilized anti-polyhistidine antibody, which is commercially available.

Another exemplary peptide tag that can be used is the glutathione-S-transferase (GST) sequence, originally cloned from the helminth, *Schistosoma japonicum*.

Another useful peptide tag that can be used is the maltose binding protein (MBP) of *E. coli*, which is encoded by the malE gene. The MBP binds to amylose resin and can be eluted from the amylose resin by maltose. See, for example, Guan et al., 1987, *Gene* 67:21-30.

The second approach for purifying phage expressing the tag on their surface is applicable to peptide tags that contain an epitope for which polyclonal or monoclonal antibodies are available. Various methods known in the art for purification of protein by immunospecific binding, such as immunoaffinity chromatography, and immunoprecipitation, can be used. See, for example, Chapter 13 in Antibodies A Laboratory Manual, edited by Harlow and Lane, Cold Spring Harbor laboratory, 1988; and Chapter 8, Sections I and II, in Current Protocols in Immunology, ed. by Coligan et al., John Wiley, 1991; the disclosure of which are both incorporated by reference herein.

In another preferred embodiment, the phage is a T7 phage. However, the invention is not limited to one type of phage. Other phages include but not limited to icosahedral phage; the term icosahedral phage can include phage having spherical or pseudo spherical shapes. Specific examples of icosahedral phage include the T odd (e.g., T3, T5 and T7 phage) and T even phage (e.g., T 4 and T6). Examples of spherical and pseudo spherical phage include phix174, ms2, m1 and P2 and P4. Viruses having roughly spherical shapes can also be utilized such as SV40, for example. However, while icosahedral phages are preferred, filamentous phage (e.g., M13, fd and fl) and phagemid vectors derived therefrom can also be utilized. For a discussion of filamentous phage see, e.g., Dower, WO 91/19818; Devlin, WO 91/18989; MacCafferty, WO 92/01047; Huse, WO 92/06204; Kang, WO 92/18619.

In another preferred embodiment, the phage vector comprises a linker sequence having restriction endonuclease sites and a tag epitope such as biotin.

In another preferred embodiment, the invention provides for a cloning system. The system includes a phage vector comprising a linker sequence and a C-terminal tag. A preferred linker comprises SEQ ID NO: 10. The tag is displayed on the surface of the phage when an in-frame open reading frame nucleic acid sequence is cloned into the phage vector. Positive clones are enriched by use of assays such as binding assays, whereby the binding partner or capture element specific for the tag used binds to the phage displaying the tag on the surface.

In another preferred embodiment, the cloning system comprises pre-digested vector arms with high ligation efficiency.

In another preferred embodiment, the cloning system comprises aliquoted phage packaging extracts, bacterial strains such as for example, BLT5616 *E. coli*, solution and other reagents, such as for example, IPTG solution.

The system and methodology described herein has many advantages over the currently available technologies. For example, the commercially available T/A cloning kits require labor intensive screening methods to identify positive clones. The positive clones that are identified will then have to be further screened for their full-length protein expression in cell culture by Western blot. However, if the frequency of full-length ORF cDNA insert among PCR-positive clones is relatively low, there is no way to enrich the clones with ORF cDNA insert. The only option would be to continue to screen more PCR-positive clones by Western blot. This has been shown to be a time-consuming process.

Labels:

The particular label or detectable moiety or tag used in the assay is not a critical aspect of the invention, as long as it does not significantly interfere with the specific binding of the ORF phage to their ligands. The detectable group can be any material having a detectable physical or chemical property. Such detectable labels have been well developed in the field of immunoassays and, in general, most labels useful in such methods can be applied to the present invention. Thus, a label is any composition detectable by spectroscopic, photochemical, biochemical, immunochemical, electrical, optical, or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horseradish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Solid State and Soluble High Throughput Assays:

In another embodiment, the invention provides solid phase based in vitro assays in a high throughput format, where the ligands are attached to a solid phase substrate, such as for example, an ELISA-like format.

In the high throughput assays of the invention, it is possible to screen up to several thousand different baits or ligands in a single day. In particular, each well of a microtiter plate can be used to run a separate assay against a selected potential ligand, or, if concentration or incubation time effects are to be observed, every 5-10 wells can test a single ligand. Thus, a single standard microtiter plate can assay about 100 (e.g., 96) ligands. If 1536-well plates are used, then a single plate can easily assay from about 1000 to about 1500 different compounds. It is also possible to assay multiple compounds in each plate well. It is possible to assay several different plates per day; assay screens for up to about 6,000-20,000 different compounds are possible using the integrated systems of the invention. More recently, microfluidic approaches to reagent manipulation have been developed.

The molecules of interest can be bound to the solid state component, directly or indirectly, via covalent or non-covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 2008 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, The Adhesion Molecule Facts Book I (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfliydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, J. *Am. Chem. Soc.,* 85:2149-2154 (1963) (describing solid phase synthesis of, e.g., peptides); Geysen et al., *J. Immun. Meth.,* 102:259-274 (1987) (describing synthesis of solid phase components on pins); Frank & Doring, Tetrahedron, 44:60316040 (1988) (describing synthesis of various peptide sequences on cellulose disks); Fodor et al., *Science,* 251:767-777 (1991); Sheldon et al., *Clinical Chemistry,* 39(4):718-719 (1993); and Kozal et al., *Nature Medicine,* 2(7):753759 (1996) (all describing arrays of biopolymers fixed to solid substrates). Non-chemical approaches for fixing tag binders to substrates include other common methods, such as heat, cross-linking by UV radiation, and the like.

The whole procedure can be fully automated. For example, sampling of sample materials may be accomplished with a plurality of steps, which include withdrawing a sample from a sample container and delivering at least a portion of the withdrawn sample to a test platform. Sampling may also include additional steps, particularly and preferably, sample preparation steps. In one approach, only one sample is withdrawn into the auto-sampler probe at a time and only one sample resides in the probe at one time. In other embodiments, multiple samples may be drawn into the auto-sampler probe separated by solvents. In still other embodiments, multiple probes may be used in parallel for auto sampling.

In the general case, sampling can be effected manually, in a semi-automatic manner or in an automatic manner. A sample can be withdrawn from a sample container manually, for example, with a pipette or with a syringe-type manual probe, and then manually delivered to a loading port or an injection port of a characterization system. In a semi-automatic protocol, some aspect of the protocol is effected automatically (e.g., delivery), but some other aspect requires manual intervention (e.g., withdrawal of samples from a process control line). Preferably, however, the sample(s) are withdrawn from a sample container and delivered to the characterization system, in a fully automated manner—for example, with an auto-sampler.

In one embodiment, auto-sampling may be done using a microprocessor controlling an automated system (e.g., a robot arm). Preferably, the microprocessor is user-programmable to accommodate libraries of samples having varying arrangements of samples (e.g., square arrays with "n-rows" by "n-columns," rectangular arrays with "n-rows" by "m-columns," round arrays, triangular arrays with "r-" by "r-" by "r-" equilateral sides, triangular arrays with "r-base" by "s-" by "s-" isosceles sides, etc., where n, m, r, and s are integers).

Automated sampling of sample materials optionally may be effected with an auto-sampler having a heated injection probe (tip). An example of one such auto sampler is disclosed in U.S. Pat. No. 6,175,409 B1 (incorporated by reference).

According to the present invention, one or more systems, methods or both are used to identify a plurality of sample materials. Though manual or semi-automated systems and methods are possible, preferably an automated system or method is employed. A variety of robotic or automatic systems are available for automatically or programmably providing predetermined motions for handling, contacting, dispensing, or otherwise manipulating materials in solid, fluid liquid or gas form according to a predetermined protocol. Such systems may be adapted or augmented to include a variety of hardware, software or both to assist the systems in determining mechanical properties of materials. Hardware and software for augmenting the robotic systems may include, but are not limited to, sensors, transducers, data acquisition and manipulation hardware, data acquisition and manipulation software and the like. Exemplary robotic systems are commercially available from CAVRO Scientific Instruments (e.g., Model NO. RSP9652) or BioDot (Microdrop Model 3000).

Generally, the automated system includes a suitable protocol design and execution software that can be programmed with information such as synthesis, composition, location information or other information related to a library of materials positioned with respect to a substrate. The protocol design and execution software is typically in communication with robot control software for controlling a robot or other automated apparatus or system. The protocol design and execution software is also in communication with data acquisition hardware/software for collecting data from response measuring hardware. Once the data is collected in the database, analytical software may be used to analyze the data, and more specifically, to determine properties of the candidate drugs, or the data may be analyzed manually.

Data and Analysis:

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention relates to embodiments that include methods for providing information over networks such as the Internet. For example, the components of the system may be interconnected via any suitable means including over a network, e.g. the ELISA plate reader to the processor or computing device. The processor may take the form of a portable processing device that may be carried by an individual user e.g. lap top, and data can be transmitted to or received from any device, such as for example, server, laptop, desktop, PDA, cell phone capable of receiving data, BLACKBERRY™, and the like. In some embodiments of the invention, the system and the processor may be integrated into a single unit. In another example, a wireless device can be used to receive information and forward it to another processor over a telecommunications network, for example, a text or multi-media message.

The functions of the processor need not be carried out on a single processing device. They may, instead be distributed among a plurality of processors, which may be interconnected over a network. Further, the information can be encoded using encryption methods, e.g. SSL, prior to transmitting over a network or remote user. The information required for decoding the captured encoded images taken from test objects may be stored in databases that are accessible to various users over the same or a different network.

In some embodiments, the data is saved to a data storage device and can be accessed through a web site. Authorized users can log onto the web site, upload scanned images, and immediately receive results on their browser. Results can also be stored in a database for future reviews.

In some embodiments, a web-based service may be implemented using standards for interface and data representation, such as SOAP and XML, to enable third parties to connect their information services and software to the data. This approach would enable seamless data request/response flow among diverse platforms and software applications.

Kits

In a preferred embodiment, a kit comprises a phage vector wherein the vector comprises a tag molecule expressed when a full length open reading frame nucleic acid sequence is inserted. The kit can further comprise phage vectors having different tags, for example, FLAG, c-myc, biotin, and the like. Optionally, the kit can include the tag specific capture element.

In another preferred embodiment, the kit further comprises an oligo-dT primer, restriction endonucleases and polymerases for amplification in a polymerase chain reaction. Preferably, instructions for use are included. Said instructions include a method, for example: isolating and purifying nucleic acid molecules from a sample; inserting the nucleic acid sequence into the vector, isolating and enriching the phage comprising the desired open reading frame nucleic acid sequence.

In another preferred embodiment, the kit further comprises reagents and materials, including pre-digested phage vector arms, aliquoted phage packaging extracts, bacterial strains such as for example, BLT5616 *E. coli*, IPTG solution, 8-well strips (in 96-well format), streptavidin solution and a product manual. Pre-digested vector arms with high ligation efficiency are provided with the kit or purchased separately from the kit.

The invention also provides methods for using kits of the invention for carrying out a variety of bioassays. Any type of assay wherein one component is immobilized may be carried out using the substrate platforms of the invention. Bioassays utilizing an immobilized component are well known in the art. Examples of assays utilizing an immobilized component include for example, immunoassays, analysis of protein-protein interactions, analysis of protein-nucleic acid interactions, analysis of nucleic acid-nucleic acid interactions, receptor binding assays, enzyme assays, phosphorylation assays, diagnostic assays for determination of disease state, genetic profiling for drug compatibility analysis, SNP detection, etc.

The above disclosure generally describes the present invention. A more complete understanding can be obtained by reference to the following specific examples, which are provided herein for purposes of illustration only and are not intended to limit the scope of the invention.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

Example 1

Cloning of Full Length cDNA Sequences

Materials and Methods
RT-PCR of Tubby:
Total RNA was purified from the retina of C57BL/6 mice (4-weeks old) by TRIzol reagents (Invitrogen) according to the manufacturer's protocol. Reverse transcription was performed using SuperScript II reverse transcriptase (Invitrogen) with oligoT priming method. Full-length tubby coding sequence was generated by 30-cycle PCR amplification using Extend High Fidelity Taq (Roche). The primers used for the RT-PCR were 5'-TA GCGGCCGCTA ATG ACT TCC AAG CCG CAT TC-3'(SEQ ID NO: 8) and 5'-AG CTCGAG CTC GCA GGC CAG CTT GCT GTC-3' (SEQ ID NO: 9) (underlined sequences for Not I and Xho I cleavage sites). The C-terminal stop codon was removed in the downstream primer.

Phage Vector:
The linker sequence of 5'-GCGGATCCG CGG CCG CTA TAA CTCGAG GGT AGT GGG AGC GGA TTA AAT GAT ATA TTT GAG GCA CAA AAA ATT GAA TGG CAT TAA GAATTC AAGCTT GTCGACGC-3' (SEQ ID NO: 10) (underlined sequences are BamH I and Sal I cutting sites, italic sequence is biotinylation epitope) was generated by PCR using a series of overlapping primers, digested with BamH I and Sal I, ligated into T7Select10-3b vector (Novagen) at BamH I and Xho I sites to yield PH737 vector. The engineered phage vector was verified by sequencing.

The DNA linker sequence (SEQ ID NO: 10) was generated by mixing the following three overlapping primers, followed by 10-cycle PCR amplification.

```
Primer 1:                           (SEQ ID NO: 11)
5'-CGG GAT CCG CGG CCG CTA TAA CTC GAG GGT AGT GGG
AGC GGA TTA AAT G-3'.

Primer 2:                           (SEQ ID NO: 12)
5'-AGT GGG AGC GGA TTA AAT GAT ATA TTT GAG GCA
CAA AAA ATT GAA TG-3'.

Primer 3:                           (SEQ ID NO: 13)
5'-ACG TCG ACA AGC TTG AAT TCT TAA TGC CAT TCA ATT
TTT TGT GCC TC-3'.
```

The liner sequence was purified on 2% gel, digested with BamHI and SalI. The digested DNA was re-purified with a PCR purification kit (Qiagen), and ligated with T7 phage DNA (T7Select1-3b vector) (Novagen) predigested with BamHI and XhoI. The ligation mixture was packaged into phage using phage packaging extract (Novagen). The resulting individual phage clones were analyzed by PCR using Primer 2 and a downstream primer (5'-CCAAAGAATCGGT-TGTTGAA-3' (SEQ ID NO: 14)). The positive clones with a 594-bp PCR reaction product were selected and verified by DNA sequencing.

To insert tubby ORF cDNA sequence digested with NotI and XhoI, the engineered phage DNA was digested with NotI and XhoI, and the vector arms were purified.

Phage Protocol:
All procedures for T7 phage display, including phage DNA purification, digestion, ligation, phage packaging, plaque assay, phage liquid amplification and plating in BLT5615 *E. coli*, were performed according to Novagen's T7 Select system manual (available at www.emdbiosciences.com/docs/PROT/TB178.pdf).

Reagents and Materials:
CsCl stock: 62.5% (g/g) [25 g CsCl+15 ml ddH$_2$O]. Dialysis buffer: 0.1 M NaCl, 0.1 M Tris-HCl, pH 8.0.

| CsCl:TE | SW41 (total 12 ml) | SW60 (total 4 ml) | |
|---|---|---|---|
| 1:2 (0.6 ml + 1.2 ml) | 2 ml | 0.67 ml | Top |
| 1:1 (0.9 ml + 0.9 ml) | 2 ml | 0.67 ml | |
| 1:2 (1.2 ml + 0.6 ml) | 2 ml | 0.67 ml | |
| 1:0 | 1 ml | 0.333 ml | Bottom |

T7 Phage DNA Preparation:
400 ml of T7 phage lysate was prepared, 10 g of NaCl, was added, mixed and dissolved. This was spun in a Sorvall GSA rotor at 9,000 rpm at 4° C. for 10 min, the supernatant collected and mixed with 40 g of PEG-8000 until it dissolved, and then stored at 4° C. overnight. This was then centrifuged in a Sorvall GSA rotor at 9,000 rpm at 4° C. for 10 min and the phage pellet was resuspended in 3.3 ml of dialysis buffer. A discontinuous CsCl gradient was generated in two ultracentrifuge tubes for use in a SW60 rotor and the phage solution was carefully loaded onto the tubes. This was centrifuged using a SW60 rotor at 38377 rpm for 1 h at 23° C. The phage band was collected (right in the middle of the 4 CsCl layers) and mixed with equal volumes of CsCl (62.5%). A second CsCl is optional: another CsCl was generated as follow: 0.33 ml CsCl (1:0) (Bottom); phage-CsCl mixture (middle);

remaining volume CsCl (1:1) (top); the centrifugation was repeated with the same conditions as above. The phage band was collected and dialyzed against dialysis buffer using a minimum of 100 volumes of buffer over phage volume. The buffer was changed four times, 1 h each, at room temperature. The final dialysis was carried out at 4° C. overnight. The phage solution was collected and $MgCl_2$ (Final 2.5 mM) and $CaCl_2$ (final 0.5 mM) were added. 2 µl RNase (200 mg/ml) (Qiagen Cat. #19101 or equivalent) and 20 µl DNase (1,000 units/ml) (Sigma Cat. #DN25-100 mg, re-hydrolyzed) were added and digestion was carried out at 37° C. for 30 min-1 h. EDTA (final 10 mM) was added, mixed, Proteinase K (final 300 µg/ml) was then added followed by addition of SDS (final 0.2%) and incubated at 50° C.-55° C. for >1 h or overnight. The mix was diluted to 3.6 ml with the dialysis buffer and divided into four 2-ml tubes (0.9 ml each). Extraction was conducted with phenol according to Novagen protocol. After Chloroform:isoamyl alcohol extraction, all DNA solution was combined in a 15 ml tube; an equal volume of isopropanol was added, mixed and the aggregated DNA was picked with a pipettor tip. This was then rinsed with 70% ice-cold alcohol, the aggregated DNA was picked up with a pipettor tip and air dried. The DNA was dissolved in DEPC $H_2O$ at ~1 mg/ml.

Phage DNA Preparation:

phage should be purified by double CsCl centrifugation, followed by phenol extraction, strictly according to Novagen protocol (restriction digestion efficiency for phage DNA prepared by other methods will be relatively poor for library construction). Phage DNA (60 µg) was digested in 600 µl of digestion buffer with NotI (6 µl), XhoI (6 µl), for 16 h at 37° C. The solution was extracted with equal volume of an equal volume of phenol/chloroform for three times, followed with an equal volume of chloroform twice. The DNA solution was mixed with a 1/10 volume of 3M NaAc and 2 µl of glycogen, and precipitated with an equal volume of isopropanol (mix, keep at –20° C. for 30 min, spin for 20 min at 4° C., wash the pellet with 1 ml of ice-cold 75% EtOH). The pellet was air dried (only semi-dry. The pellet was not completely dried as it is very difficult to dissolve the DNA). DNA was dissolved in ~40 µl of DEPC $H_2O$. If necessary, DNA may be heated for 10 min at 55° C. to accelerate the re-hydration. (keep DNA dissolved in smallest volume with highest concentration without gel-like clump is one of the important steps to achieve high packaging efficiency for the cDNA library). DNA concentration was then determined (~1 µg/µl).

DNA Ligation and Packaging:

1.5 µl of digested phage DNA (~1.5 µg) was mixed with 60 ng tubby cDNA insert, and the following were added: 0.25 µl of 10× ligation buffer+0.25 µl of 10 mM ATP+0.25 µl of 100 mM DTT), 0.25 µl of T4 DNA ligase (total reaction volume 2.5 µl). This was mixed and incubated at 16° C. overnight. The ligation mixture (0.2 µl) was added to 1 µl of packaging extract (Novagen, Inc.) and incubated at RT for 2 h. 300 µl of LB was added, mixed and the phage titer was determined by plaque assay.

Construction and Screening of Tubby-Phage:

The RT-PCR product of full-length tubby ORF was purified from agarose gel, digested with Not I and Xho I and ligated into the phage vector at Not I and Xho I sites with T4 DNA ligase. Ligation mixture (0.2 µl) was packaged with T7 phage packaging extract (Novagen) (1 µl) according to the manufacture's protocol. Packaged phages in LB medium were analyzed for their initial titer by plaque assay and amplified in *E. coli* BLT5615. Packaged phages were titrated by infecting BLT5615 and plating on LB agar plates. Tubby-expressing phage clones (Tubby-phage) were screened by PCR using T7up-F5 primer 5'-AGCAAACTACGCT-GCTCTGA-3' (SEQ ID NO: 15) (annealing to the phage vector) and tubby-R primer 5'-ACTGTAAGGAATC-CAGTCGGA-3' (SEQ ID NO: 16) (annealing to tubby coding sequence). The phage DNA was directly transferred from individual plaques on the phage plates into individual PCR tubes by touching the plaques with clean toothpicks or pipettor tips and shaking them in PCR solution (20 µl/PCR tube). A typical PCR program was 94° C. for 2 min, (94° C. for 20 sec., 55° C. for 30 sec. and 72° C. for 1 min)×40, 72° C. for 5 min. Ligation mixture (0.2 µl) may be used as a positive control for PCR reaction. PCR products were analyzed with 1% agarose gel.

Phage Binding to Streptavidin:

Streptavidin in phosphate-buffer solution (PBS) was coated onto 8-well strips (E.I.A./R.I.A., Costar, #2592) (5 µg/ml, 100 µl/well) overnight at 4° C. After washing, the plates wells were blocked with blocking buffer (1% BSA, 5% sucrose, 0.05% $NaN_3$ in PBS) for 1 h. Individual phage clones were picked by toothpicks and amplified in BLT5615 (0.3 ml bacteria solution in 2 ml microcentrifuge tubes) by shaking at 37° C. until lysis. The phage lysates were centrifuged at 13,000 g for 1 min. The supernatants (100 µl/phage) were incubated for 30 min with the immobilized streptavidin in the presence of 0.2% Tween-20. Positive control phage (Biotin-Phage without stop codon between Not I and Xho I site) and negative control phage (PH737 with a stop codon between Not I and Xho I site) were included. The plates were washed with PBS plus 0.2% Tween-20 (PBST) for 6 times with 5 min each. The bound phages were eluted by 1% SDS for 10 min, and the eluates were immediately diluted 100-fold with LB medium. The eluted phages were titrated by plaque assay.

Results and Discussion

The traditional approach to clone a full-length cDNA ORF is to amplify the ORF by RT-PCR, ligate the gel-purified ORF into a plasmid and verify the sequence by DNA sequencing. However, mRNA transcript may have nonsense variants expressing truncated proteins. The heterogeneous mRNA transcripts may derive from alternative splicing, deletions, insertions, transitions, transversions and editing. During the cloning of several full-length cDNA ORFs from mouse retina, we have encountered a number of cases that their isolated coding sequences with predicted lengths were transcript variants with internal stop codons. For example, tubby (GenBank accession # NM_021885) has a coding region of 1515 bp. Tubby was previously identified from tubby mice with spontaneous mutation in tubby gene. Autosomal recessive mutation causes adult-onset obesity, deafness and retinal degeneration. The mutation is due to IVS11+1G→T transversion in Intron 11, which leads to mRNA alternative splicing and replacement of the C-terminal 44 amino acid (aa) chain with a 22-aa polypeptide derived from the same intron.

A full-length coding sequence from the retina of wild-type mice was generated by PT-PCR and ligated the gel-purified 1.5-kb tubby coding region PCR product into pGEM-T Easy vector (Promega). However, most of the clones with cDNA inserts were nonsense sequence expressing truncated tubby with premature stop codons. The traditional approach to solve this problem is to sequence a number of clones until a full-length clone is found. This could be quite time-consuming, if the frequency of ORF is low. Coupling with convention plasmid cloning problems, such as low ligation and transformation efficiency for longer DNA inserts, isolation of a full-length tubby ORF from mouse retina became quite difficult.

To overcome the challenge for cloning ORFs of tubby and other genes, a bacteriophage T7 display vector for the rapid cloning of their full-length ORFs was developed. With tubby ORF inserted in appropriate reading frame, the protein was expressed as fusion protein of phage capsid 10B with a C-terminal 13-amino acid peptide for biotinylation by *E. coli* biotin ligase (BirA). Phage clones with the full-length tubby ORF insert were biotinylated, whereas non-ORF phages could not express the C-terminal biotinylation peptide epitope. Thus, only the phage clones with high binding activity to streptavidin had an ORF insert. A full-length tubby coding sequence without the C-terminal stop codon was generated by RT-PCR, the gel-purified tubby ORF was ligated into the digested phage vector at NotI and XhoI sites, the ligation mixture was packaged with phage packaging extract and yielded a total of $8.8 \times 10^4$ pfu (plaque forming unit) phages. The individual phage plaques with cDNA insert were identified by PCR using T7up-F5 and tubby-R primers. Analysis of 20 tubby-phage clones revealed that none of them were biotinylated, indicating that all of them were nonsense transcripts. These data also indicated that the ratio of tubby ORF vs. nonsense transcripts in mouse retina was quite low. Similar results were also obtained for the tubby transcripts from mouse brain.

To isolate full-length tubby ORF, the packaged phages in BLT5615 *E. coli* were amplified, the biotinylated phages were selected with immobilized streptavidin, and 20 new phage clones were identified with tubby cDNA insert from the enriched phage pool by PCR screening. It is noteworthy that the frequency of tubby-positive clones was much higher in the enriched phage pool than in the unenriched phages, indicating that many phage clones without cDNA inserts were eliminated by the enrichment. Furthermore, the enrichment also effectively eliminated phages with the non-ORF insert. As a result, the streptavidin binding analysis showed that eight out of twenty tubby-positive phage clones exhibited about ~1,000-fold increase in phage binding activity to immobilized streptavidin. These streptavidin-binding phage clones were verified as tubby ORF by DNA sequencing.

Unlike the PCR cloning plasmids, the phage display vector allowed the enrichment of the phages with ORF insert. This enrichment efficiently eliminated phage clones with no cDNA insert or with nonsense insert. This made the identification of phage clones with ORF insert much easier. This technology can identify a single clone of ORF phage from the tens of thousands of packaged phages with nonsense insert. If necessary, additional round of streptavidin binding may be performed to further increase the percentage of ORF-phage in the total enriched phages. The additional advantage of the system is that packaging efficiency of the phage vector. Longer cDNA inserts often have lower ligation efficiency. This often leads to lower plasmid transformation efficiency and fewer colonies. On the other hand, phage vector often yields $10^5$-$10^8$ packaging efficiency, much more efficient than plasmid transformation. As long as there is single phage clone with ORF, it can be readily isolated by phage enrichment. Isolated phage clones with cDNA insert can be verified for ORF insert by the binding assay to immobilized streptavidin. Finally, the clone protein expressed and displayed on the phage surface can offer convenient recombinant protein to analyze their binding activity or other function.

Example 2

ORF Phage Display: The Fastest, Most Convenient and Versatile Technology for Functional Proteomics Materials and Methods
T7 Phage Display Vector:
The linker sequence of 5'-CGGGATCCG CTG GAA GTG CTG TTT CAG GGC CCG GGC AGC GGT TCA GGC TCG CGG CCG CTA GAT ATC TAA CTC GAG GGT AGT GGG AGC GGA TTA AAT GAT ATA TTT GAG GCA CAA AAA ATT GAA TGG CAT TAA GAATTC AAGCTT GTCGAC GT-3' (SEQ ID NO: 17; underlined sequences are BamHI and SalI cleavage sites, and italic sequence for biotinylation epitope) was generated by PCR using overlapping primers, digested with BamHI and SalI, and ligated into T7Select10-3b vector (Novagen, Madison, Wis.) at BamHI and XhoI sites to yield T7Bio3C vector in FIG. 1A.

ORF Phage Display cDNA Library:
Total RNA was extracted from 40 freshly isolated mouse eyes or 4 mouse embryos at day 18 by TRIzol reagent (Invitrogen, Carlsbad, Calif.). mRNA was purified using Oligotex mRNA purification kit (Qiagen, Valencia, Calif.). The orientation-directed cDNA library was generated. Briefly, the first-strand cDNA was generated by SuperScript II reverse transcriptase (Invitrogen, Carlsbad, Calif.) with the first-strand tagged primer. After removal of the mRNA by RNase H, the second-strand cDNA was generated by Klenow (3'→5' exo-) with the second-strand tagged primer. The cDNA library was amplified by a unique strategy of frame-shift PCR for 30 cycles with three forward primers and three reverse primers.

```
First-strand tagged primer:            (SEQ ID NO: 18)
5'-GCG CCG CGA CCN NNN NNN NN-3'.

Second-strand tagged primer:           (SEQ ID NO: 19)
5'-GGC CGG CCT CCN NNN NNN NN-3'.

Forward primers for frame-shift PCR:
                                       (SEQ ID NO: 20)
5'-A ACT AGA TAA GAA TAG CGG CCG CGC GCC GCG
ACC-3';

(SEQ ID NO: 21)
5'-A ACT AGA TAA GAA TAG CGG CCG CAG CGC CGC
GAC C-3';

(SEQ ID NO: 22)
5'-A ACT AGA TAA GAA TAG CGG CCG CAA GCG CCG
CGA CC-3';
(underlined sequences are NotI cutting sites).

Reverse primers for frame-shift PCR:
                                       (SEQ ID NO: 23)
5'-AAT GAT CTC GAG GGC CGG CCT CC-3';

(SEQ ID NO: 24)
5'-AAT GAT CTC GAG TGG CCG GCC TCC-3';

(SEQ ID NO: 25)
5'-AAT GAT CTC GAG TAG GCC GGC CTC C-3';
(underlined sequences are XhoI cutting sites).
```

The PCR product was purified using a PCR purification kit (Qiagen) to remove primers and PCR products smaller than 100 bp. The cDNA fragments between 300 bp-1.5 kb were purified on 2% agarose gel, digested with NotI and XhoI, and ligated into T7Bio3C vector that was pre-digested with NotI, XhoI and EcoRV. Triple digestion was to minimize vector self-ligation. Ligated DNA was packaged into T7 phage using T7 phage package extract (Novagen). The original phage library titer was ~$2 \times 10^7$ pfu for the eye library and ~$1 \times 10^8$ pfu for the embryo library. The libraries were amplified once on BLT5615 bacterial plates, enriched for biotinylated phages by binding to streptavidin-coated paramagnetic beads (Promega, Madison, Wis.) and eluted with 3C protease (5 units in 200 µl) (available from Novagen) at 4° C. for 16 h to generate ORF libraries. The libraries were amplified once on the bacterial plates with a final titer of ~$1 \times 10^{10}$ pfu/ml. All procedures for T7 phage display, including phage DNA purification, digestion, ligation, phage packaging, plaque assay, phage liquid amplification and plating in BLT5615 bacterial plates, were carried out according to Novagen's T7Select System Manual (available at www.emdbiosciences.com/docs/docs/PROT/TB178.pdf).

Distribution of cDNA Insert Size:

Individual phage clones were randomly picked from phage plates of the cDNA libraries immediately after packaging. cDNA inserts were amplified by PCR with T7SelectUp and T7SelectDown primers (Novagen), and analyzed on 2% agarose gel. The actual cDNA insert sizes were calculated by subtracting 239 bp of the sequences for the phage backbone and tagged sequences in the random primers.

```
T7SelectUp primer:          (SEQ ID NO: 26)
5'-CCA AGC GGA CCA GAT TAT CG-3'

T7SelectDown Primer:        (SEQ ID NO: 27)
5'-GAG CGC ATA TAG TTC CTC CT-3'.
```

ORF Phage Display:

Phage selection was carried as follows. ELISA plates (Corning Life Science, Lowell, Mass.; 8-well strip, #2592) were coated with purified tubby-N [10 µg/ml in phosphate buffered saline (PBS), 100 µl/well] at 4° C. overnight or 37° C. for 1 h, blocked for 1 h with 1% bovine serum albumin (BSA) or 1% polyvinyl alcohol (PVA) in PBST (PBS plus 0.1% Tween-20) and incubated with the phage library (~1× $10^{10}$ pfu/ml, 0.1 ml/well) in the presence of 0.1% Tween-20 for 1 h at room temperature. The wells were washed with PBST for 6 min×6. Bound phages were eluted with 3C protease (2 units/well in 100 µl of PBS) at 4° C. for 1 h. An aliquot of eluted phages (1 µl) was diluted appropriately and quantified by plaque assay to determine total eluted phages. The remaining eluate was amplified in BLT5615 bacterial strain. The lysate was clarified by centrifugation (13,000×g for 4 min) and used as input for the next round of selection. Because of the robust growth rate of T7 bacteriophage, the entire procedure for each round of selection took only ~4 h. After three rounds of selection, enriched phages were selected twice with immobilized streptavidin in a similar fashion. The selection of Axl-binding phages was performed similarly with immobilized Axl-Fc (R&D Systems, Minneapolis, Minn.).

For the selection of phosphatidylserine (PS)-binding phages, the ELISA plates were coated with PS (Sigma, St. Louis, Mo.; P7769) (10 nmol/ml in methanol, 100 µl/well). After evaporation of the solvent, the plates were blocked with 1% fatty acid-free BSA (Sigma, A6003) or 1% PVA in PBS. The remaining procedure of ORF phage display for PS was the same as for tubby-N, except that all solutions had no Tween-20.

BLT7FLAG and BLT7Bio Bacteria:

pGEX-2T plasmid (GE Healthcare, Piscataway, N.J.) was engineered to remove glutathione S-transferase (GST) coding sequence as the following. A DNA fragment was generated from pGEX-2T by PCR using primers 5'-TGCG-GATATCTCGGTAGTG-3'(SEQ ID NO: 28) and 5'-ATGAATTC TCTAGAGTCGAG GAATACTGTTTCCT-GTGTG-3' (SEQ ID NO: 29), digested with EcoRV and EcoRI, ligated back into pGEX-2T at the same sites to yield plasmid A. A cDNA coding sequence for capsid 10A (22921-24001 bp in GenBank accession #V01146) was amplified from wild-type bacteriophage T7 by PCR, fused with a C-terminal FLAG tag by PCR with overlapping primers, digested with XbaI and EcoRI, and inserted into plasmid A at the same sites. The resulting plasmid was confirmed by DNA sequencing and transformed into BL21 bacteria to generate BLT7FLAG strain with carbenicillin selection. BLT7FLAG bacteria at an $OD_{600}$ of 0.5 were induced by isopropyl β-D-1-thiogalactopyranoside (IPTG) (1 mM) for 30 min to express capsid 10A-FLAG fusion protein and used as host bacteria for phage amplification. BLT7Bio bacterial strain was generated in a similar manner by fusing a biotinylation tag to the C-terminus of capsid 10A.

Colorimetric Assay:

Enriched phages were plated in BLT5615 bacteria plates at appropriate density. Individual phage clones were randomly isolated and amplified in BLT7FLAG bacteria in 96-well plates (V-bottom, 130 µl bacteria/well) by shaking at 37° C. until lysis. After centrifugation at 1,400 g for 10 min, supernatants (50 µl/well) were incubated with immobilized bait or mock control in the presence of 0.1% Tween-20 (no Tween-20 for PS). After washing, bound phages were incubated with anti-FLAG M2 monoclonal antibody (mAb) (Sigma), followed with horseradish peroxidase (HRP)-conjugated goat anti-mouse IgG. After washing, bound HRP was visualized with 100 µl of o-phenylenediamine (OPD) (0.4 mg/ml) and $H_2O_2$ (0.01%) in citric acid buffer (20 mM citric acid, 40 mM $NaH_2PO_4$, pH5.0), stopped with 100 µl of 1 M $H_2SO_4$ and quantified by a plate reader at 490 nm.

Tubby-N:

The coding sequence for the N-terminus of mouse tubby (1M-242P) was generated by reverse transcription PCR (RT-PCR) from mouse retina and cloned into pGEX-2T plasmid with an additional 3C protease cleavage site between GST and tubby-N. GST-tubby-N fusion protein was expressed in BL21(DE3) bacteria, purified with a glutathione column and eluted with reduced glutathione. GST-tagged 3C protease was expressed and purified in a similar manner, but without the 3C protease cleavage site. Purified GST-tubby-N was dialyzed against PBS to remove reduced glutathione in the presence of GST-tagged 3C protease (~20 units) at 4° C. GST-free tubby-N was purified by depleting GST, GST-3C protease and other glutathione binding impurities with a glutathione column. The quality of purified tubby-N was analyzed by SDS-PAGE (FIG. 6).

Full-Length Tubby (Tubby-F):

To eliminate the possibility that identified clonal phages may bind to trace amount of possible contaminated GST or other bacterial proteins in the purified tubby-N, was expressed and purified recombinant tubby-F from mammalian cells as the following. The complete coding sequence of tubby-F was generated by RT-PCR from mouse retina and cloned into pAdTrack-CMV plasmid at BglII and SalI sites with an N-terminal FLAG tag. Recombinant adenovirus expressing FLAG-tubby-F was generated and used to infect HEK293 cells. FLAG-tubby-F was purified using an anti-FLAG mAb affinity column (Sigma), eluted with FLAG peptide (100 µg/ml), dialyzed against PBS and analyzed by SDS-PAGE. Control green fluorescent protein (GFP) with a C-terminal FLAG tag was constructed, expressed and purified in a similar manner. Purified tubby-F and GFP were immobilized in the ELISA plates at 5 µg/ml and used for phage binding assay.

Figures 3A, 3B:
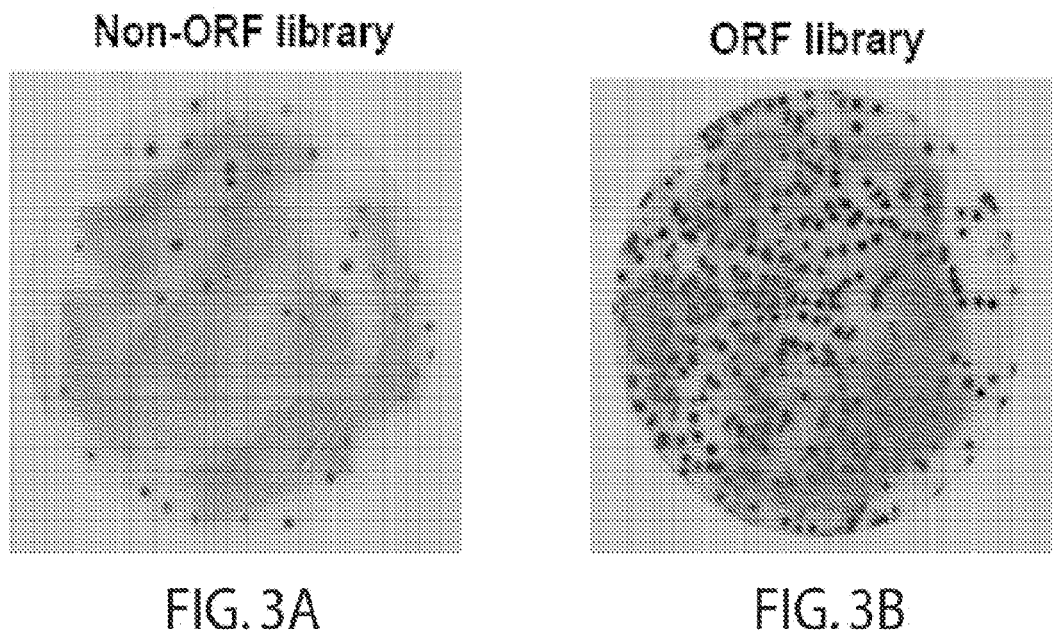
FIG. 3 is a scan of a photograph showing the analysis of ORF library by immunoblotting. The packaged phage cDNA library of mouse eye was amplified in BLT5615 bacteria and enriched by binding to immobilized streptavidin to generate ORF cDNA library. The library before (A) and after (B) the enrichment was plated on BLT5615 bacterial plates at a similar density. The expression of the biotinylation tag in individual phage clones was analyzed by immunoblotting using streptavidin-conjugated HRP (horseradish peroxidase) and chemiluminescence detection. Positive signals indicated that the phage clones expressed the biotinylation tag with ORF cDNA inserts. More than 90% of phage clones in the ORF library had ORF inserts.

Yeast Two-Hybrid Assay:

cDNA for tubby-N was cloned into pGBT9 (Clontech, Mountain View, Calif.) plasmid at EcoRI and BamHI sites. cDNA inserts from the identified phages were amplified by PCR and cloned into pGAD424 plasmid (Clontech) at BamHI and SalI sites. Yeast two-hybrid assay was performed according to the manufacturer's protocol. Briefly, *S. cerevisiae* CG-1945 strain was co-transformed with cDNA insert/pGAD424 and tubby-N/pGBT9 or pGBT9 control as indicated in FIG. 3c. The transformed yeast was selected on agar plates with double (-Leu/-Trp) or triple (-Leu/-Trp/-His)

dropout of the essential amino acids. Dropout-resistant yeast clones were re-grown on YPD plates, lifted onto a filter paper and analyzed for galactosidase expression using X-gal as a substrate.

Protein Pull-Down Assay:

GST-tubby-F was constructed in pGEX-2T plasmid, expressed in BL21(DE3) bacteria and purified using a glutathione column. Full-length coding sequence of mouse Hmgb2 (Open Biosystems, Huntsville, Ala.) was amplified by PCR and cloned into pcDNA3 with an N-terminal FLAG tag. HEK293 cells were transfected with the plasmid expressing FLAG-Hmgb2 using Lipofectamine reagent (Invitrogen). The cells were harvested at 48 h post-transfection and washed. Cell lysate was prepared in PBS containing 0.5% Triton X-100, spun and incubated with purified GST-tubby-F or GST control, followed by glutathione resin. The resin was washed and analyzed by Western blot using anti-FLAG mAb.

Liposome Binding Assay:

PS or phosphatidylcholine (PC) liposomes were prepared. The cDNA coding sequences of Akap12 (345D-522G), pinin (187Q-306E) and serum response factor binding protein 1 (Srfbp1) (110V-264E) were amplified by PCR from PH169, PH166 and PH195 phage clones (Table 4), respectively, and cloned into pGEX-2T plasmid. GST fusion proteins were expressed in BL21(DE3) bacteria and purified. Liposomes (50 nmol) were incubated with GST or GST fusion proteins (~10 µg) in 0.5 ml PBS at 4° C. for 1 h, washed four times with ice-cold PBS by centrifugation at 230,000×g for 30 min at 4° C., and analyzed by Western blot using anti-GST mAb (AnaSpec, San Jose, Calif.).

Bioinformatics Analysis:

All cDNA insert sequences of identified bait-binding phage clones were analyzed by BLAST search against the GenBank database. Translated amino acid sequences of phage cDNA inserts were further aligned to the protein sequences of the matched genes.

ORF Phage Display cDNA Library:

The quality of the library is important for the technology and is mainly determined by three parameters: the size range of the double-stranded cDNA, the phage library titer immediately after phage packaging and the size distribution of cDNA inserts in the phage library. First, the size range of the double-stranded cDNA library generated by the random priming method should be centered between 300-1,000 bp. This size range is generally influenced by the ratio of random primer:mRNA. Longer cDNA inserts in the library may have natural stop codons at the 3'-ends of cDNA coding sequences, which prevent the expression of C-terminal biotinylation tag.

Second, the initial titer of the packaged phage library directly determines the representation of the library. This titer is mainly influenced by ligation and packaging efficiency. Finally, the size distribution of the phage cDNA library is another important factor. Too many short cDNA inserts may lead to high frequency of non-coding sequences without a stop codon.

Elimination of False Positives:

Possible false positives are a major concern for the screening of protein-protein interaction. In Y2H, false positives are eliminated by triple dropout of essential amino acids coupled with analysis of β-galactosidase expression. In ORF phage display, positive clones identified by the colorimetric assay should be vigorously verified. If necessary, phage plaque assay should be used to determine total bound phages with more accuracy. Control phage without cDNA insert or irrelevant cDNA insert should always be included as a negative control. Whenever available, appropriate positive controls should be used as a reference. A possible source of false positives is plate-binding phages or phages binding to blocking reagents. A blank control is essential to eliminate such false positives. Another major source of false positives in ORF phage display is the possible impurities in the bait. Quality control of bait protein is important. Whenever possible, bait protein purified from different sources with different purification procedures should be used to validate bait-binding activity of identified phage clones. The concept of tandem affinity purification could be potentially integrated into the future procedures for bait purification and/or phage panning. Independent verifications, including Y2H, co-immunoprecipitation or protein pull-down assay, should be used to further confirm the physical interaction between the bait and identified proteins. Demonstration of biological relevance is dependent on the nature of identified proteins.

In this study, all the identified phage clones were verified by phage plaque assay (Tables 2, 3 and 4). Tubby-F purified from a different source with a different affinity column was used to validate identified clones. Y2H was used to confirm their interactions. The physical interaction of tubby with Hmgb2 (FIG. 2E) and Tulp1 was further verified by protein pull-down assay. Moreover, functional interaction between tubby and Tulp1 was demonstrated by their synergistic stimulation on retinal pigment epithelium (RPE) cell phagocytosis. For the PS-binding proteins, their binding activities and specificities to different phospholipids were verified with clonal phages and GST fusion proteins (Table 4 and FIG. 2F). MFG-E8-Phage was used as a positive control (Table 4 and FIG. 7).

TABLE 2

Tubby-binding proteins.

| Protein Name | Accession number | Matched aa residues | Freq[a] | Binding to tubby-N[b] | Binding to tubby-F[c] | Verifiable by Y2H[d] |
|---|---|---|---|---|---|---|
| ORF matched to protein coding sequence | | | | | | |
| Zinc finger E-box binding homeobox 1 (Zeb1) (N) | NM_011546 | 903E-1021E | 2 | ~284.0X | ~28.7X | ++ |
| Zinc finger protein 609 (Zfp609) (N) | NM_172536 | 1M-183E | 2 | ~53.2X | ~2.3X | +/− |
| CCCTC-binding factor (Ctcf) (N) | NM_181322 | 136G-400T | 1 | ~117.4X | ~44.9X | + |
| PC4 and SFRS1 interacting protein 1 (Psip1) (N) | NM_133948 | 152K-219K | 4 | ~196.3X | ~24.0X | + |
| High mobility group box 2 (Hmgb2) (N) | NM_008252 | 89K-188E | 5 | ~312.4X | ~21.7X | + |
| High mobility group box 2-like 1 (Hmgb2l1) (N) | NM_178017 | 170K-305G | 1 | ~29.8X | ~5.0X | + |
| High mobility group nucleosomal binding domain 1 (Hmgn1) (N) | NM_008251 | 1M-49K | 2 | ~61.4X | ~9.5X | − |
| High mobility group nucleosomal binding domain 2 (Hmgn2) (N) | NM_016957 | 1M-56K | 1 | ~33.4X | ~9.5X | + |
| IQ motif containing GTPase activating protein 2 (Iqgap2) | NM_027711 | 1232E-1368E | 1 | ~53.2X | ~1.8X | NT |
| Paf1/RNA polymerase II complex component (Rtf1) | XM_917502 | 69N-186K | 1 | ~6.4X | ~6.2X | +/− |
| Tubby like protein 1 (Tulp1) | NM_021478 | 125D-243E | 1 | ~49.0X | ~29.1X | +++ |

TABLE 2-continued

Tubby-binding proteins.

| Protein Name | Accession number | Matched aa residues | Freq[a] | Binding to tubby-N[b] | Binding to tubby-F[c] | Verifiable by Y2H[d] |
|---|---|---|---|---|---|---|
| ATP-binding cassette F1 (Abcf1) | NM_013854 | 57K-196G | 2 | ~68.2X | ~27.2X | ++ |
| Structure specific recognition protein 1 (Ssrp1) | NM_182990 | 486E-619G | 2 | ~156.9X | ~4.5X | + |
| Microtubule-associated protein 7 (Mtap7) | NM_008635 | 23A-114R | 1 | ~3.5X | ~3.8X | − |
| Regulated endocrine-specific protein 18 (Resp18) | NM_009049 | 68V-134K | 1 | ~10.3X | ~4.8X | + |
| ORF matched to unknown proteins | | | | | | |
| Chromosome X Genomic contig. alternate assembly[e] | NW_001035178 | | 1 | ~40.1X | ~3.1X | NT |
| Non-ORF | | | 0 | | | |

[a]Clone frequency. All clones, including 8 nuclear proteins, were independent. Only the minimal overlapping amino acid sequences are shown for the proteins with multiple clones.
[b]The binding specificity of clonal phages vs. control phage.
[c]The binding specificity to FLAG-tubby-F vs. to GFP-FLAG.
[d]+++, strong signal for X-gal staining; ++, intermediate signal; +, weak signal; +/−, triple dropout-resistant yeast clones with barely detectable signal; −, double-dropout resistant clones with no signal; NT, not tested.
[e]This ORF clone (7824017-7824523 bp) likely encodes an unknown protein, because the cDNA insert was derived from mouse eye polyA mRNA. N: nuclear protein.

TABLE 3

Axl-binding proteins.

| Phage clone | Protein name | Accession number | Matched aa residues | Frequency | Binding activity |
|---|---|---|---|---|---|
| ORF matched to protein coding sequence | | | | | |
| PH180 | Lectin, galactose binding, soluble 3 (Lgals3) | NM_010705 | 131Y-264I | 2 | ~1,375X |
| PH181 | SPRY domain containing 3 (Spryd3) | NM_001033277 | 31I-215S | 8 | ~1,000,000X |
| PH194 | Growth arrest specific 6 (Gas6) | NM_019521 | 43Q-148R | 1 | ~40X |
| PH207 | Microfibrillar-associated protein IA or IB (Mfap1) | NM_026220 | 160K-290E | 4 | ~36,667X |
| Non-ORF | | | | 0 | |

All identified Axl-binding phage clones encodes proteins with ORFs. Binding activity is the pfu ratio of clonal phage binding to immobilized Axl-Fc versus blank.

The PS-binding activity of all identified phage clones was analyzed. All identified phage clones exhibited various PS-binding activity, ranging from ~12-fold to ~29,430-fold

TABLE 4

PS-binding proteins.

| Phage Clone | Protein name | Accession number | Matched aa residues | Freq.[a] | Binding specificity[b] PS | PC |
|---|---|---|---|---|---|---|
| ORF matched to protein coding sequence | | | | | | |
| PH166 | Pinin (Pnn) | NM_008891 | 187Q-306E | 1 | ~354X | ~3X |
| PH167 | Vesicle transport through interaction with t-SNAREs 1B homolog (Vti1b) | MM_016800 | 39E-101T | 1 | ~37X | ~1X |
| PH168 | Fibrillarin (Fb1) | NM_007991 | 1M-45G | 1 | ~24X | ~480X |
| PH169 | A kinase (PRKA) anchor protein (gravin) 12 (Akap12) | NM_031185 | 345D-522G | 1 | ~1,067X | ~2X |
| PH183 | RIKEN cDNA 5830404H04 gene (5830404H04Rik) | NM_174847 | 560P-654V | 3 | ~29,430X | ~7X |
| PH184 | Procollagen, type XI, alpha 2 (Col11a2) | NM_009926 | 1354P-1475A | 1 | ~321X | ~6X |
| PH187 | Myosin, light polypeptide kinase (Mylk) | NM_139300 | 1769K-1936G | 1 | ~88X | ~1X |
| PH195 | Serum response factor binding protein 1 (Srfbp1) | NM_026040 | 110V-264E | 1 | ~455X | ~2X |
| PH201 | Serum response factor binding protein 1 (Srfbp1) | NM_026040 | 105A-266S | 1 | ~577X | ~4X |
| PH214 | PRP40 pre-mRNA processing factor 40 homolog A (yeast) (Prpf40a) | NM_018785 | 243E-401K | 1 | ~666X | ~1X |
| PH215 | C2 calcium-dependent domain containing 2-like (C2cd21) | NM_027909 | 467R-694S | 1 | ~725X | ~8X |
| PH216 | RIKEN cDNA 2500003M10 gene (2500003M10Rik) | NM_023215 | 1M-96R | 1 | ~1,367X | ~4X |
| PH218 | RIKEN cDNA 2500003M10 gene (2500003M10Rik) | NM_023215 | 1M-60I | 1 | ~2,976X | ~1X |
| PH217 | A kinase (PRKA) anchor protein 8-like (Akap81) | NM_017476 | 274T-311G | 1 | ~248X | ~7X |
| PH219 | RIKEN cDNA 1200014J11 gene (1200014J11Rik) | NM_025818 | 186K-345E | 1 | ~12X | ~1X |
| Positive control phage displaying full-length MFG-ES | | NM_008594 | | | ~193X | ~8X |
| Non-ORF | | | | 0 | | |

[a]Clone frequency. All identified PS-binding phage clones encodes proteins with ORFs.
[b]Binding specificity is the pfu ratio of clonal phage binding to PS or PC versus to the mock coated wells.

higher binding activity to immobilized PS than to blank well control, whereas the control phage showed no binding activity. Their binding specificity to different phospholipids was also analyzed in a similar manner. All except one clone preferentially bound to immobilized PS, but not to PC. Fibrillarin was the only clone with better binding activity to PC than to PS. The unknown protein (5830404H04Rik) had the highest binding activity and specificity to PS. Consequently, this protein has the potential to be used as a detecting reagent or imaging probe for PS. Further characterization of its binding specificity to different phospholipids and comparison of its PS-binding affinity with other well established PS-detecting reagent, such as annexin V, would be of interest.

to immobilized streptavidin. 3C protease cleavage at 4° C. specifically eluted the phages bound to immobilized streptavidin or bait through the tagged library proteins, but not through other phage surface proteins (FIGS. 1C to 1F). Two flexible GS linkers were designed to improve the accessibility of 3C protease cleavage site, library proteins and biotin tag. 3C protease eluted 80 times more of bound phages than the standard elution method of 1% SDS (FIG. 1E), evidencing that the protease cleavage site is readily accessible in the library.

ORF cDNA libraries were generated based on the fact that non-ORF cDNA has stop codon(s). Database analysis revealed that ~96% of 200-bp non-ORF cDNAs have at least

TABLE 5

Comparison of different technologies for functional proteomics.

|  | ORF Phage Display | Y2H | MS-based approach |
|---|---|---|---|
| Capacity of the technologies | | | |
| Protein-protein interaction | Yes | Yes | Yes |
| Protein-polysaccharide interaction | Yes | No | Yes |
| Protein-lipid interaction | Yes | No | Yes |
| Protein-antibody interaction | Yes | No | Yes |
| Protein-RNA interaction | Yes | No | Yes |
| Proteia-DNA interaction | Yes | Yes[a] | Yes |
| Protein-virus interaction | Yes | No | No[b] |
| Protein-cell interaction | Yes | No | No[b] |
| Protein-tissue interaction | Yes | No | No[b] |
| In vivo selection | Yes | No | No |
| Protease substrate identification | Yes | No[b] | Yes |
| Eat-me signal identification | Yes | No | No |
| Features of the technologies | | | |
| Required time | ~2-7 days[c] | ~1-4 months[b] | ~4-6 days[b,d] |
| Screening scale | ≥$10^{11}$ pfu | ~$10^6$-$10^7$ clones | Entire proteome[b] |
| Sensitivity | Single clone | Single clone | Subfemtomole (~$10^8$ molecules) |
| Re-verification | | | |
| Binding activity | Convenient | Convenient | Difficult[b] |
| Binding specificity | Convenient | Difficult[b] | Difficult[b] |
| cDNA for identified proteins | Available | Available | Not available |
| Instrument requirement | Minimal | Minimal | Demanding |
| Subcloning | Not required | Required | Required[b] |
| Skill required | Minimal | Demanding | Demanding[b] |
| Cost | Minimal | Costly | Costly[b] |

[a]Yeast one-hybrid system.
[b]Open to interpretation.
[c]A fully-automated system of ORF phage display could take as fast as ~2 days to identify unknown bait-binding proteins.
[d]Estimated time for MS-TAP with ectopic gene expression in mammalian cells.

Figure 4:
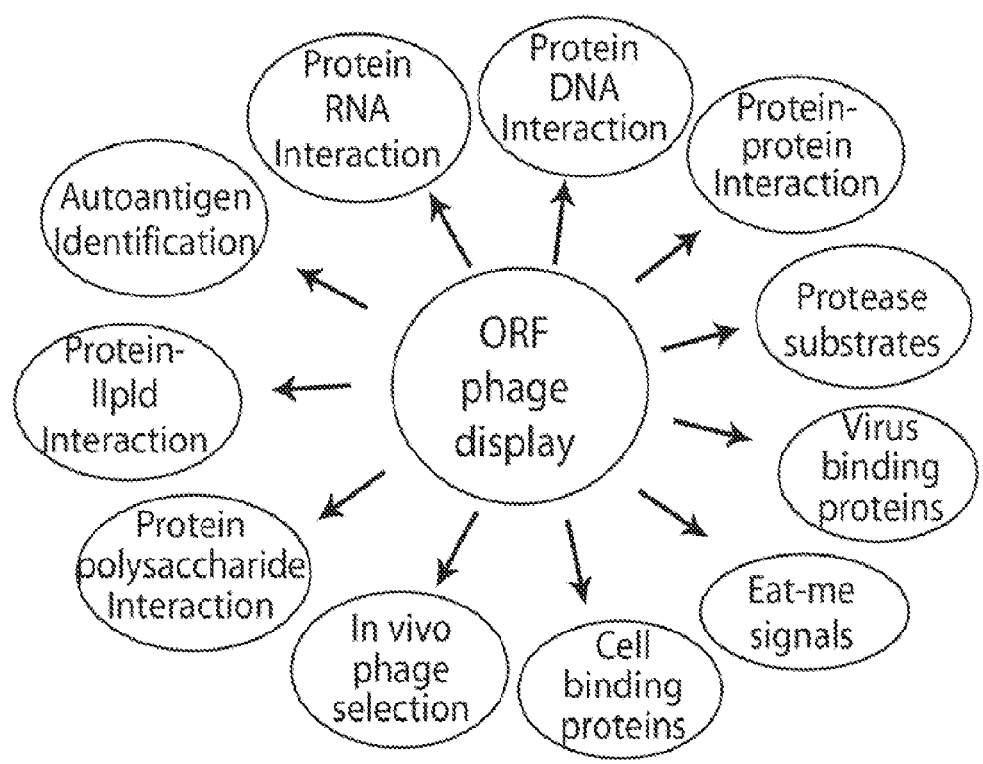
FIG. 4 is a schematic representation showing the versatility of ORF phage display for functional proteomics.

Results:

An ORF phage display was developed with three major breakthroughs: high-quality ORF phage display cDNA libraries, specific elution of bound phages by protease cleavage and dual phage display for high throughput screening. T7 bacteriophage was chosen because of its C-terminal display, robust growth rate, and no requirement for the secretion of displayed proteins. To optimize T7 phage display, a multiple cloning site was engineered in T7Select10-3b phage vector to generate T7Bio3C vector (FIGS. 1A and B). A cleavage motif for human rhinovirus (HRV) 3C protease was fused to the C-terminus of capsid 10B, followed by a GS linker, cloning sites, a second GS linker and a biotinylation tag. A cDNA library was inserted at NotI and XhoI sites. The stop codon at the cloning sites is to prevent the expression of the biotinylation tag in the absence of cDNA insert. The C-terminal biotinylation tag is not expressed unless the cDNA insert is an ORF. Thus, ORF phages, but not non-ORF phages, are biotinylated by E. coli BirA ligase and can be enriched by binding one stop codon. This number drastically increases to 99.6% for non-ORF cDNAs with 300 bp. Two orientation-directed cDNA libraries between 300 bp-1.5 kb were constructed from adult mouse eyes and embryos at day 18 (E18) by the random priming method. Total packaged phage titers were ~$2\times10^7$ pfu for the eye library and ~$1\times10^8$ pfu for the embryo library. Both libraries were amplified once, bound to immobilized streptavidin and eluted by 3C protease cleavage to generate ORF libraries. Size distribution analysis showed that >75% of the cDNA library had inserts longer than 300 bp (FIG. 1G). Immunoblotting assay revealed that >90% of the streptavidin-enriched ORF library had ORF cDNA inserts (FIGS. 4A, 4B). Thus, both libraries are the best size-defined, C-terminal tagged ORF phage display cDNA libraries reported.

Figure 2A:
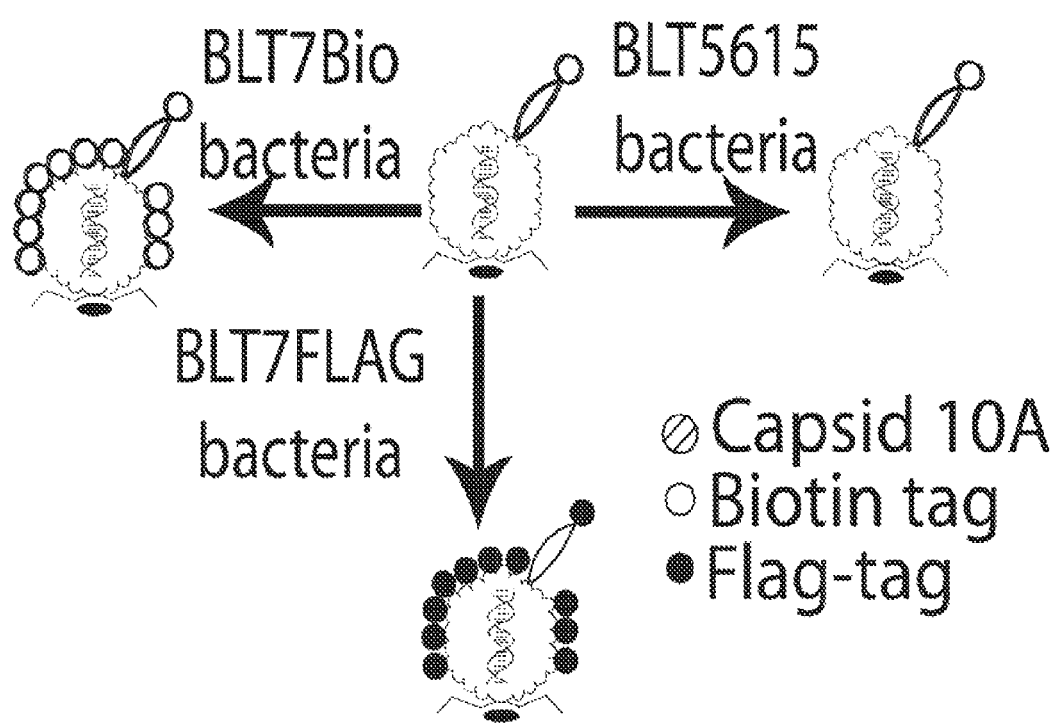
FIG. 2A is a schematic representation showing an embodiment of dual phage display. T7 phages co-display library protein-capsid 10B and capsid 10A with a C-terminal tag, which can be switched by amplifying the phages in different bacterial strains.
Figure 2B:
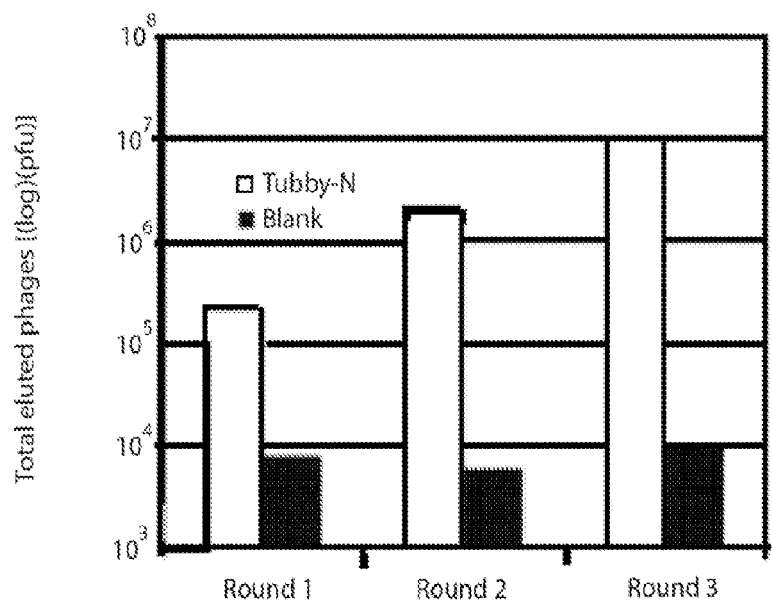
FIG. 2B is a graph showing that Tubby-N-binding phages are enriched by phage panning. The eye library was incubated with immobilized tubby-N, washed, eluted with 3C protease, amplified and used as input for the next round of selection. Phage enrichment was monitored by plaque assay. Blank control was included.
Figure 2C:
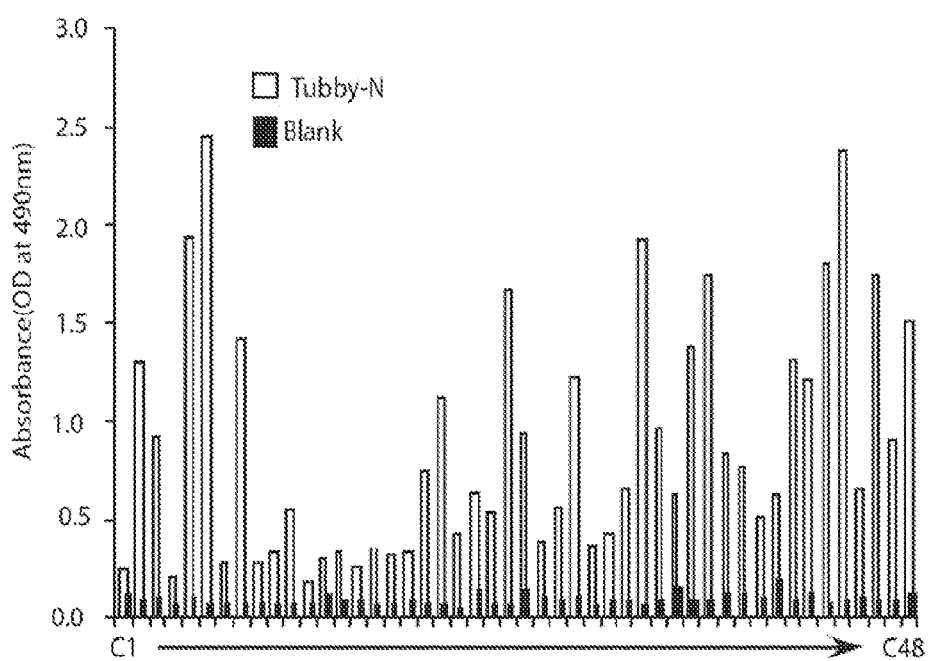
FIG. 2C is a graph showing the results from the screening for tubby-N-binding clones. Individual phage clones at round 3 were analyzed for their binding activities to immobilized tubby-N by colorimetric assay. C4 is a control phage without cDNA insert.
Figure 2D:
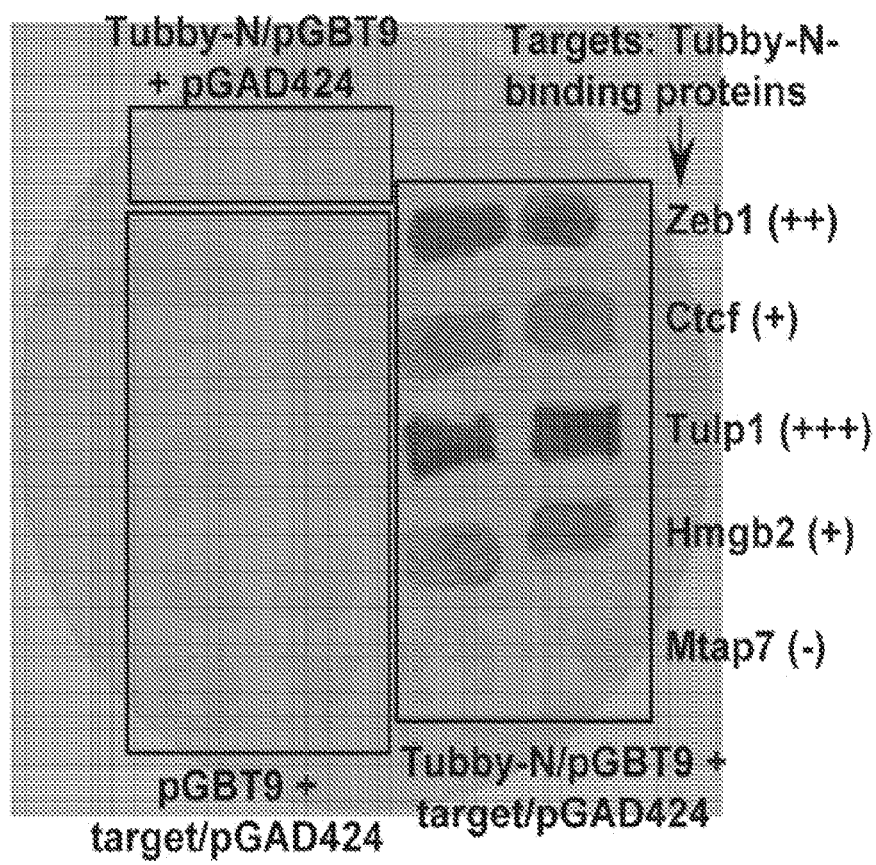
FIG. 2D is a scan of a photograph showing the validation of tubby-N-binding proteins by Y2H assay. Blue color indicated that target proteins interacted with tubby-N.
Figure 5:
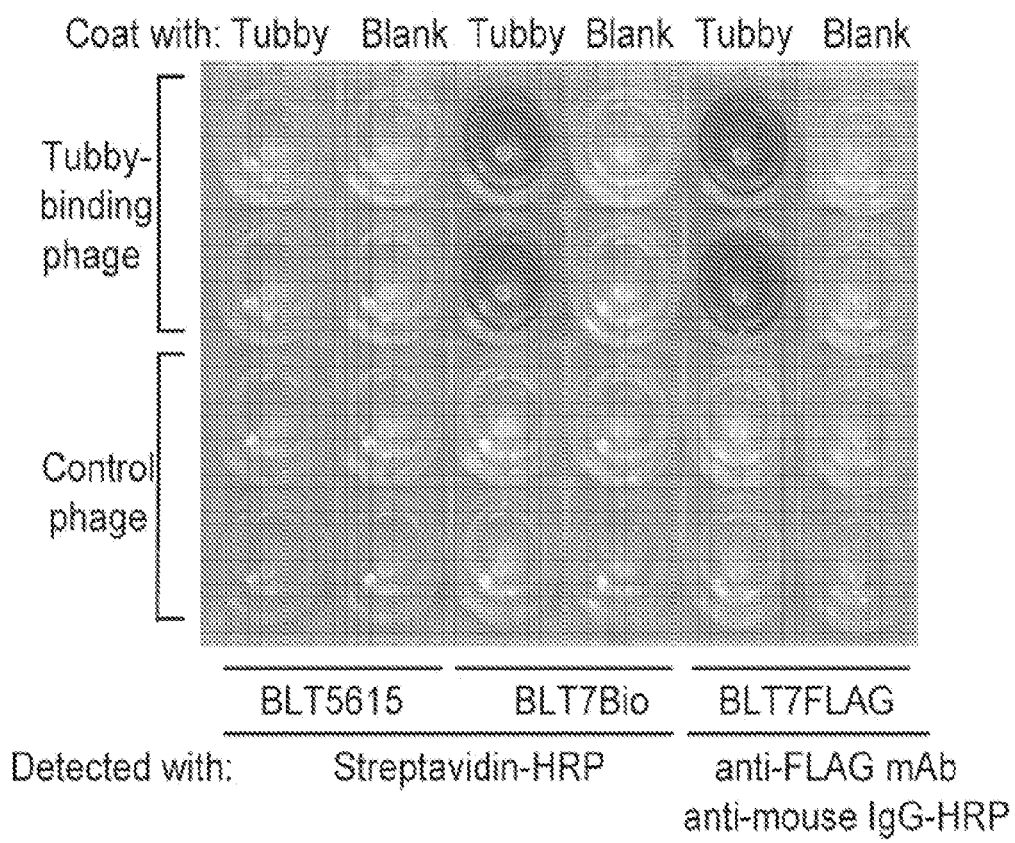
FIG. 5 is a scan of a photograph showing the switching of surface detection moiety in dual phage display. A tubby-N-binding phage clone was amplified in BLT5616, BLT7Bio or BLT7FLAG bacteria and bound to immobilized tubby-N. Bound phages were quantified by colorimetric assay using streptavidin-conjugated HRP or anti-FLAG mAb as indicated.

Unlike filamentous phage, few antibodies are available for quantification of T7 phage. Consequently, T7 phage is traditionally quantified by tedious plaque assays. To improve the efficiency, dual T7 phage display was developed to replace the plaque assays. In addition to the cDNA library displayed at the C-terminus of capsid 10B, a FLAG or a biotinylation tag at the C-terminus of capsid 10A was displayed, which was expressed by newly-engineered BLT7FLAG or BLT7Bio bacterial strain, respectively. With a total of 415 copies of capsid 10A and/or 10B per phage, co-display of ~5-15 copies of capsid 10B-library fusion proteins and >400 copies of FLAG- or biotin-tagged capsid 10A on the same phage surface not only allows the functional analysis of library proteins, but also enables the sensitive quantification of bound phages with enzyme-conjugated streptavidin or anti-FLAG monoclonal Ab (mAb). The surface detection moiety can be conveniently switched by amplifying the same phage in bacterial strains expressing capsid 10A with different C-terminal tags (FIGS. 2A and 5).

Taken together, a high throughput screening system of ORF phage display was developed.

Discussion:

ORF phage display has three major advantages: efficiency, convenience and versatility. First, T7 bacteriophage has a robust growth rate. This substantially reduces the time needed to perform multiple rounds of phage selection and clone screening. The dual phage display technology converts the cumbersome procedure of phage plaque assay into an efficient colorimetric assay for binding analysis of individual clones. 3C protease cleavage further minimizes non-specific phage enrichment. High-quality ORF phage display cDNA libraries are the key to ensure that the majority of identified phage clones encoded real proteins, rather than out-of-frame unnatural polypeptides. The system of ORF phage display integrated with these technical breakthroughs is capable of rapidly identifying unknown bait-binding proteins. Second, the procedures for phage panning and colorimetric binding analysis of individual clones in ORF phage display are similar to ELISA with minimal requirement for skills and instrument. The only skills required are bacterial culture, PCR and ELISA. Thus, this technology can be widely adapted by any laboratory interested in identifying unknown bait-binding proteins as long as the high quality ORF phage display cDNA libraries are available. Moreover, ORF phage display with an ELISA-like procedure can be fully automated for high throughput screening of bait-binding proteins to elucidate global or pathway-specific protein interaction networks or to discover therapeutic protein targets. A fully-automated system could identify bait-binding proteins in as fast as ~2 days. Finally, versatility is a major advantage for ORF phage display. Various applications of phage display technology have been extensively explore: a) protein-protein interaction; b) receptor or ligand identification; c) protein interaction with phospholipids, polysaccharides, DNA or RNA; d) antigen identification; e) protease substrate identification; f) polypeptides capable of stimulating cell internalization; g) cell specific binding polypeptides; h) organ-specific binding polypeptides, etc. However, most of these applications were previously carried out with either antibody library or random peptide library. Consequently, identified antibodies or unnatural short peptides have minimal functional implications in protein biological networks. Some of the studies were performed with regular cDNA libraries with high frequency of non-ORFs. Unlike these previous approaches, however, ORF phage display can efficiently identify real endogenous proteins with specific binding activities or functions, transforming this tool into a powerful technology for functional proteomics.

Comparison of Different Technologies for Functional Proteomics:

Y2H is a popular technology with application restricted only to protein-protein interaction (Table 5). Because of yeast slow growth rate, Y2H usually takes ~1-4 months to screen a library of $10^6$-$10^7$ clones to identify and verify bait-binding proteins. On the other hand, ORF phage display only requires ~2-7 days to identify unknown bait-binding proteins by screening a library of $10^{11}$ pfu. Mass spectrometry coupled with tandem affinity protein purification (MS-TAP) is a powerful technology, but requires expensive equipment. The technology has a limited sensitivity to detect proteins at the sub-femtomole level, and is inconvenient to independently verify protein binding activity. On the contrary, ORF phage display can detect as low as single copies of phage clones because of its capacity for enrichment and amplification. It is quite convenient to re-verify bait-binding activity and specificity of identified phages by phage binding assay. The cDNA inserts in phage clones also come handy for independent validation by other means, including Y2H, co-immunoprecipitation and protein pull-down assays. Compared with Y2H and MS-TAP (Table S3), a major advantage of ORF phage display is the versatility. It can identify not only protein-protein interactions, but also protein interactions with non-protein molecules or even multimolecular baits, including viruses, cells or even tissues. The binding conditions, such as in vivo phage selection, are also more biologically relevant. Thus, ORF phage display is the fastest, most convenient and versatile technology for functional proteomics.

In summary, compared with other technologies, ORF phage display is a versatile technology, applicable not only to protein bait, but also to non-protein baits, including lipid, polysaccharide, antibody, DNA, RNA, and other molecules. ORF phage display with multimolecular baits, such as viruses, cells or even tissues or organs in in vitro or in vivo settings, should be able to isolate biologically relevant endogenous proteins like viral receptors, and cell- or tissue-specific ligands. Proteins with specific functions, including eat-me signals and substrate degradomes of proteases, could also be elucidated by ORF phage display. ORF phage display can efficiently identify real endogenous proteins with functional implications. Nearly all identified phage clones in this study with multiple baits match to protein coding sequences. Moreover, ORF phage display with a straightforward ELISA-like procedure can be conveniently adapted by individual laboratories with minimal experience in bacteria culture and PCR, or fully automated for high throughput screening to elucidate biological networks and therapeutic protein targets in as fast as ~2 days. Furthermore, many bait molecules, such as PS and Axl-Fc, are already commercially-available. Thus, this technology is the fastest, most convenient and versatile technology for functional proteomics with the potential for far-reaching impact on our understanding of protein biological networks, disease mechanisms and drug discovery.

Example 3

Functional Cloning of Eat-Me Signals

Materials and Methods

Cell lines and culture conditions: ARPE19, a human retinal pigment epithelium (RPE) cell line (ATCC, Manassa, Va.), was cultured in Dulbecco's modified essential medium (DMEM)/F-12 (1:1) medium supplemented with 10% fetal bovine serum (FBS), 2 mM L-glutamine and 0.28% $NaHCO_2$. Human D407 RPE cell line, was cultured in DMEM supplemented with 10% FBS and 2 mM L-glutamine. Rat RPE-J RPE cell line was cultured at 33° C. in DMEM supplemented with 4% FBS, 4 mM L-glutamine, 0.1 mM non-essential amino acids and 0.15% $NaHCO_2$. Mouse primary RPE cells were isolated from postnatal day 10 mice, and cultured in DMEM supplemented with 10% FBS, 2.5 mM L-glutamine and 0.1 mM non-essential amino acids. Neuro-2a cells were cultured in DMEM medium supplemented with 10% FBS and 2 mM L-glutamine.

Phage Selection:

Open-reading-frame (ORF) phage display cDNA library was constructed from mouse eye. Phage selection by RPE phagocytosis was performed with the following modifications. Briefly, the library (~1×10$^{11}$ pfu) was precipitated with polyethylene glycol (PEG 8000) according to the protocol described in "T7Selection System Manual" by Novagen (Madison, Wis.) (available at www.emdbiosciences.com/docs/docs/PROT/TB178.pdf). Precipitated phages were resuspended in the ice-cold complete medium, added to pre-chilled ARPE19 cells, and incubated at 4° C. for 30 min with gentle shaking. The cells were washed with ice-cold phosphate buffered saline (PBS) to remove unbound phages, followed by incubation in the complete medium at 37° C. for 30 min to allow phagocytosis to occur. Unphagocytosed surface-bound phages were removed by incubating in the stripping buffer (100 mM glycine, pH 2.5, 150 mM NaCl, 200 mM urea, 2 mg/ml polyvinylpyrrolidone) at room temperature for 2 min×2. The cells remained morphologically intact under a light microscope. Phagocytosed phages were released by adding the lysis buffer (1 mM triethylamine, 0.5% Triton X-100) for 30 sec with pipetting and immediately neutralized to pH ~7.4. A small aliquot of the cell lysate was quantified by plaque assay to determine total phagocytosed phages. The phages in the remaining cell lysate were amplified in BLT5615 bacteria, precipitated and used as input for the next round of selection. As a quality control, our recent data showed that the stripping efficiency of surface-bound phage was >99.98%.

After four rounds of selection, enriched phages were selected twice with immobilized streptavidin as follows. Briefly, ELISA plates (Corning Life Science, Lowell, Mass.; 8-well strip, #2592) were coated with streptavidin (10 µg/ml in PBS, 100 µl/well) at 4° C. overnight, blocked with 1% bovine serum albumin (BSA) in PBST (PBS plus 0.1% Tween-20), incubated with 100 µl of phage lysates for 1 h, and washed with PBST for 6 min×6. With a unique design of the phage library (see co-submitted manuscript), bound phages were eluted with human rhinovirus (HRV) 3C protease (2 units in 100 µl of PBS) (Novagen) at 4° C. for 1 h, and plated on BLT5615 bacterial plates. Individual phage plaques were isolated, amplified, precipitated and re-analyzed in their stimulation of ARPE19 cell phagocytosis. The cDNA inserts encoded putative "eat-me" signals were amplified by PCR with T7SelectUp and T7SelectDown primers (Novagen) and identified by DNA sequencing.

```
T7SelectUp primer:           (SEQ ID NO: 49)
5'-GGA GCT GTC GTA TTC CAG TC-3'

T7SelectDown Primer:         (SEQ ID NO: 50)
5'-AAC CCC TCA AGA CCC GTT TA-3'.
```

Plasmid Construction:

All full-length Tulps were generated from mouse eye or testis by reverse transcription-PCR (RT-PCR). The cDNA for mouse tubby IVS11+1G→T mutation with extra 22-aa residues to replace its C-terminal 44 aa was generated by PCR using overlapping primers. The sequence derived from human Tulp1 Intron 14 was generated by PCR for the mutation of IVS14+1G→A or IVS14-6C→A. These DNA fragments were fused to truncated tubby (Asp461) or Tulp1 (Asp498) by PCR with overlapping primers. Other missense mutations in human Tulp1 were generated by PCR using overlapping primers with mutations embedded in primers appropriately. The coding region of minimal phagocytosis determinant (MPD)-null Tulp1 was optimized at cDNA level to improve PCR efficiency, but its protein sequence was not altered except at the designated amino acid residues for KKK to AAA mutations. All full-length Tulps and their mutants with deletion or missense mutation were subcloned into pcDNA3 (Invitrogen, Carlsbad, Calif.) with an N-terminal FLAG tag. All plasmids were verified by DNA sequencing. All FLAG-Tulps in pcDNA3 were additionally verified by Western blot using anti-FLAG M2 monoclonal antibody (mAb).

Membrane-targeting epitope derived from protein GAP-43 was generated by PCR with overlapping primers, digested with BglII and BamHI, and fused to green fluorescent protein (GFP) N-terminus in pEGFP-N1 plasmid (Clontech, Mountain View, Calif.) at BamHI site to yield membrane-targeted GFP plasmid. Membrane-targeted mCherry plasmid was generated by replacing GFP with mCherry in the plasmid. GFP-FLAG was generated by fusing FLAG tag to the C-terminus of GFP in pEGFP-N1 plasmid using a PCR strategy with overlapping primers.

Clonal Phage Construction:

All full-length Tulps (tubby, Tulp1, 2 and 3) and their mutants with deletion or missense mutations were generated by PCR and ligated into T7Bio3C vector at NotI and XhoI sites. Control phage had no cDNA insert. All phage clones were verified by DNA sequencing.

Phage Phagocytosis Assay:

The procedure to analyze the phagocytosis of individual phage clones was the same as the phage selection procedure, except that clonal phages, instead of the heterogeneous phage library, were used in the assay. The data were normalized and expressed as phagocytosis index, which is the pfu ratio of (total phagocytosed clonal phage)/(total phagocytosed control phage).

Figure 8A:
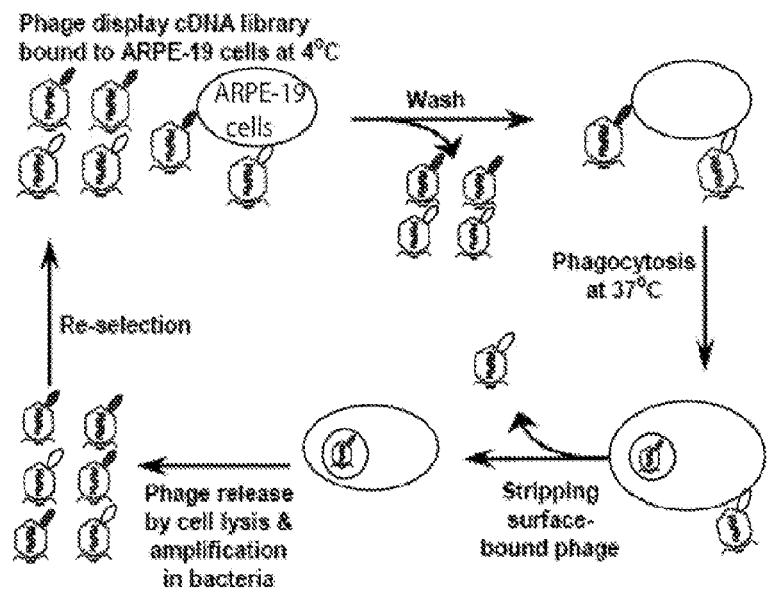
FIG. 8A is a schematic representation showing the identification of eat-me signals by ORF phage display. ARPE19 cells were incubated with the library, washed and phagocytosed at 37° C. After stripping, internalized phages were released by cell lysis, amplified and used as input for the next round of selection.
Figure 8B:
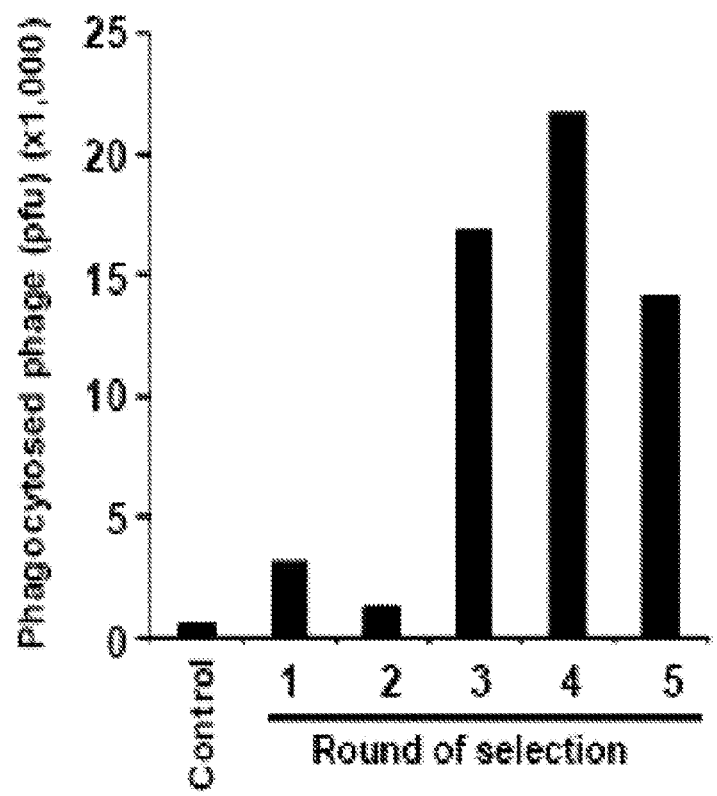
FIG. 8B is a graph showing phage enrichment monitored by plaque assay and PCR.
Figure 8C:
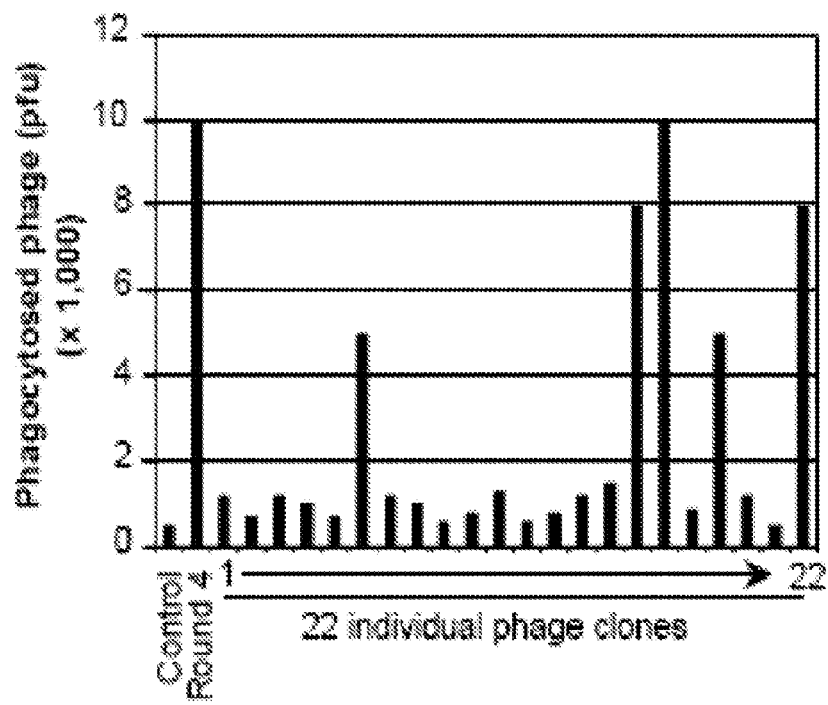
FIG. 8C is a graph showing an analysis of individual clones by phage phagocytosis assay in ARPE19 cells. Only the first 22 phage clones are shown. Control phage has no cDNA insert.

Membrane Vesicle Phagocytosis Assay:

Neuro-2a cells were used to prepare membrane vesicles with FLAG-tagged Tulps, because Neuro-2a cells express no detectable endogenous tubby or Tulp1 by 35-cycle RT-PCR with tubby- or Tulp1-specific primers. Briefly, Neuro-2a cells at 80% confluence in 150 mm plates were co-transfected with two plasmids, membrane-targeted GFP (or mCherry) plasmid (13 µg) and eat-me signal-expressing plasmid (26 µg), by calcium phosphate method. The plasma membrane was prepared at 48 h post-transfection by sucrose gradient centrifugation. Briefly, co-transfected cells were scraped off from the culture plates, homogenized and purified by sucrose gradient centrifugation at 105,000 g for 1 h. Plasma membrane vesicles at the interface of 20% and 27% sucrose were collected, washed twice with PBS, resuspended in PBS with 2.5% sucrose, added to ARPE19 cells in 2-chamber slides (Nunc, Rochester, N.Y.) (50 µg membrane protein/ml/chamber), incubated at 37° C. for 3 h, washed, and incubated at 37° C. for additional 15 h in the 293 SFM II medium (Invitrogen) for phagocytosis. The studies in the complete medium yielded similar results, and the low level of serum tubby (FIG. 11D) had minimal effect on the assays with appropriate controls. Minimal degradation of membrane vesicles during the incubation was revealed by the similar level of FLAG-tagged tubby or Tulp1 protein on the recovered unphagocytosed GFP-positive membrane from 37° C. vs. 4° C. incubation. After washing, phagocytosed fluorescent membrane vesicles were analyzed by Leica TCS SP5 confocal microscopy with diode laser for excitation at 405 nm and emission at 480 nm for 4',6-diamidino-2-phenylindole (DAPI), argon laser excitation at 488 and emission at 510-570 nm for GFP, and HeNe laser excitation at 543 nm and emission at 600-680 nm for mCherry. Nuclei were counterstained with DAPI (1 µg/ml). All data for fluorescence-labeled phagocytosis were derived from the middle sections of ARPE19 cells by confocal microscopy with DAPI staining. However, DAPI signals were not shown in most of the figures, because DAPI blue signals significantly compromised visual perception of GFP signals as shown in FIG. 8C (iii vs. vi).

Microbead Phagocytosis Assay:

All Tulps were subcloned into pGEX-2T plasmid (GE Healthcare, Piscataway, N.J.) and expressed in BL21 (DE3) bacteria as glutathione S-transferase (GST) fusion proteins. While GST-Tulp1 and GST-Tulp2 were minimally expressed in cell lysates due to possible formation of inclusion body, GST-tubby, GST-Tulp3 and GST control were well expressed by the induction with isopropyl β-D-1-thiogalactopyranoside (IPTG) (1 mM), purified using glutathione columns (Pierce, Rockford, Ill.), and verified by SDS-PAGE. After dialysis, purified proteins were conjugated to carboxylate-modified yellow-green fluorescent microspheres (2 µm in diameter) (Invitrogen) according to the manufacturer's protocol. Ligand-conjugated microbeads (~300 µg beads with ~15 µg conjugated protein) were added to ARPE19 cells (~$1.5 \times 10^5$ cells) in the chamber slides, incubated at 37° C. for 3 h, washed and incubated at 37° C. for additional 15 h for phagocytosis, as described above. After washing, phagocytosed microbeads were analyzed by confocal microscopy, as described above.

Tubby and Tulp1 Knockout Mice:

C57BL/6 mice and the breeder pair of tubby knockout mice on the same genetic background were purchased from the Jackson Laboratory (Bar Harbor, Me.). Tulp1$^{-/-}$ mice were from The Jackson Laboratory. Genotyping was carried out by PCR using gene-specific primers. All neonatal mice were raised in the dark to slowdown photoreceptor degeneration in homozygotes. Eyes were enucleated from euthanized homozygous mice at postnatal day 19. Retinas were collected and homogenized for the preparation of membrane vesicles as described above. Purified membrane vesicles were labeled with 5(6)-carboxyfluorescein diacetate N-succinimidyl ester (CFSE) (Sigma, St. Louis, Mo.). Briefly, membrane proteins (~50 µg/ml PBS) were labeled with 0.5 pM CFSE for 10 min at 37° C. After washing, the labeled membrane vesicles were analyzed for phagocytosis in RPE cells as described above in the presence or absence of 10 µg/ml of the indicated FLAG-tagged recombinant proteins. Recombinant adenoviruses expressing FLAG-tagged recombinant tubby, Tulp1 and GFP were constructed as previously described (S. Santagata et al., Science 292, 2041 (2001)). The recombinant proteins were purified with an anti-FLAG mAb affinity column (Sigma), eluted with FLAG peptide (Sigma) and dialyzed against PBS.

Mer-Fc Binding to Immobilized Membrane Vesicles:

Membrane vesicles (10 µg protein/ml) prepared from Neuro-2a cells expressing Tulps were immobilized on ELISA plates at 4° C. overnight, blocked with 1% BSA in PBS, incubated with Mer-Fc (50 ng/ml) (R&D systems, Minneapolis, Minn.). After washing, bound Mer-Fc was detected by biotin-conjugated goat anti-human IgG, followed by streptavidin-conjugated horseradish peroxidase (HRP). Bound HRP was visualized with 100 µl of substrate containing o-phenylenediamine (OPD) (0.4 mg/ml) and H2O2 (0.01%) in citric acid buffer (20 mM citric acid, 40 mM $NaH_2PO_4$, pH5.0), stopped with 100 µl of 1 M $H_2SO_4$ and quantified with a plate reader at 490 nm.

Mer Autophosphorylation:

D407 cells were cultured in 293 SFM II medium for 2 h to reduce the background of Mer activation, followed by incubation with membrane vesicles expressing different Tulps or pcDNA3 control vesicles in the same medium for 30 min at 37° C. Gas6 (50 nM) (R&D Systems) was used as a positive control. After washing, the cells were directly lysed and analyzed by Western blot. The immunoblots were probed with primary Abs against phospho-Mer (Fabgennix, Frisco, Tex.), Mer (R&D system) or RPE65 (Novus Biologicals, Littleton, Colo.), followed with appropriate HRP-labeled secondary antibodies. The signals were revealed by chemiluminescence detection.

Blood Tubby:

Anti-tubby (T-19) antibody (Santa Cruz Biotechnology, Santa Cruz, Calif.) or control rabbit antibody (200 µg/ml, 1 ml) was covalently conjugated to Affi-Gel Hz hydrazide gel (Bio-Rad, Hercules, Calif.) according to the manufacturer's protocol and packaged into a mini column. Human sera (2.5 ml per column) were isolated from fresh blood of healthy donors, and passed through anti-tubby antibody affinity column or control antibody column twice. After washing, bound proteins were eluted with 0.1 M glycine (pH 2.7), immediately neutralized to pH 7.4, and analyzed by Western blot using the anti-tubby antibody.

Figure 17:
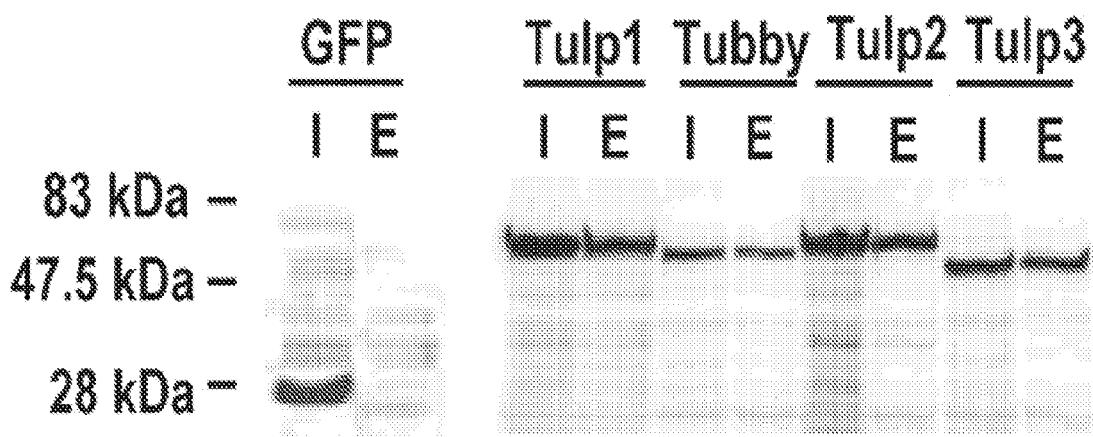
FIG. 17 is a blot showing the intracellular and extracellular expression of tubby and Tulp1. Neuro-2a cells were transfected with plasmids expressing indicated FLAG-tagged Tulps. The conditioned serum-free medium of transfected cells was collected, as described in Materials and Methods. Intracellular (I) and extracellular (E) FLAG-Tulps were analyzed by Western blot using anti-FLAG mAb. I: lysate of ~4×10$^4$ cells per sample; E: concentrated cell-free medium from ~2×10$^5$ cells during a period of 24 h. GFP-FLAG was a negative control.

Extracellular Expression of Tulps:

To analyze intracellular and extracellular expression of Tulps, Neuro-2a cells were transfected with plasmids expressing FLAG-tagged Tulps, collected at 48 h post-transfection, and analyzed for intracellular expression of Tulps by Western blot using anti-FLAG mAb (FIG. 17). For extracellular expression analysis, transfected Neuro-2a cells were cultured in the complete medium for 24 h, washed and switched to 293 SFM II medium. The medium was collected twice at 36 h and 48 h post-transfection, concentrated with spin-filter concentrator units (Pierce) (9 kDa MW cut-off), and analyzed by Western blot. FLAG-GFP was included as a negative control.

Co-Immunoprecipitation:

Neuro-2a cells were transfected with plasmids expressing FLAG-tagged Tulps or pcDNA3. Cells were collected 48 h post-transfection and lysed with PBS containing 0.5% Triton X-100. After removal of the cellular debris by centrifugation, the lysates were incubated for 1 h with Mer-Fc at 4° C., followed by protein G resin (Sigma). The resin was washed and analyzed by Western blot using anti-FLAG mAb to detect FLAG-tagged Tulps.

Protein Pull-Down Assay:

Neuro-2a cells were transfected with plasmids expressing FLAG-tagged Tulps. Cell lysates were prepared as described above, incubated with purified GST-tubby for 1 h, followed by glutathione resin. The resin was washed and analyzed by Western blot using anti-FLAG mAb.

Statistical Analysis:

All experiments were repeated at least 3 times. All results are expressed as mean±SEM. One-way analysis of variance followed by Post-hoc Tukey-Kramer pairwise comparisons was used to determine statistical significance among different groups.

Results:

Photoreceptor outer segments (POS) in the retina convert light into electrical impulses but are susceptible to photo-oxidative damage. As part of the repair process, photoreceptors shed damaged POS at the tip of the outer segments in a diurnal rhythm. Retinal pigment epithelium (RPE) cells underneath photoreceptors play a pivotal role in POS regeneration by ingesting and recycling shed POS vesicles through phagocytosis. With the turnover rate of 10 days for the entire POS, each RPE cell is required to phagocytose a large amount of shed POS, equivalent to ~5,000-fold of its own volume in a lifespan. The importance of RPE phagocytosis is further implicated by a phagocytic receptor of Mer receptor tyrosine kinase (RTK), whose mutations cause defective RPE phagocytosis that leads to retinal degeneration (RD) in Royal College of Surgeons (RCS) rats and in patients. However, "eat-me" signals or "phagocytosis stimulating molecules" controlling the initiation of RPE phagocytosis are poorly defined. In contrast to phosphatidylserine (PS) as a well-characterized eat-me signal, much less is known about protein ligands, which are traditionally identified on a case-by-case basis with daunting challenges. A few characterized eat-me signals in RPE phagocytosis, including growth arrest-specific gene 6 (Gas6) and milk fat globule epidermal growth factor 8 (MFG-E8), were all identified in other professional phagocytes like macrophages. In-depth understanding of RPE phagocytosis was heretofore hindered by inefficient elucidation of unknown eat-me signals and cognate receptors.

The open-reading-frame (ORF) phage display system developed here is the fastest technology to identify protein-protein interaction in ~2-7 days (see infra). ORF phage display is a versatile technology, not only for protein-protein interaction, but also for protein interaction with non-protein molecules or multimolecular baits such as like viruses, cells or tissues. To facilitate the understanding of phagocyte biology, an unbiased identification of unknown eat-me signals was performed in RPE cells by ORF phage display, as depicted in FIGS. 8A to 8C and FIG. 12.

Figure 8D:
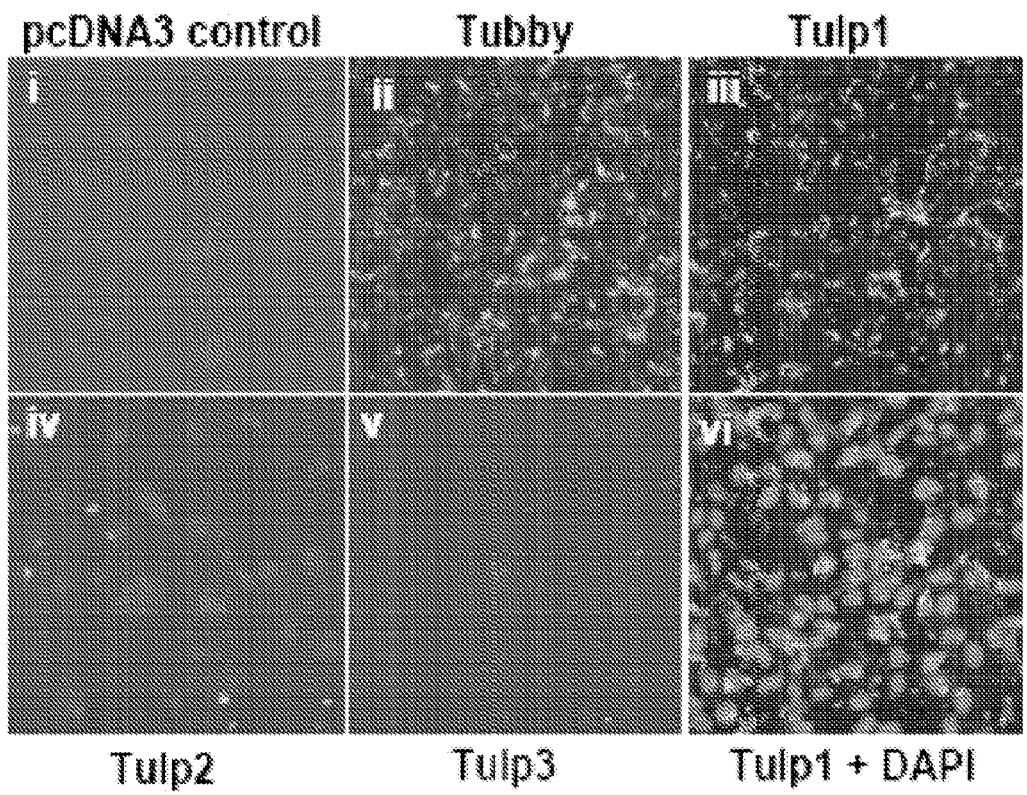
FIG. 8D is a scan of a photograph showing the stimulation of RPE phagocytosis by Tulps. GFP-labeled membrane vesicles were prepared from Neuro-2a cells expressing Tulps, and incubated with ARPE19 cells. Phagocytosed fluorescent signals were analyzed by confocal microscopy. vi is identical to iii but with DAPI nuclear staining. For better visual perception, DAPI signals are not shown in all other figures.
Figure 8E:
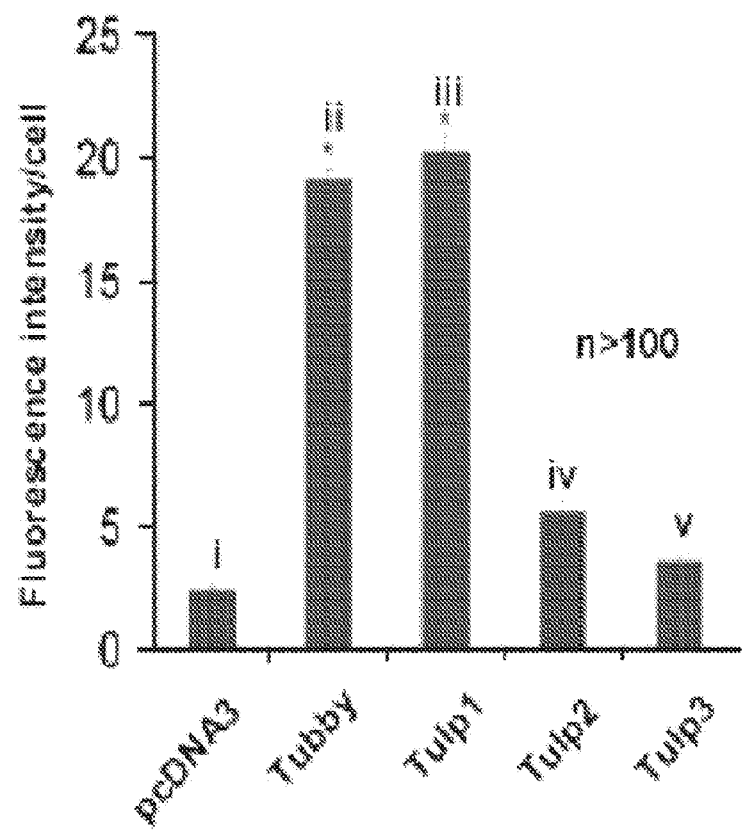
FIG. 8E is a graph showing the relative fluorescence intensity per cell in FIG. 8D was quantified in >100 cells per group (±SEM; *p<0.001; vs. pcDNA3; Tukey-Kramer test).
Figure 14A:
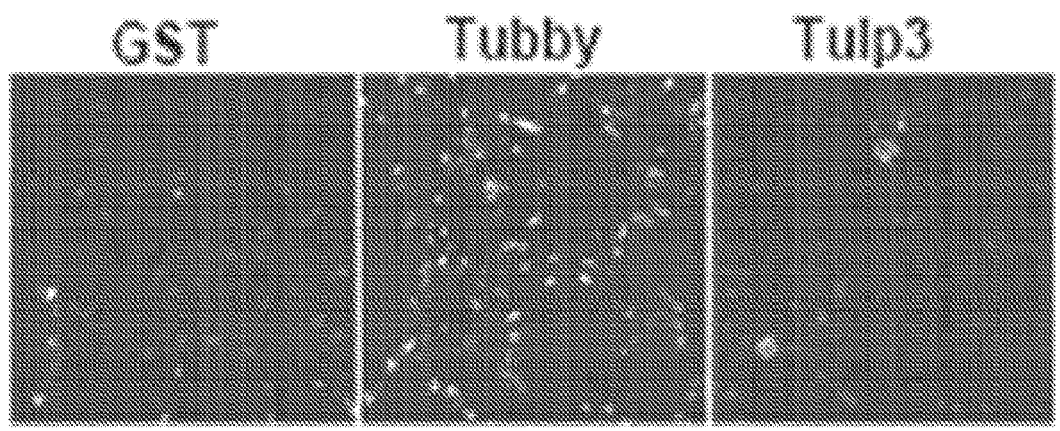
FIGS. 14A and 14B show Tubby-conjugated fluorescent microbeads stimulate RPE phagocytosis. GST-tubby, GST-Tulp3 and GST control were expressed in *E. coli*, purified with glutathione columns, covalently conjugated to fluorescent microbeads, and analyzed for their phagocytosis in ARPE19 cells.

A total of 9 putative eat-me signals were identified by 4 rounds of selection from an ORF phage display cDNA library of mouse eye, including Gas6, tubby-like protein 1 (Tulp1) and SPRY domain containing 3 (Spryd3) (Table 6). Identification of Gas6, a well-characterized ligand for the TAM RTK subfamily of Tyro3, Axl and Mer in macrophage and RPE phagocytosis, substantiated the functional cloning strategy for unbiased discovery of endogenous eat-me signals. The feasibility of this cloning strategy was further supported by the experiments using a phage clone displaying MFG-E8. Coincidental finding of Spryd3 as an Axl-binding protein in an unbiased screening by ORF phage display implicates that Spryd3 may stimulate RPE phagocytosis through Axl RTK. Nonetheless, Tulp1 was chosen for further characterization because of its role in RD.

dently verify these findings, a membrane vesicle-based phagocytosis assay was developed. Instead of preparing POS vesicles from the retina, membrane vesicles were prepared from Neuro-2a cells, which have no detectable expression of endogenous tubby or Tulp1 by RT-PCR. Green fluorescent protein (GFP)-labeled plasma membrane vesicles prepared from Tulp1-transfected Neuro-2a cells (Tulp1-vesicles) triggered robust phagocytosis in RPE cells (FIGS. 8D and 8E). Similarly, tubby-vesicles, but not Tulp2- or Tulp3-vesicles, also induced vigorous phagocytosis. Furthermore, full-length Tulps was expressed as glutathione S-transferase (GST) fusion proteins in E. coli. Only GST-tubby and GST-Tulp3 were successfully expressed, purified and covalently conjugated to fluorescent microbeads. The conjugated GST-tubby, but not GST-Tulp3 or GST control, facilitated microbead uptake by RPE cells (FIGS. 14A, B).

Figure 8F:
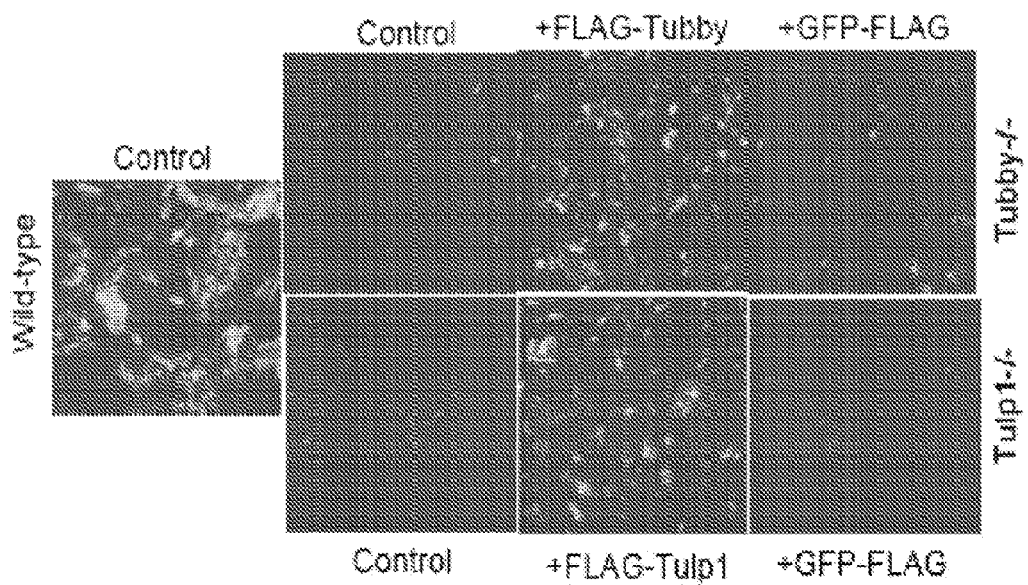
FIG. 8F is a scan of a photograph showing reduced RPE phagocytosis for tubby$^{-/-}$ or Tulp1$^{-/-}$ membrane vesicles. Membrane vesicles were prepared from mouse retinas of wild-type, Tulp1$^{-/-}$ or tubby mice at postnatal day 19, labeled with 5(6)-carboxyfluorescein diacetate N-succinimidyl ester (CFSE), analyzed for RPE phagocytosis as in (D) in the presence or absence of purified FLAG-tagged tubby, Tulp1 and GFP.

The roles of tubby and Tulp1 in RPE phagocytosis were further supported by the significant reduction in the phagocytosis of fluorescence-labeled membrane vesicles prepared from the retina of tubby$^{-/-}$ and Tulp1$^{-/-}$ mice (FIG. 8F). Purified recombinant tubby or Tulp1 substantially compensated the reduction (FIG. 8F), evidencing that both proteins are essential for RPE phagocytosis.

Figure 9A:
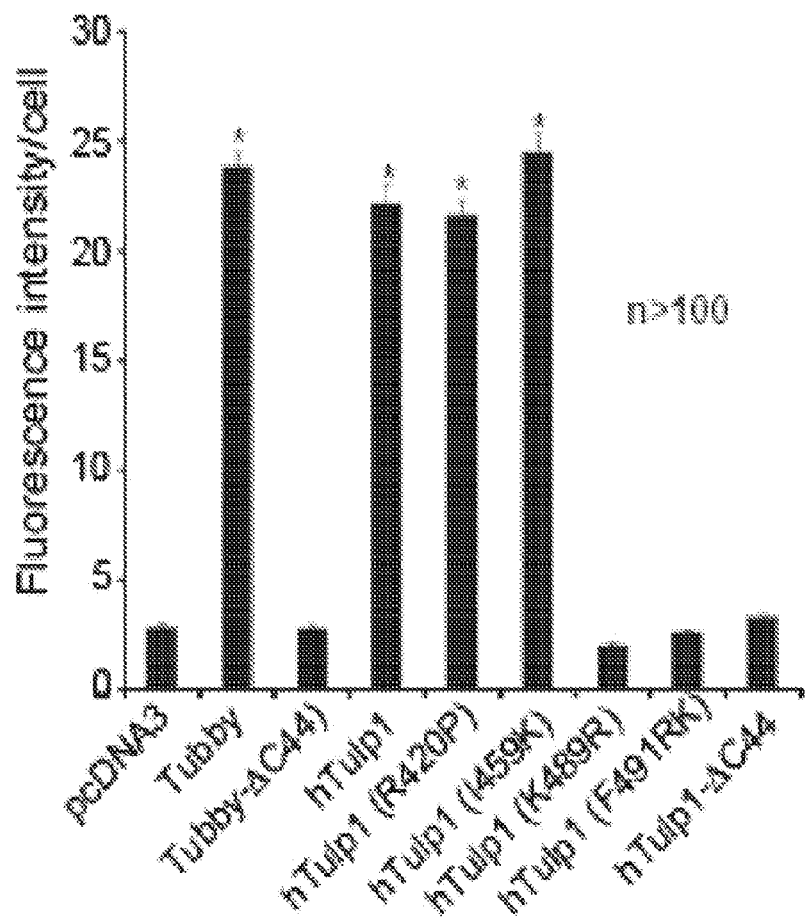
FIG. 9A is a graph showing that C-terminal mutations of tubby and Tulp1 abolish their stimulation of RPE phagocytosis. Membrane vesicles were prepared from Neuro-2a cells expressing wild-type or mutant tubby or Tulp1 (Tubby-like protein 1), analyzed for their phagocytosis in RPE cells and quantified as in FIGS. 8D and E. (±SEM; *p<0.001; vs. pcDNA3; throughout).

Tubby mice develop RD due to a IVS11+1G→T mutation in the tubby gene, which leads to mRNA alternative splicing and replacement of the C-terminal 44-amino acid (aa) chain with a 22-aa polypeptide derived from Intron 11 (Tubby-ΔC44). The IVS14+1G→A mutation in human Tulp1 (hTulp1), presumably affecting mRNA splicing by deleting the C-terminal 44 aa in a similar fashion (Tulp1-ΔC44 with 499P-542E deletion), is also associated with RD. cDNA sequences were constructed mimicking these mutations. Both mutants failed to stimulate RPE phagocytosis (FIG. 9A). Moreover, a possible correlation between Tulp1-induced RPE phagocytosis and RD was indicated by the pathogenic missense mutation of K489R or F491L in hTulp1 that abolished its stimulation of RPE phagocytosis (FIG. 9A). These findings seemingly contradict the previously-reported intracellular functions of tubby and Tulp1. However, a molecule may have multiple functional roles both intracellularly and extracellularly. One example is PS that serves both as a cofactor for intracellular signaling cascades in healthy cells and as an eat-me signal on the surface of apoptotic cells. The putative pathogenic mutations of R420P and I459K in

TABLE 6

Identified putative eat-me signals for RPE phagocytosis.

| Phage clone | Protein name | Accession number | Matched aa residues | Phagocytosis index |
|---|---|---|---|---|
| PH013 | ATP-binding cassette, sub-family F (GCN20), member 1 (Abcf1) | NM_013854 | 29K-176G | ~46X |
| PH019 | Lyl antibody reactive clone (LyAR) | NM_025281 | 100Q-220R | ~25X |
| PH054 | Tubby-like protein 1 (Tulp1) | NM_021478 | 79A-199T | ~22X |
| PH140 | Max protein (Max) | NM_008558 | 35R-154K | ~31X |
| PH137 | Predicted gene, EG666160 (EG666160) | XR_033995 | 575L-701P | ~25X |
| PH138 | UPF3 regulator of nonsense transcripts homolog A (Upf3a) | NM_025924 | 173P-257E | ~22X |
| PH213 | Growth arrest specific 6 (Gas6) | NM_039455 | 43Q-143D | ~14X |
| PH227 | Coiled-coil domain containing 55 (Ccdc55) | NM_001012309 | 223E-365E | ~11X |
| PH228 | SPRY domain containing 3 (Spryd3) | NM_001033277 | 31I-215S | ~15X |

Phagocytosis index = (total phagocytosed clonal phage)/(total phagocytosed control phage).

Figure 13B:
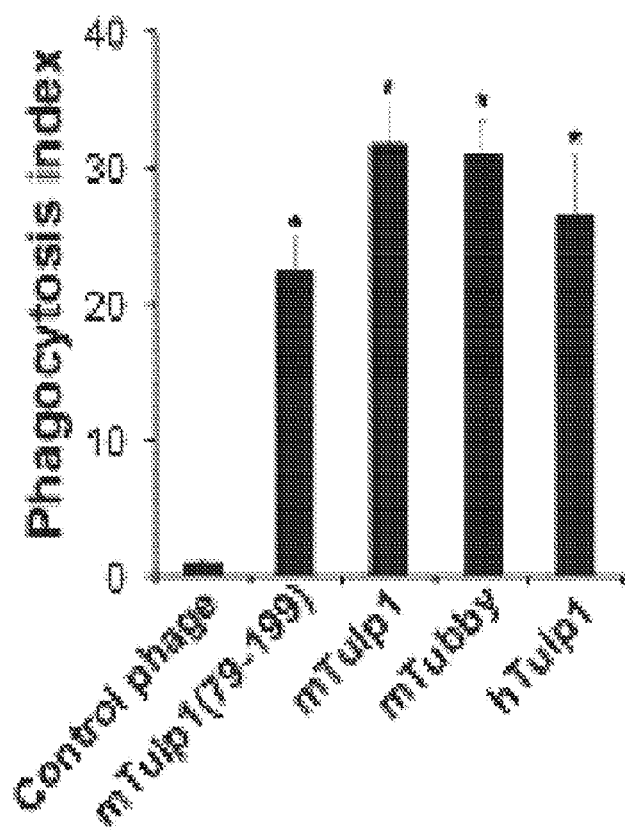

The results showed that Tulp1 induced phagocytosis in all three RPE cell lines and primary RPE cells tested, but not in epithelium cell lines derived from other tissues (FIG. 13A). Similar to Tulp1, a phage clone expressing full-length tubby also stimulated RPE phagocytosis (FIG. 13B). To independently hTulp1 had no effect on RPE phagocytosis (FIG. 9A), implicating that Tulp1 may play additional roles in the maintenance of photoreceptors.

Figure 9B:
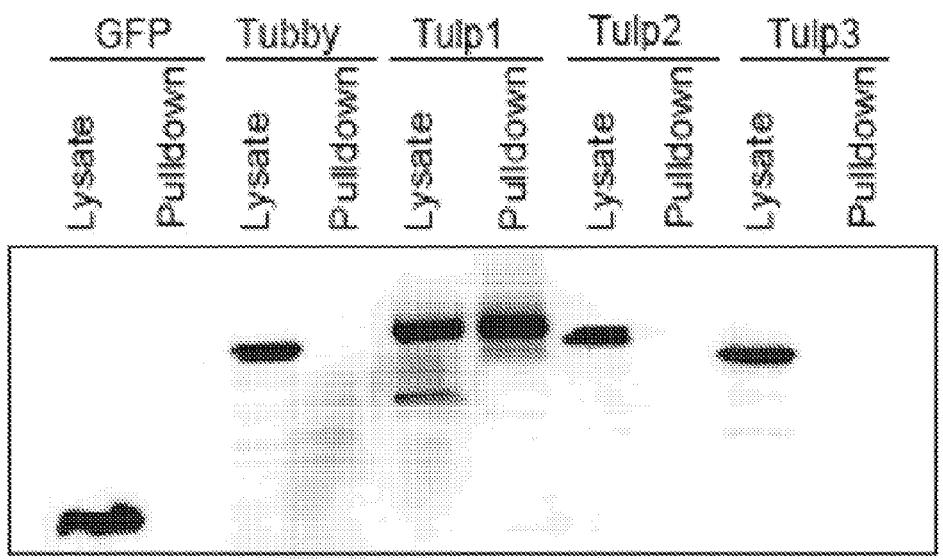
FIG. 9B is a blot showing that Tubby specifically interacts with Tulp1. GST-tubby was incubated with the cell lysates of FLAG-tagged Tulps or GFP, pull-downed with glutathione resin, analyzed by Western blot using anti-FLAG mAb.
Figure 9C:
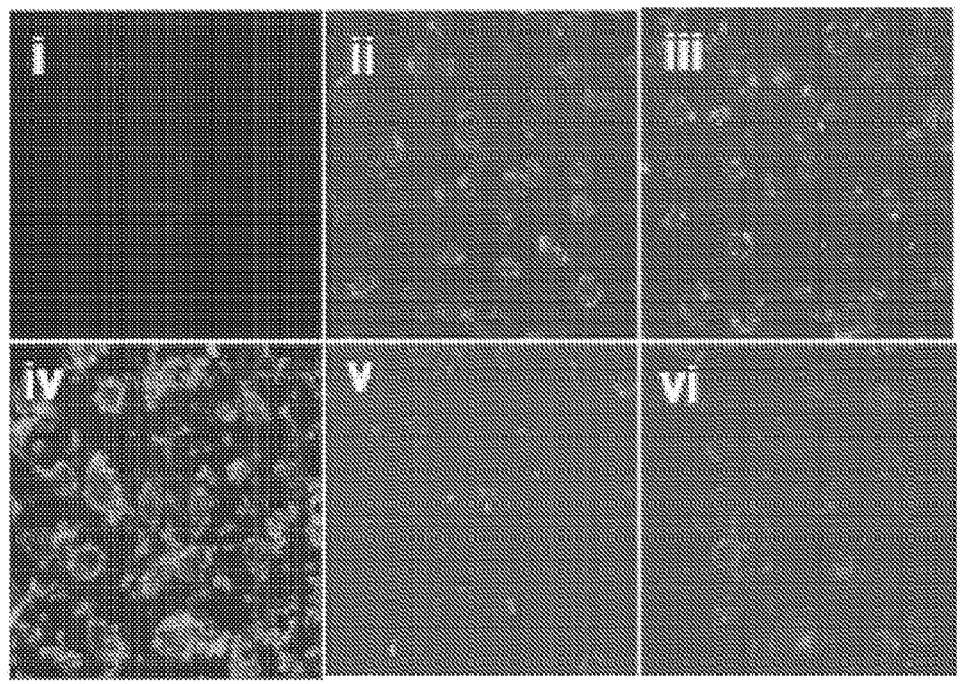
FIGS. 9C and 9D show Tubby and Tulp1 synergistically stimulate RPE phagocytosis. Mixture of indicated membrane vesicles expressing tubby, Tulp1 or their mutants were analyzed for RPE phagocytosis and quantified as in FIGS. 8D and E. Total amount of vesicles in each group was the same (*p<0.001; iv vs. ii; all others vs. i).
Figure 9D:
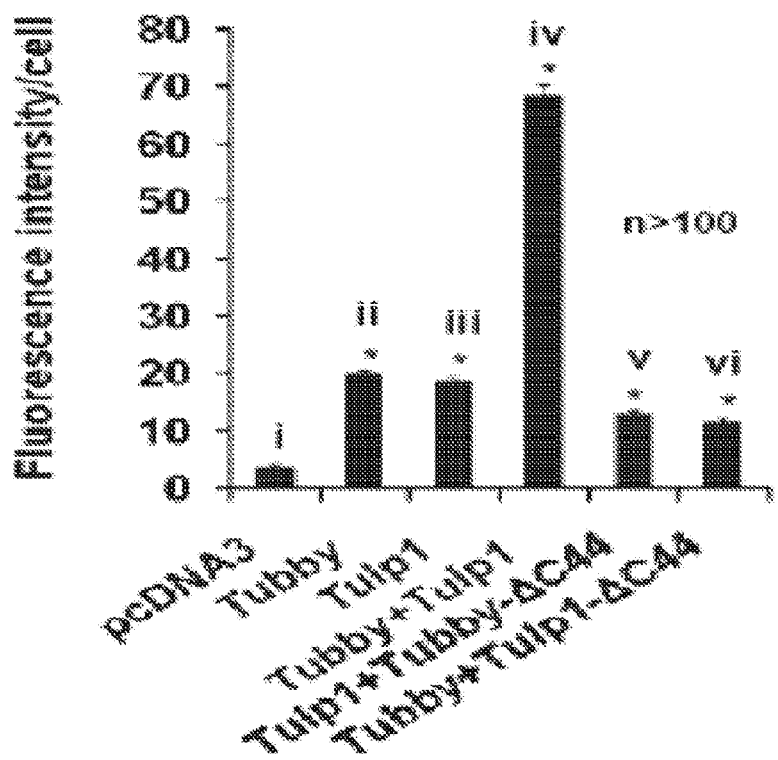
Figure 9E:
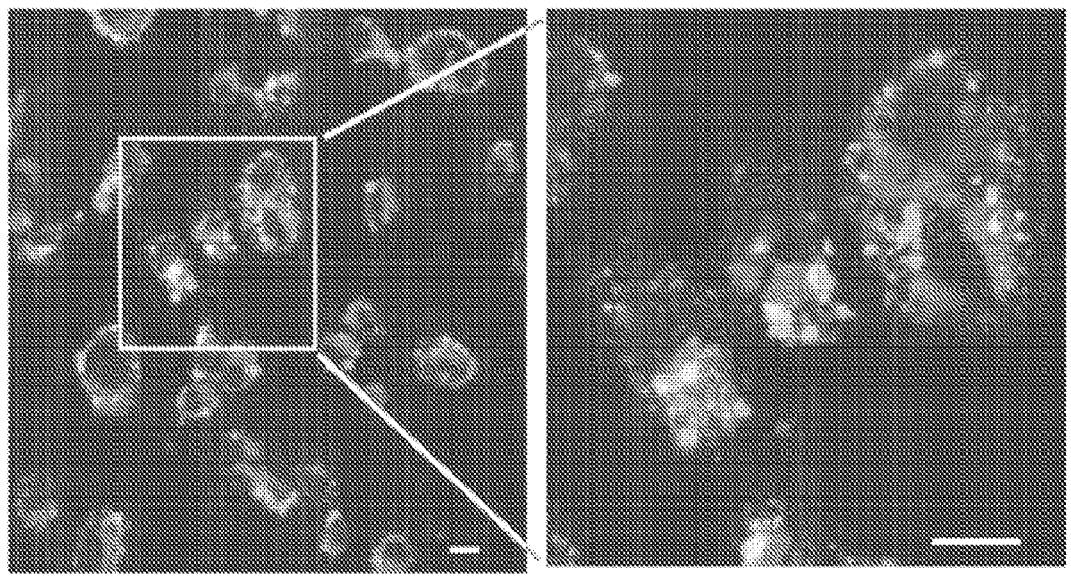
FIG. 9E is a scan of a photograph showing that GFP-labeled Tulp1-vesicles and mCherry-labeled tubby-vesicles are phagocytosed by the same RPE cells. Space bar=5 µm.

To elucidate intracellular and extracellular functions of the tubby family, 15 new tubby-binding proteins were identified by ORF phage display. Among them were 8 nuclear proteins, indicating that tubby broadly interacts with intracellular protein networks. A surprising finding in Example 2 by the ORF phage display was the identification of Tulp1 as a tubby-binding protein. Tubby-Tulp1 interaction was further confirmed by yeast two-hybrid system and protein pull-down assay (FIG. 9B), indicating that Tulp1 and tubby form a heterodimer or heterooligomer. Their interaction was also functionally revealed by their synergistic stimulation of RPE phagocytosis by mixing two membrane vesicles expressing individual proteins (FIGS. 9C and 9D). Mixture of Tulp1-vesicles and tubby-vesicles labeled with green and red fluorescent proteins, respectively, showed that both vesicles were phagocytosed by the same phagocytes (FIG. 9E). Furthermore, the mutant tubby failed to synergistically facilitate Tulp1-mediated phagocytosis, and vice versa (FIG. 2, v and vi in C and D). These data may explain why functionally redundant tubby and Tulp1 failed to compensate for each other in autosomal recessive RD.

Figure 10A:
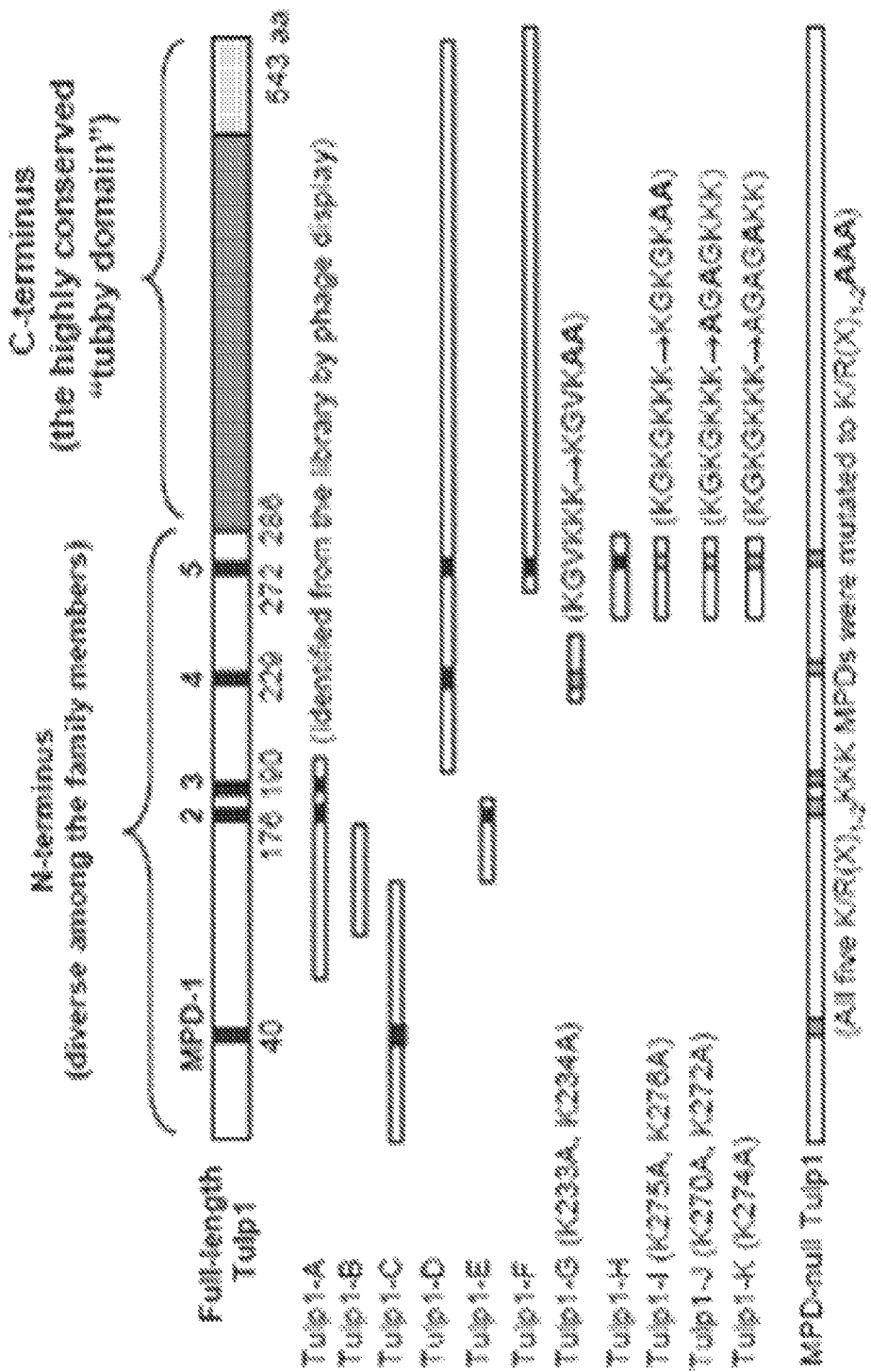
FIG. 10A is a schematic representation showing the structure of mouse Tulp1 and its mutant constructs. Different phage clones were constructed to express Tulp1 N-terminus with deletions or mutations as indicated. MPD, minimal phagocytosis determinant.
Figure 10B:
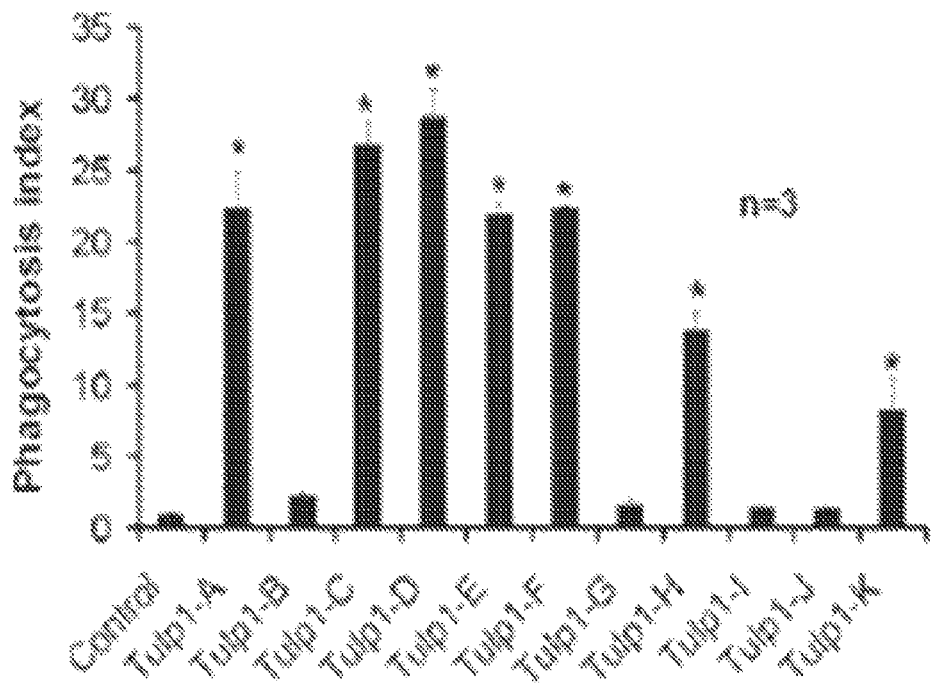
FIG. 10B is a graph showing mutant phage clones that were analyzed for RPE phagocytosis as described in FIG. 8C (±SEM; *p<0.001 vs. control).
Figure 10C:
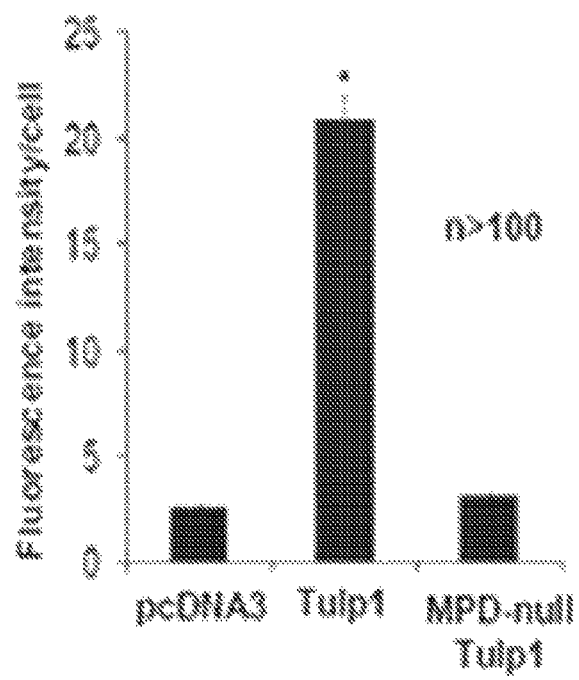
FIG. 10C is a graph showing that MPD-null Tulp1 fails to stimulate RPE phagocytosis. MPD-null-Tulp1 with all five K/R(X)$_{1-2}$ KKK MPDs mutated to K/R(X)$_{1-2}$AAA was analyzed for RPE phagocytosis as in FIGS. 8D and E. (±SEM; *p<0.001; vs. pcDNA3).

The question was then asked why tubby and Tulp1, but not Tulp2 and Tulp3, facilitate phagocytosis, even though all Tulps have a highly conserved C-terminal region essential for tubby and Tulp1 to stimulate RPE phagocytosis. It was hypothesized that the divergent N-termini of tubby and Tulp1 may have additional "phagocytosis determinant(s)" absent in Tulp2 and Tulp3. A series of phage clones were constructed, expressing Tulp1 N-terminus with deletions or mutations and analyzed their stimulatory activities (FIGS. 10A and B). The results led to predicting five "minimal phagocytosis determinants" (MPDs) of $K/R(X)_{1-2}KKK$ in the N-terminus. This prediction was ultimately validated by drastic reduction in the stimulatory activity of MPD-null Tulp1, in which all five MPDs were mutated to $K/R(X)_{1-2}AAA$ (FIG. 10C). Sequence analysis revealed that tubby has one MPD, whereas Tulp2 and Tulp3 have none, a pattern that matches their stimulatory activity profiles.

Figure 11A:
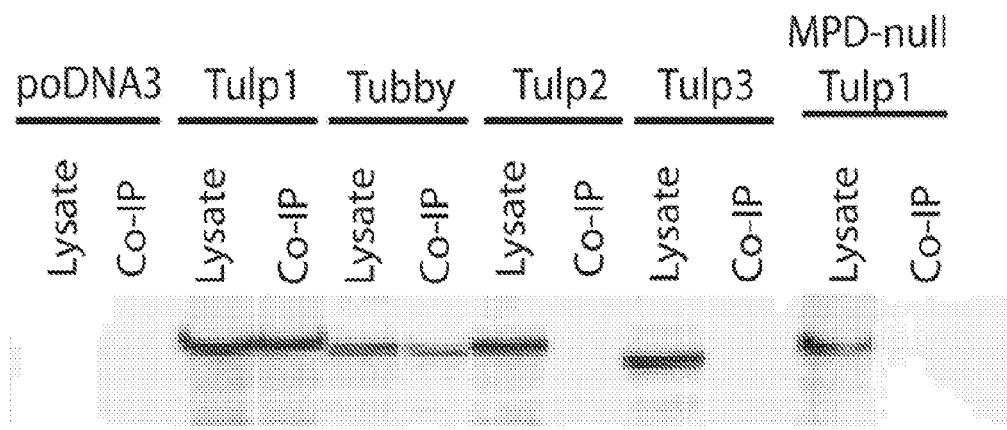
FIGS. 11A-11F show that Tubby and Tulp1 binds to common Mer receptor.
Figure 11B:
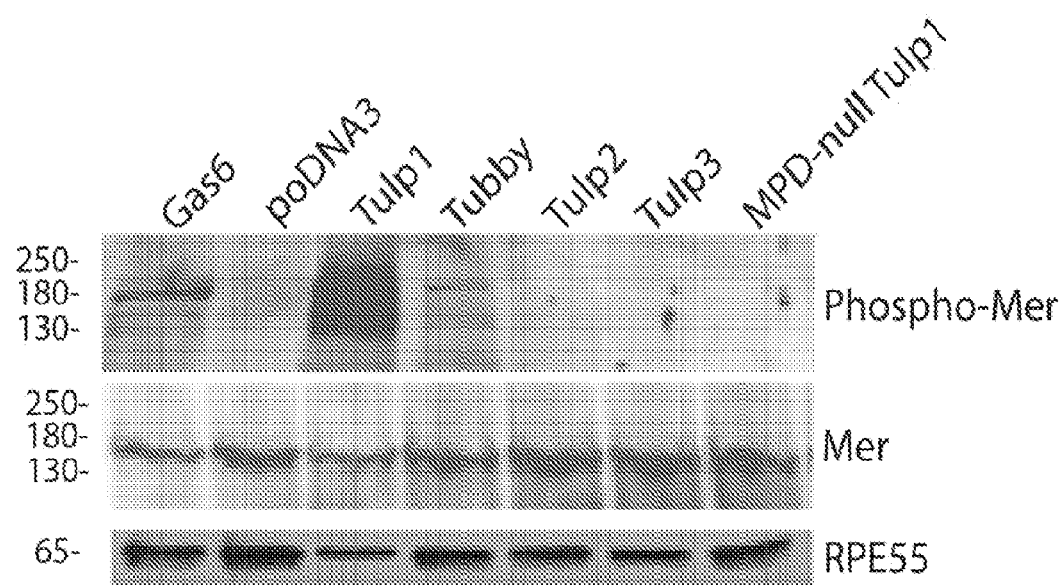
Figure 11C:
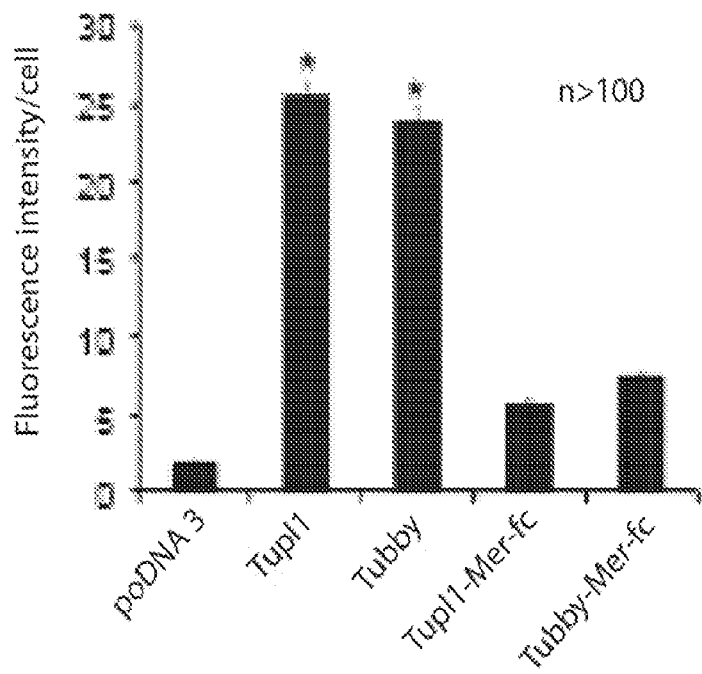
Figure 15A:
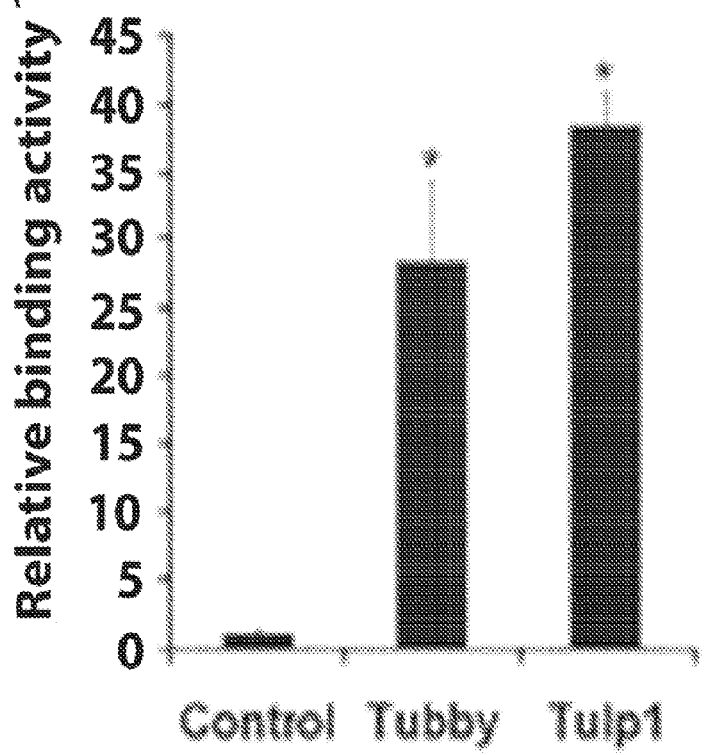
FIGS. 15A and 15B are graphs showing that Mer is a common phagocytic receptor for tubby and Tulp1.
Figure 15B:
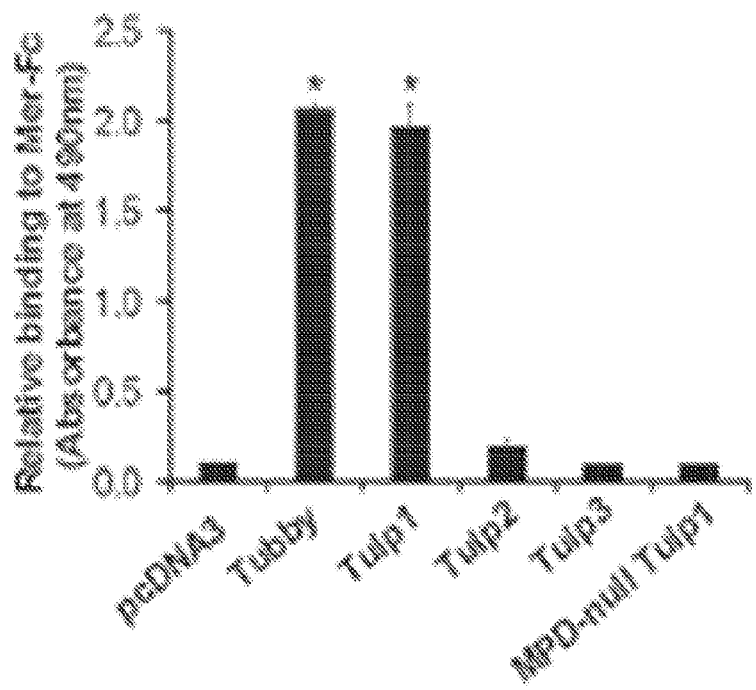
Figure 16:
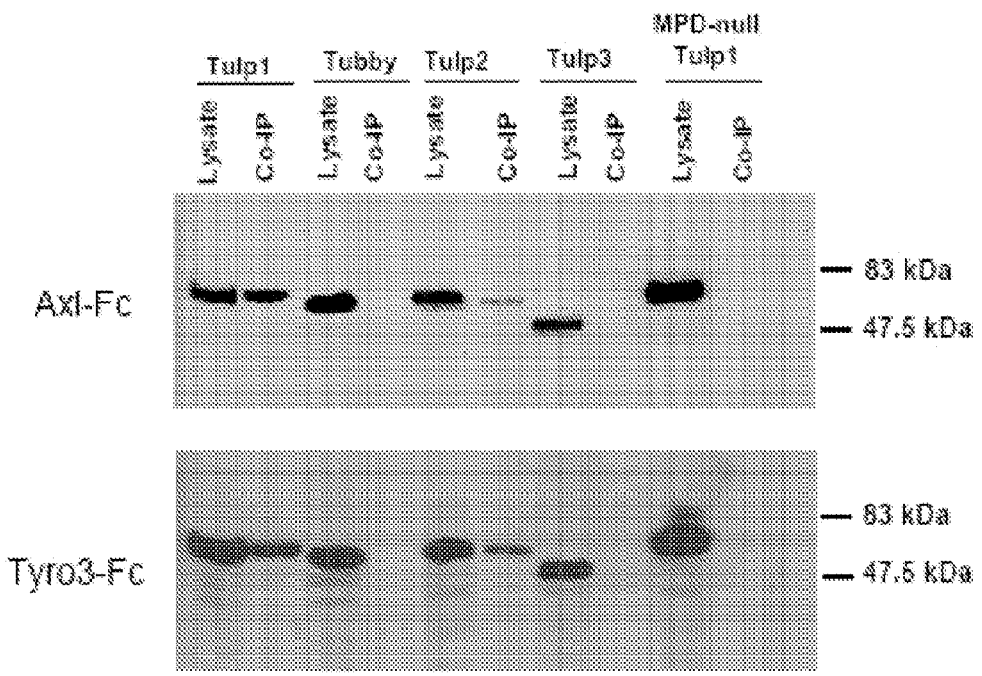
FIG. 16 is a blot showing the receptor binding specificity of tubby and Tulp1. The binding specificity of FLAG-tagged Tulps or MPD-null Tulp1 to Axl and Tyro3 were analyzed by co-immunoprecipitation. Neuro-2a cells were transfected with plasmids expressing indicated FLAG-tagged Tulps. Cell lysates were prepared 48 h post-transfection, incubated with Axl-Fc or Tyro3-Fc, and precipitated with protein G resin. After washing, the resin was analyzed by Western blot using anti-FLAG mAb. Together with the data in FIG. 11A, these results evidence that Tulp1 binds to Mer, Axl and Tyro3, whereas tubby only binds to Mer.

An important step toward understanding the functions of ligands is to study their receptors. Mer was identified as a common receptor for tubby and Tulp1 with multiple lines of evidence. First, tubby-Phage and Tulp1-Phage bound to immobilized Mer-Fc (Mer extracellular domain fused to human IgG1 Fc fragment) (FIG. 15A). Second, Mer-Fc bound to immobilized membrane vesicles expressing tubby or Tulp1, but not Tulp2, Tulp3 or MPD-null Tulp1 (FIG. 15B). Third, co-immunoprecipitation confirmed Mer-Fc interaction with tubby and Tulp1, but not Tulp2, Tulp3 and MPD-null Tulp1 (FIG. 11A). Fourth, tubby and Tulp1, but not Tulp2, Tulp3 and MPD-null Tulp1, activated the receptor, leading to Mer auto-phosphorylation (FIG. 11B). Tulp1 with five MPDs elicited more robust Mer phosphorylation than tubby with single MPD, possibly due to more efficient receptor homodimer and/or heterodimer formation by binding to the RTKs in the same subfamily (FIG. 16). Finally, preincubation of Mer-Fc with tubby-vesicles or Tulp1-vesicles blocked RPE phagocytosis (FIG. 11C). These data evidence that Mer is a common receptor for tubby and Tulp1. The role of Mer as an RPE phagocytic receptor and its mutations associated with RD further support tubby and Tulp1 as eat-me signals for RPE phagocytosis. Moreover, the failure of MPD-null Tulp1 to bind to Mer and to induce RPE phagocytosis (FIG. 10C and FIGS. 11A to C) indicates that the MPDs represent new Mer-binding motifs. The inability of binding to PS and lack of conventional Mer-binding globular laminin G-like (LG) domains indicate that tubby and Tulp1 are a new type of ligand for Mer-mediated phagocytosis. However, similar to Gas6 and protein S, Tulp1 and tubby have different binding specificities to the RTKs in TAM subfamily. Tulp1 bound to Tyro3, Axl and Mer, whereas tubby only bound to Mer (FIGS. 11A and 16).

Figure 11D:
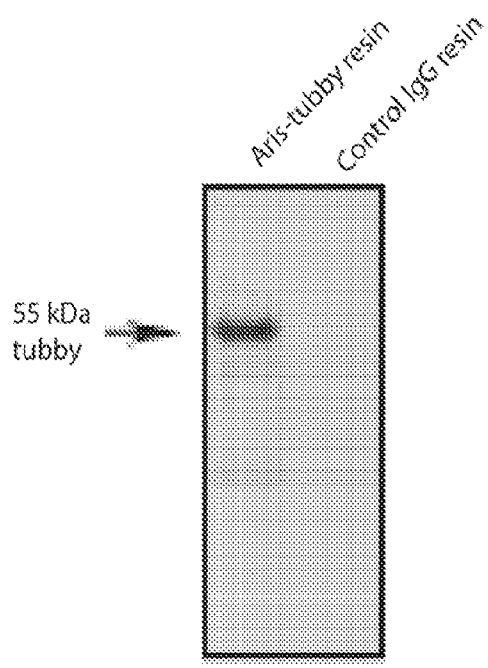
Figure 11E:
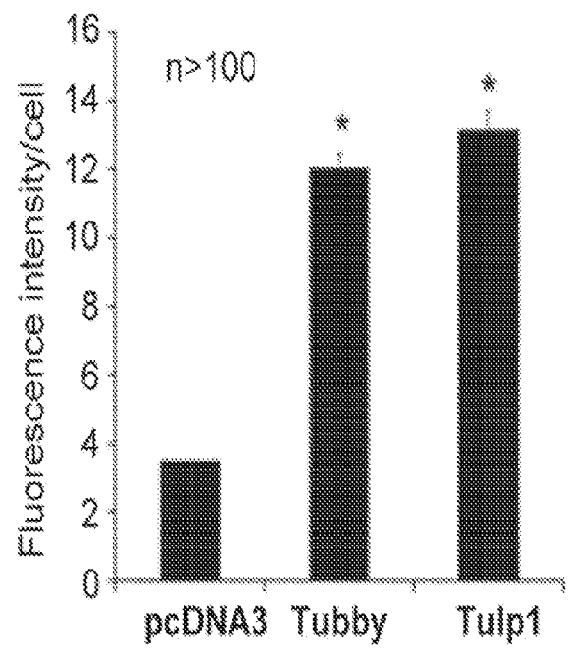

Finally, it was asked whether tubby and Tulp1 have physiological access to the RPE cell surface. Although both proteins with no signal peptide were apparently detected in photoreceptors by immunohistochemistry, the results revealed that all Tulps were expressed both intracellularly and extracellularly (FIG. 17). In contrast, GFP mock control was exclusively expressed intracellularly. Their extracellular trafficking was further supported by the presence of tubby in human serum (FIG. 11D). Moreover, extracellular tubby and Tulp1 that were collected from the culture medium, when pre-incubated with control membrane vesicles followed by washing, facilitated RPE phagocytosis (FIG. 11E). These data indicate that tubby and Tulp1 have physiological access to the RPE cell surface in vivo. Both proteins likely function as bridging molecules, similar to Gas6 and MFG-E8, by simultaneously binding to the target membrane vesicles and Mer on RPE cells. In light of tubby stimulation of macrophage phagocytosis (FIG. 18), circulating tubby may play a much broader role in regulating the function of other phagocytes.

Figure 11F:
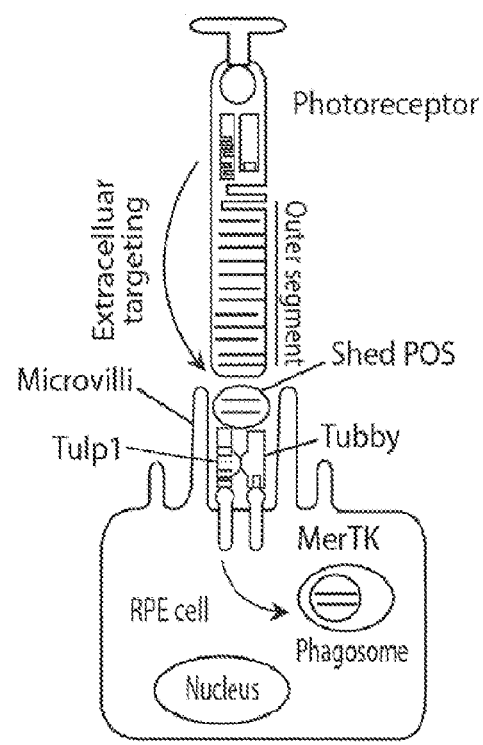

Taken together, it is proposed that tubby and Tulp1 not only are expressed intracellularly to interact with cytoplasmic or nuclear protein networks, but also are exported to the extracellular space. Extracellular tubby and Tulp1 recognize Mer receptor on RPE cell surface, and are capable of facilitating RPE phagocytosis in synergy by forming a heterodimer (FIG. 11F). The failure of mutant tubby or Tulp1 to synergistically stimulate phagocytosis may explain the lack of compensation between the two functionally redundant proteins in autosomal recessive RD. Moreover, the intracellular functions of tubby and Tulp1, potentially mediated by the intracellular tubby-binding proteins, could also be important to the maintenance of photoreceptors.

One of the major breakthroughs in this study is the functional cloning strategy for unbiased identification of unknown eat-me signals. Phagocytosis is critical for many physiological and pathological processes, ranging from morphogenesis and cell homeostasis to the immune response and tissue repair. Eat-me signals hold a key to our understanding of phagocyte biology. The previous approach of chemically-induced random genetic mutations in C. elegans is only capable of identifying signaling molecules, rather than eat-me signals per se. In addition to the technical challenges and lengthy procedures, the previous methods were not applicable to other animals that are not transparent for live screening of accumulated cell corpses by optics microscopy. By exploiting the functional nature of phagocytes, ORF phage display is capable of identifying putative eat-me signals even in the absence of other probes, specific reagents or information about phagocytic receptors. This strategy is broadly applicable to professional and non-professional phagocytes, such as macrophages, microglia, RPE cells and Sertoli cells, and will stimulate the field of phagocyte biology with newly-identified eat-me signals as keys to open more doors to the field.

Feasibility of the Functional Cloning Strategy:

In general, phagocytosis arbitrarily refers to internalization of large particles (>200 nm), whereas pinocytosis refers to internalization of smaller particles or cell surface-bound ligands or molecules through different mechanisms. For example, the molecular mechanism of pinocytosis induced by epidermal growth factor (EGF) binding to EGF receptor (EGF-R) on non-phagocytes is very different than those of PS-, Gas6-, or MFG-E8-mediated phagocytosis in phagocytes. Internalization of EGF-expressing phage by binding to EGF-R on non-phagocytes does not necessarily validate the feasibility of phage display for eat-me signal study in phagocytes. As T7 bacteriophage particle is only ~55 nm in diameter, one question is whether ORF phage display can be used to identify eat-me signals.

To address this issue, it was queried whether a clonal phage displaying a well-characterized eat-me signal is capable of facilitating phage uptake by phagocytes. This mechanism-based approach should be more relevant than the arbitrary criterion of particle sizes. Two phage clones were constructed displaying full-length MFG-E8 and C-terminus of Gas6 (114D-674P) encoding 2×LG domains for receptor binding. Their cell-binding activities and internalization in phagocytes (J774 for macrophage, BV-2 for microglia and ARPE19 for RPE cells) and non-phagocytes (Neuro-2a and HeLa) were analyzed. The results showed that both phage clones bound to phagocytes and non-phagocytes, but were significantly internalized only in phagocytes. When mixed and diluted with other phages, both MFG-E8-phage and Gas6-phage were substantially enriched by multiple rounds of phagocytosis selection, indicating that phage display can be used to enrich and identify eat-me signals. This feasibility was further substantiated by the identification of Axl-binding proteins of Gas6 and Spryd3 (Table 6).

Figure 14B:
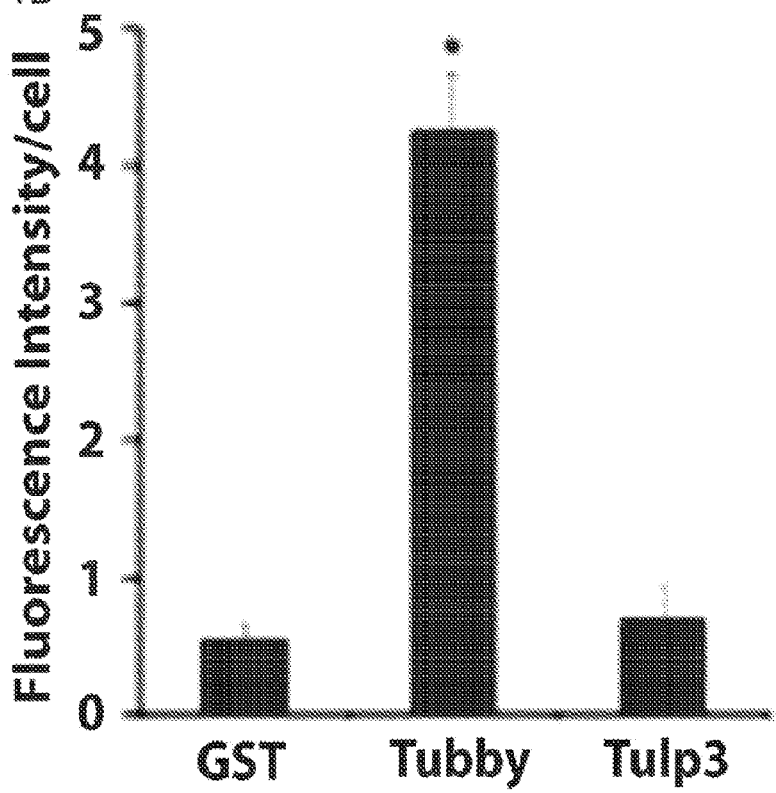
Figure 18:
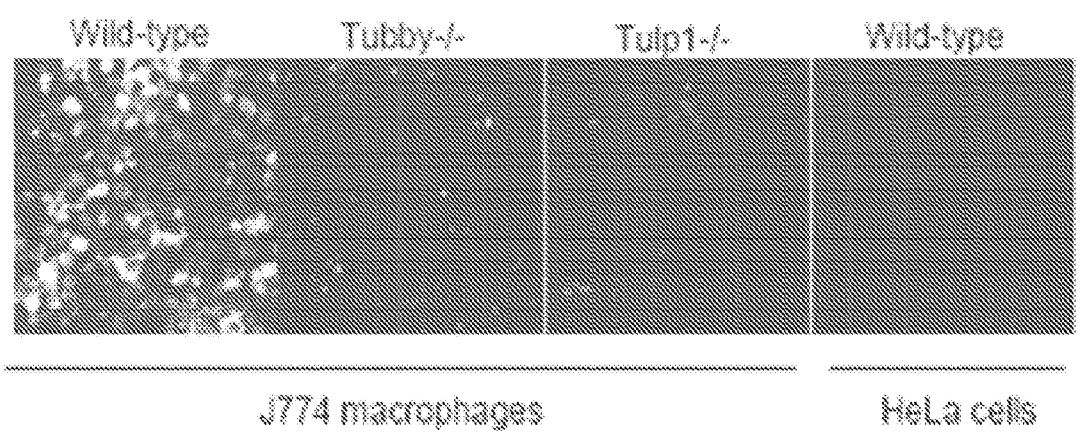
FIG. 18 is a scan of a photograph showing that Tubby and Tulp1 stimulate macrophage phagocytosis. Membrane vesicles were prepared from the retinas of wild-type, tubby$^{-/-}$ or Tulp1$^{-/-}$ mice at postnatal day 19. The membrane vesicles were labeled with CFSE. Macrophage phagocytosis was analyzed in J774 macrophage cell line as described in FIG. 8F by confocal microscopy. HeLa cells were included as a negative control.

False Positives and Negatives:

Putative eat-me signals identified by ORF phage display should be extensively validated and characterized for their biological relevance. They can be analyzed for their stimulation of phagocytosis by other means, including phagocytosis of fluorescent microbeads (diameter in microns rather than in nanometers) covalently conjugated with purified eat-me signals (FIGS. 14A, 14B) or phagocytosis of membrane vesicles or apoptotic cells expressing the putative eat-me signals (FIG. 8D). They should be specifically active in phagocytes, but not in non-phagocytes (FIG. 13A and FIG. 18). Identification of their phagocytic receptors expressed on phagocytes will help verify their functional role in phagocytosis (FIGS. 11A-C). Eat-me signals should have physiological or pathological access to the receptors (FIG. 11D and FIG. 17). For example, these studies revealed that several putative eat-me signals were expressed intracellularly in healthy cells, but released into extracellular space within a few hours of apoptosis, implicating that they may play a role in the removal of apoptotic cells. Apoptotic cells or membrane vesicles derived from mice deficient of eat-me signals may have reduced capacity to induce phagocytosis (FIG. 8F).

Tubby and Tulp1 are Eat-Me Signals for Macrophages:

The presence of tubby in the serum raises an interesting question about its possible role in other phagocytes. The results showed that membrane vesicles deficient in either tubby or Tulp1 have significantly reduced macrophage phagocytosis (FIG. 18), indicating that tubby and Tulp1 are capable of facilitating macrophage phagocytosis. As a negative control, HeLa cells showed minimal uptake of fluorescence-labeled membrane vesicles prepared from wild-type mice. These data indicate that circulating tubby likely plays a role in macrophage phagocytosis.

Example 4

Feasibility of Identification of Eat-Me Signals by Phage Display

Removal of apoptotic cells and cellular debris by phagocytosis is essential for development, tissue homeostasis and resolution of inflammation. Eat-me signals control the initiation of phagocytosis, holding a key to our understanding of phagocyte biology. Due to lack of functional cloning strategy, eat-me signals are conventionally identified and characterized on a case-by-case basis. To investigate the feasibility of functionally cloning eat-me signals by phage display, the biological behavior of T7 phages displaying two eat-me signals: growth arrest-specific gene 6 (Gas6) and milk fat globule-EGF8 (MFG-E8), was characterized.

Gas6-phage binds to all three known Gas6 receptors, Mer, Axl and Tyro3 receptor tyrosine kinases. Gas6-phage and MFG-E8-phage are capable of binding to phagocytes and nonphagocytes. However, both phages stimulate phage uptake only in phagocytes, including macrophages, microglia and retinal pigment epithelium (RPE) cells, but not in non-phagocytes. Furthermore, functional phage selection by phagocytosis in phagocytes enriches both Gas6-phage and MFG-E8-phage, evidencing that phage display can be used as a tool to functionally identify unknown eat-me signals from phage display cDNA library.

Materials and Methods

Materials:

T7Select10-3b vector and T7Select phage packaging kit were purchased from Novagen (Madison, Wis.). All cell culture media and supplements were from Invitrogen (Carlsbad, Calif.). Fetal bovine serum (FBS) was from Hyclone (Logan, Utah). All the restriction enzymes were from New England Biolab (Ipswich, Mass.). Mer-Fc, Axl-Fc and Tyro3-Fc (Dtk-Fc) were from R&D Systems (Minneapolis, Minn.). All other reagents were from Sigma (St. Louis, Mo.). J774, ARPE19, Neuro-2a and HeLa cells were obtained from ATCC (Manassa, Va.).

Cell Culture:

J774, BV-2, Neuro-2a and HeLa cells were cultured in Dulbecco's modified essential medium (DMEM) supplemented with 10% FBS and 2 mM L-glutamine. ARPE19 cells were cultured in DMEM/F-12 (1:1) medium supplemented with 10% FBS, 2 mM L-glutamine and 0.32% sodium bicarbonate.

T7 Phage Display Vector:

T7Select10-3b vector was engineered as the following by attaching a C-terminal biotinylation tag to displayed proteins.

Figures 19A, 19B:
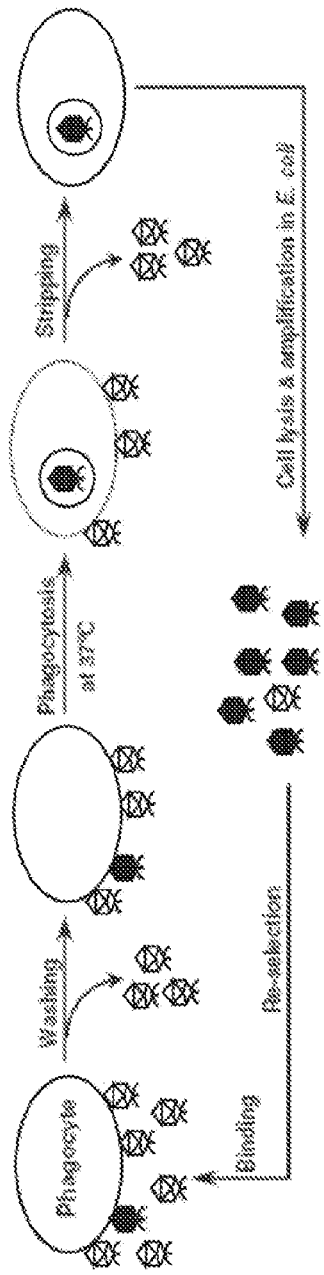
FIG. 19A shows the sequence of the T7Bio phage vector (SEQ ID NO: 46). The sequence fused to the C-terminus of capsid 10B was BamHI and NotI sites, followed by stop codon, XhoI site, a flexible linker and a biotinylation tag.
FIG. 19B is a schematic representation showing phagocytosis selection. Phages were incubated with phagocytes at 4° C. for 30 min without phagocytosis. After washing, the cells were incubated at 37° C. for 30 min to allow phagocytosis of bound phages to occur. Unphagocytosed surface-bound phages were stripped off. Phagocytosed phages were released by cell lysis, amplified in BLT5615 bacteria and used as input for the next round of selection. A aliquot of released phages can also be quantified by plaque assay to determine total phagocytosed phages at each round.

The linker sequence of 5'-GCGGATCCGCGGCCGCTA TAA CTCGAGGGTAGTGGGAGCGGA TTA AAT GAT ATA TTT GAG GCA CAA AAA ATT GAA TGG CAT TAA GAATTCAAGCTTGTCGACAA-3' (SEQ ID NO: 30) (underlined sequences for BamHI, NoI, XhoI and SalI cutting sites, italic sequence for the biotinylation tag, bolded codon for internal stop codons) was generated by PCR using overlapping primers, digested with BamHI and SalI, ligated into T7Select10-3b vector at BamHI and XhoI sites to generate T7Bio phage vector (FIG. 19A). Control Biotin-phage expressing biotinylation tag was constructed by replacing the stop codon between NoI and XhoI with a glycine. The engineered phage vector was verified by sequencing.

Gas6-Phage and MFG-E8-Phage:

Full-length mouse Gas6 cDNA sequence was obtained from Open Biosystems (Huntsville, Ala.). The 2×LG receptor binding domains (114D-674P) were amplified by PCR with primers 5'-CA GCGGCCGCTGGACCAGTGCACCCCAAACCCT-3' (SEQ ID NO: 31) and 5'-AC CTCGAGGGGGGTGGCATGCTCCACAG-3' (SEQ ID NO: 32). The PCR product was digested with NotI and XhoI, ligated into T7Bio vector at the same sites, and packaged using T7 phage packaging kit. Clonal Gas6-phage was isolated from phage plates and verified by DNA sequencing.

Full length cDNA of MFG-E8 long form7 was generated by PCR from mouse eye with primers 5'-CA GCGGCCGCTGATGCAGGTCTCCCGTGTGCTG-3' (SEQ ID NO: 33) and 5'-GT CTCGAGACAGCCCAGCAGCTCCAGGCG-3' (SEQ ID NO: 34). The PCR product was digested with NotI and XhoI, ligated into T7Bio vector at the same sites, and packaged into T7 phage. Clonal MFG-E8-phage was isolated and verified by DNA sequencing.

Phage Binding Assay:

Streptavidin (Pierce, Rockford, Ill.) (10 µg/ml) or mock control was coated in phosphate buffered saline (PBS) on Enzyme-Linked ImmunoSorbent Assay (ELISA) plates with high binding capacity (Corning Life Sciences, Lowell, Mass.) at 4° C. overnight, blocked for 1 h with 1% bovine serum albumin (BSA). Gas6-phage, MFG-E8 or T7Bio phage was amplified in BLT5615 cells until lysis. The debris was removed by centrifugation at 13,000×g for 4 min. The phage lysates [100 µl/well, ~1×10$^{11}$ plaque forming unit (pfu)/ml] were incubated with immobilized streptavidin in the presence of 0.2% of Tween-20 for 1 h, followed by washing with PBS containing 0.2% Tween-20 (PBST) for 5 min×6 times. The bound phages were eluted with 1% sodium dodecyl sulfate (SDS) for 10 min, and quantified by plaque assay.

For receptor binding assay, Mer-Fc, Axl-Fc and Tyro3-Fc (the receptor extracellular domains fused to human IgG1 Fc fragment) were coated at 5 µg/ml on ELISA plates. The phage binding was carried out as described above.

Phage Binding to Cells:

Phage lysates (0.5 ml, ~1×10$^{11}$ pfu/ml) were mixed with 1/10 volume of 5 M NaCl, and centrifuged at 13,000×g for 10 min. The supernatants were mixed with 1/6 volume of 50% polyethylene glycol (PEG)-8000, incubated on ice for 30 min and spun at 16,100×g for 20 min at 4° C. The precipitated phages were resuspended in ice-cold complete media (0.5 ml/sample), added to the pre-chilled indicated cells at 60-80% confluency in 12-well plates, incubated at 4° C. with gentle shaking for 30 min. The cells were washed with ice-cold PBS containing 1% FBS (PBS-FBS) for 10 min×5 times. After washing, cells were solubilized with 0.5% Triton X-100 in PBS, and the bound phages were quantified by plaque assay. Total bound phages are expressed as binding index, which is normalized against control Biotin-phage; namely, binding index=(total bound clonal phage)/(total bound Biotin-phage).

Phage Phagocytosis:

All phages were precipitated from phage lysates (0.5 ml, ~1×10$^{11}$ pfu/ml) as described above. Precipitated phages were incubated with indicated cells for 30 min at 4° C. without phagocytosis. After removal of unbound phages by washing with ice-cold PBS, phage-cell complexes were incubated at 37° C. in the complete medium for 30 min to allow phagocytosis to occur. Unphagocytosed surface-bound phages were stripped off by incubating the cells in the stripping buffer (100 mM glycine, pH 2.5, 150 mM NaCl, 200 mM urea, 2 mg/ml polyvinylpyrrolidone) for 2 min×2 times at room temperature, followed by a quick wash with ice-cold PBS. Internalized phages were released by lysing the cells with the lysis buffer (1 mM triethylamine with 0.5% Triton X-100) for 1 min and immediately neutralized to pH 7.4 with 10×PBS pre-mixed with diluted HCl. Since T7 bacteriophage is susceptible to acid and alkaline, it was critical to immediately neutralize the pH to 7.4. The released phages were quantified by plaque assay. Total phagocytosed phages are expressed as phagocytosis index, which is normalized against control Biotin-phage; namely, phagocytosis index=(total phagocytosed clonal phage)/(total phagocytosed Biotin-phage).

To determine the stripping efficiency, the mixture of Gas6-phage and MFG-E8-phage (1:1) was incubated with ARPE19 cells at 4° C. without phagocytosis. After washing, the cells before or after stripping were solubilized with 0.5% Triton X-100 in PBS. Total bound phages were quantified by plaque assay and compared to total phagocytosed phages, which were quantified in experiments performed in parallel as described above.

Immunostaining of Phagocytosed Phages:

ARPE19 cells with phagocytosed phages were fixed with 10% buffered formalin for 30 min, permeabilized with 0.2% Triton X-100 in PBS for 10 min, labeled with streptavidin-conjugated fluorescein isothiocyanate (FITC) to detect biotinylated Gas6-phage, MFG-E8-phage or control Biotin-phage. Nuclei were stained with 1% 4',6-diamidino-2-phenylindole (DAPI). The intracellular fluorescence signals were analyzed by Leica (Bannockburn, Ill.) TCS SP5 confocal microscopy with diode laser for excitation at 405 nm and emission at 480 nm for DAPI, and argon laser excitation at 488 and emission at 510-570 nm for FITC. The percentage of FITC-positive cells was determined with at least 180 cells analyzed for each group.

Phage Enrichment by Phagocytosis:

The principle of phage phagocytosis selection is depicted in FIG. 19B. Gas6-phage or MFG-E8 phage was diluted with control Biotin-phage at a pfu ratio of 1:1,000,000. The mixed phages (2.5 ml, ~1×10$^{11}$ pfu/ml) were precipitated, resuspended in the complete medium, incubated with ARPE19 or J774 in 60-mm culture dishes for 30 min at 4° C., followed by phagocytosis at 37° C. as described above. After stripping off unphagocytosed surface-bound phages, phagocytosed phages were released by cell lysis, amplified in BLT5615 *E. coli*, and used as inputs for the next round of selection. A total of five rounds of selection were performed. Total phagocytosed phages at each round were quantified by plaque assay. Phage lysates at each round were monitored for the enrichment of Gas6-phage or MFG-E8-phage by PCR using following gene specific primers: T7SelectUp (5'-CCA AGC GGA CCA GAT TAT CG-3"; SEQ ID NO: 26) and Gas6-R (5'-TCCCACTCCTGCCCGCCTGT-3'; SEQ ID NO: 35) primers for Gas6-phage; and T7SelectUp and MFGE8-R (5'-GGGTGGGGACGGCAGTATTG-3'; SEQ ID NO: 36) primers for MFG-E8-phage. Phage lysates (1 µl per sample) were used in 20 µl of total PCR reaction mixture to detect the ligand-expressing phages with 30-cycle amplification. The PCR products were analyzed with 1% agarose gel.

Data Analysis:

All experiments were repeated independently for five times. Data are expressed as mean±s.d. Student's t-test is used to analyze statistical significance.

Results

Figure 20A:
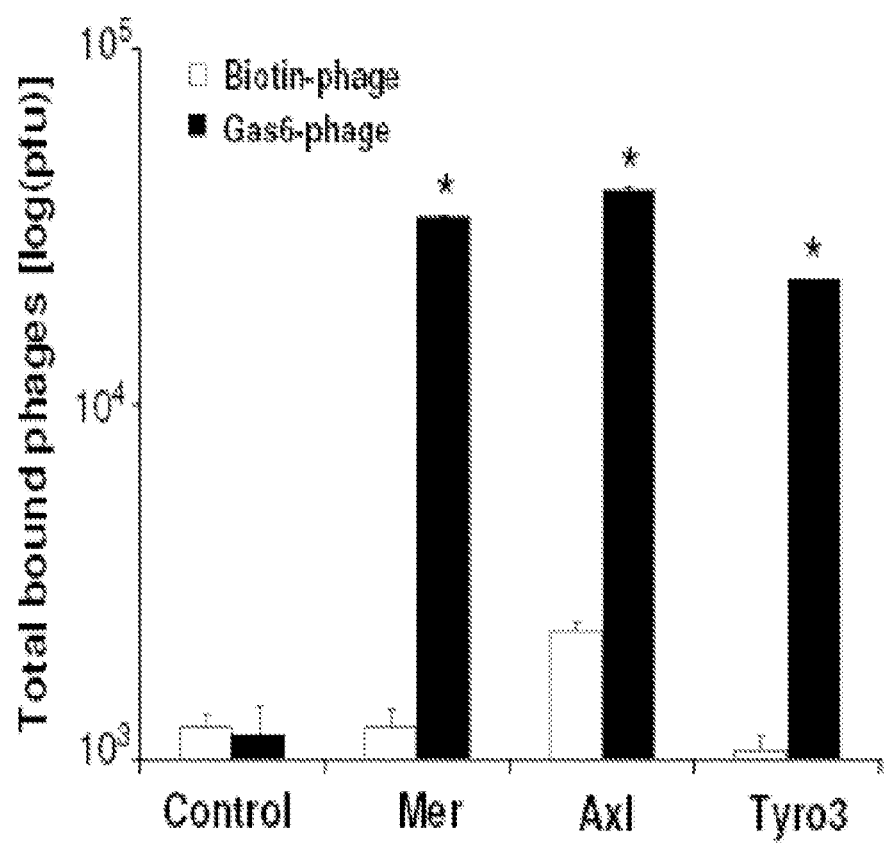
FIGS. 20A and B are graphs showing phage binding to immobilized streptavidin and receptors.

Characterization of Phage Binding Activity:

Both Gas6-phage and MFG-E8-phage expressed an additional C-terminal biotinylation tag, which was spontaneously biotinylated by *E. coli* BirA ligase. To validate the expression of the proteins on phage surface, both phages were analyzed for their binding activity to immobilized streptavidin. The results showed that Gas6-phage and MFG-E8-phage had significant higher binding activity to streptavidin than T7Bio phage (FIG. 20A), which had an internal stop codon to prevent the tag expression. These results indicate that the biotinylated fusion proteins were expressed and displayed on phage surface.

Figure 20B:
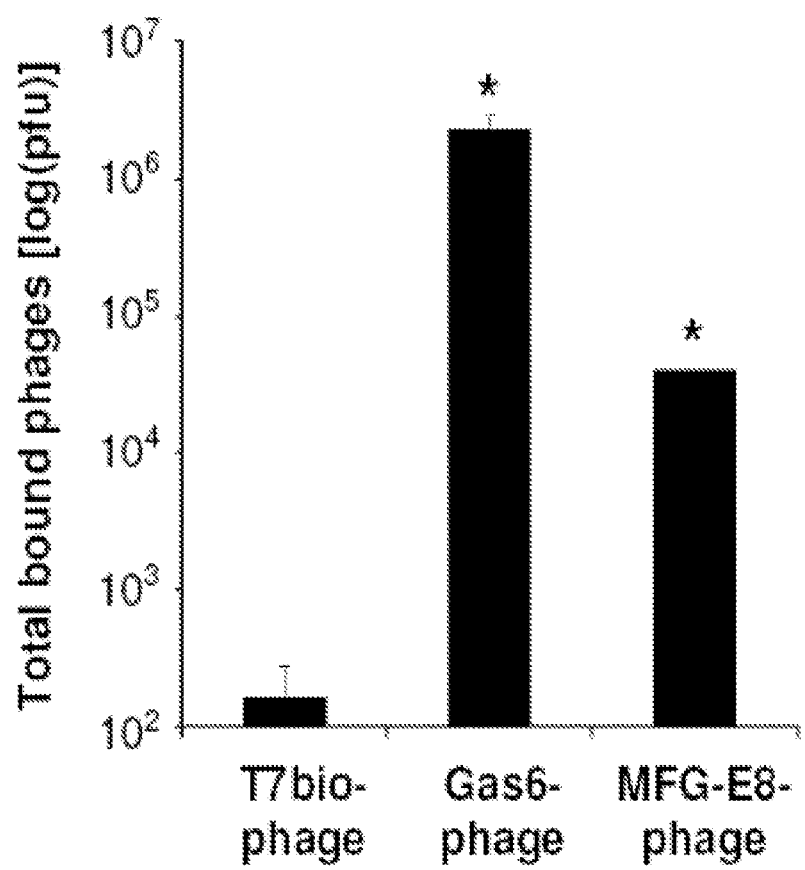
FIG. 20B: Gas6-phage binding to immobilized receptors. Mer-Fc, Axl-Fc and Tyro3-Fc were directly immobilized on 96-well plates. Gas6-phage or control Biotin-phage ($1 \times 10^{10}$ pfu) was incubated with the immobilized receptors or mock control. After washing, bound phages were eluted, and quantified by plaque assay (±s.d., *p<0.001, vs. Biotin-phage, n=5).

Gas6 is one of the well-characterized ligands specifically binding to Mer, Axl and Tyro3 through its C-terminal 2×LG domains. Mouse Gas6 has two potential glycosylation sites at position 417 and 488. The glycosylation was confirmed by the increase in molecular mass of the truncated mouse Gas6 (Asp115-Pro673) expressed in mouse myeloma cell line NSo (R&D Systems, Catalog #986-GS). It is unclear whether the glycosylation is necessary for its binding activity to the receptors. Since *E. coli* is deficient in glycosylation machinery, Gas6 displayed on phage surface should not be glycosylated. To investigate receptor binding activity of unglycosylated Gas6, we analyzed Gas6-phage binding to Mer-Fc, Axl-Fc and Tyro3-Fc immobilized on 96-well plates. The results indicated that Gas6-phage bound to immobilized RTKs, but not mock coated plates (FIG. 20B). Gas6-phage binding activities to the receptor were significantly higher than control Biotin-phage. These results evidence that unglycosylated Gas6-phage was fully capable of binding to the receptors.

Figure 21:
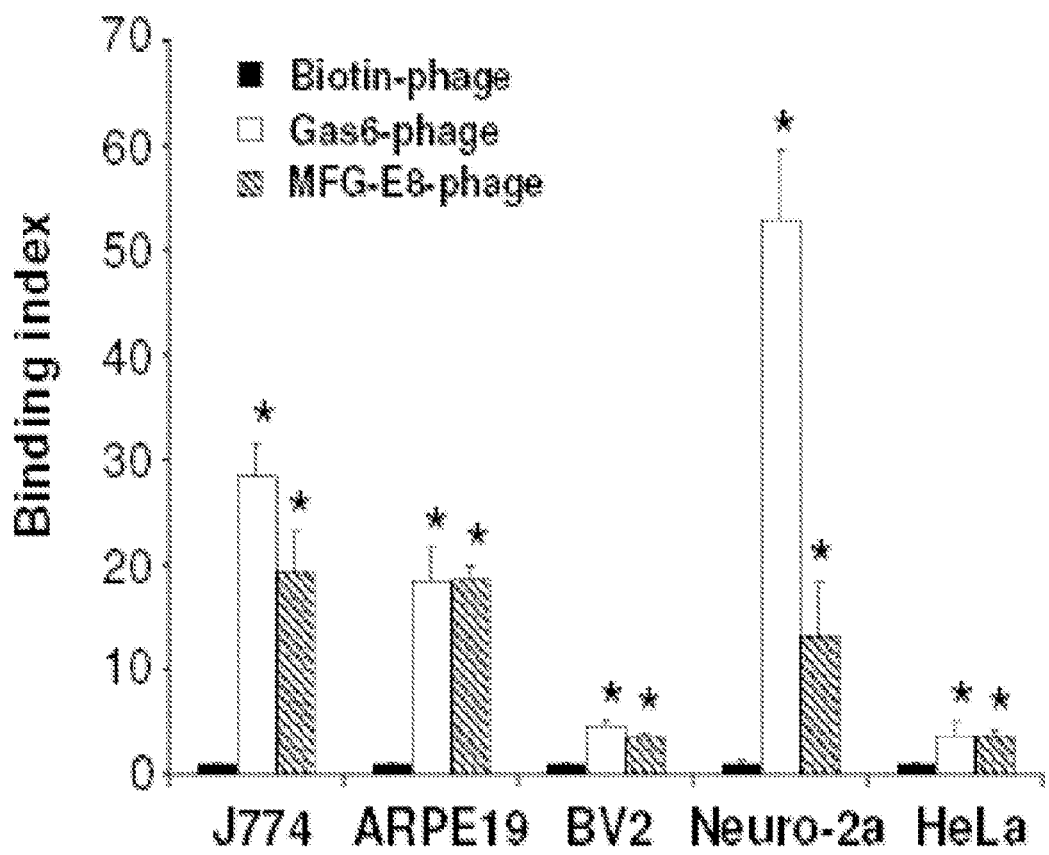
FIG. 21 is a graph showing cell binding activities of Gas6-phage and MFG-E8-phage. Both phages ($5 \times 10^{10}$ pfu) bound to J774, ARPE19, BV-2, Neuro-2a and HeLa cells at 4° C. After washing, bound phages were released by cell lysis with 0.5% Triton X-100 in PBS, and quantified by plaque assay. All the data were normalized to the control Biotin-phage and expressed as binding index (±s.d., *p<0.001, vs. Biotin-phage, n=5).

Binding of Gas6-Phage and MFG-E8-Phage to Phagocytes and Non-Phagocytes:

Gas6-phage and MFG-E8-phage were characterized for their binding to phagocytes and non-phagocytes. J774 is murine macrophage cell line. BV-2 is microglial cell line with phagocytic activity. ARPE19 cell is derived from human RPE cells whose phagocytic activity is important for the regeneration of photoreceptor outer segments (POS). All these three phagocyte cell lines have been used for in vitro phagocytosis studies. HeLa and Neuro-2a are non-phagocytes. To prevent non-specific internalization of bound phages, phage binding was performed at 4° C. Gas6-phage and MFG-E8-phage demonstrated higher binding activity to all cell lines than Biotin-phage (FIG. 21). J774, ARPE19 and Neuro-2a cells showed much higher binding activity to both phages. The highest binding activity of Gas6-phage was to Neuro-2a cells, but not to the phagocytes.

Figure 22A:
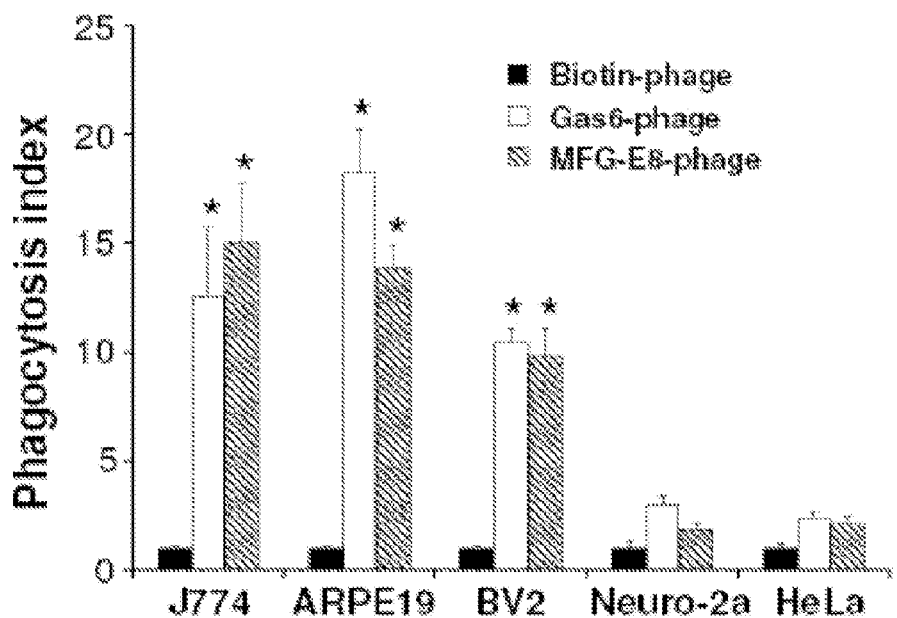
FIG. 22A is a graph showing Gas6-phage and MFG-E8-phage stimulate phagocytosis in phagocytes, but not in non-phagocytes. All phages ($5 \times 10^{10}$ pfu) were precipitated, incubated with the indicated cells, and phagocytosed as described in FIG. 19B. The phagocytosed phages were released by cell lysis and quantified by plaque assay. All the data were normalized to the control Biotin-phage and expressed as phagocytosis index (±s.d., p<0.001, vs. Biotin-phage, n=5).

Gas6 and MFG-E8 Stimulated Phage Uptake by Phagocytes, but not by Non-Phagocytes:

The capacity of Gas6 and MFG-E8 to stimulate phage phagocytosis was analyzed in both phagocytes and non-phagocytes. Gas6-phage and MFG-E8-phage facilitated phagocytosis in J774, BV-2 and ARPE19 cells, but not in HeLa and Neuro-2a cells (FIG. 22A). It is noteworthy that Gas6 minimally facilitated phage internalization in Neuro-2a cells, even though the ligand bound to the cells well (FIG. 21), indicating that phage binding to surface receptor does not always elicit phagocytosis.

Figure 22B:
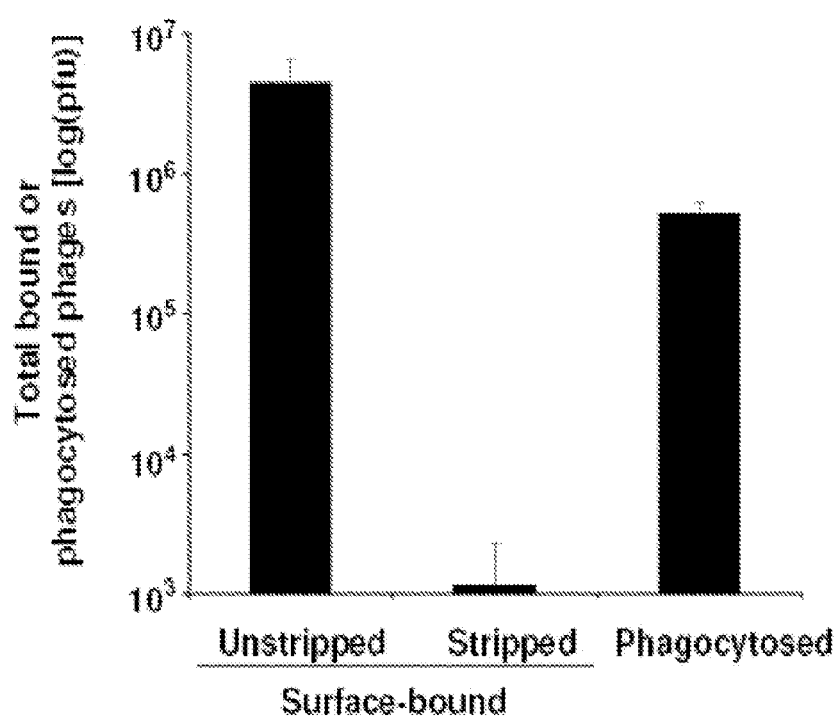
FIG. 22B is a graph showing the stripping efficiency. The mixture of Gas6-phage and MFG-E8-phage (1:1) was incubated with ARPE19 cells at 4° C. without phagocytosis. After washing, the total surface-bound phages were quantified by plaque assay with or without stripping. Phagocytosed mixed phages in ARPE19 cells were quantified in a parallel experiment as described in FIG. 22A.
Figure 23A:
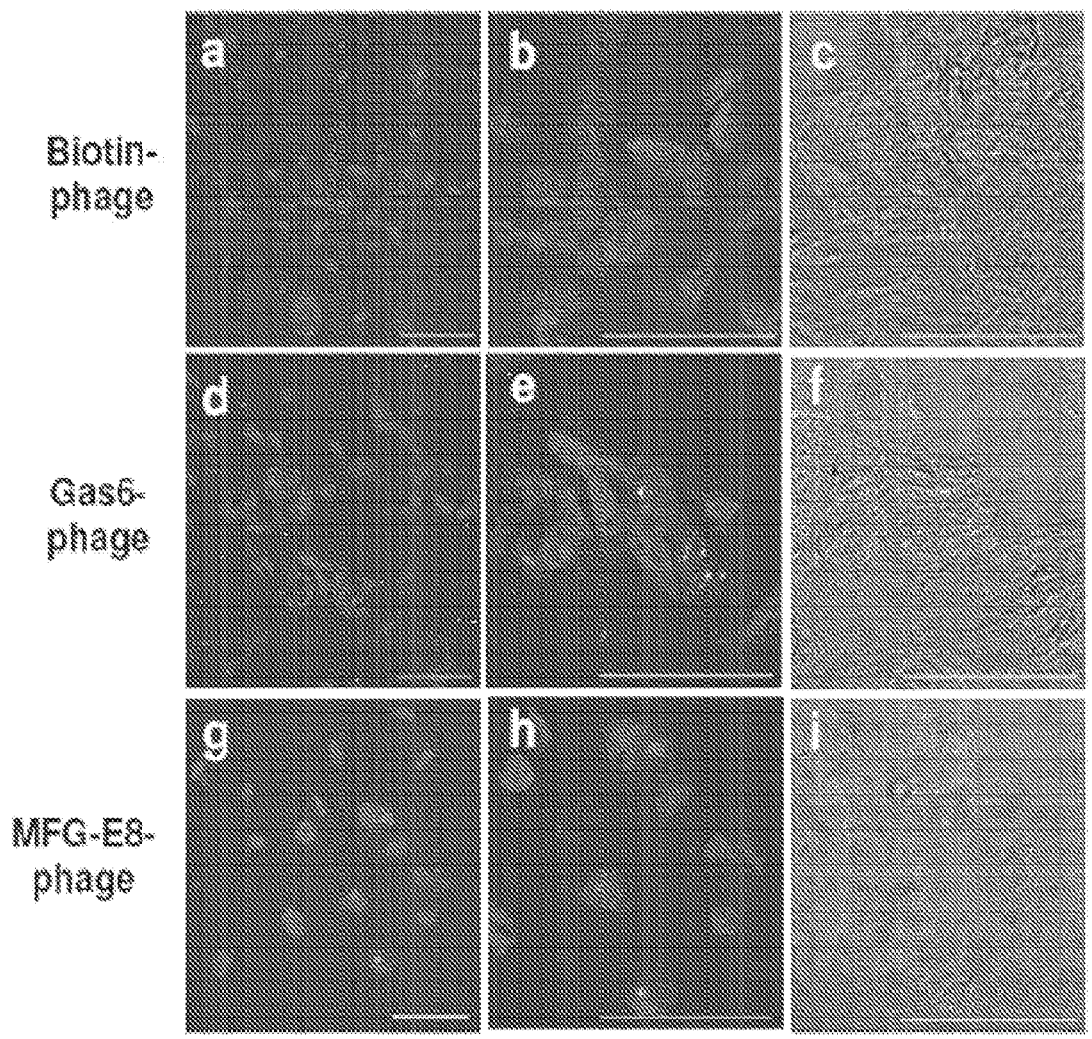
FIG. 23A shows the immunostaining for phagocytosed phages. Phage phagocytosis in ARPE19 was performed as described in FIG. 22A. After phagocytosis, ARPE19 cells were fixed, permeabilized with Triton X-100, labeled with streptavidin-conjugated FITC for the phagocytosed phages, and analyzed by confocal microscopy. Nuclei were stained with DAPI. Panels in the left column (a, d and g) are in lower magnification, while all others are in higher magnification. The indicated size bars are 25 μm.
Figure 23B:
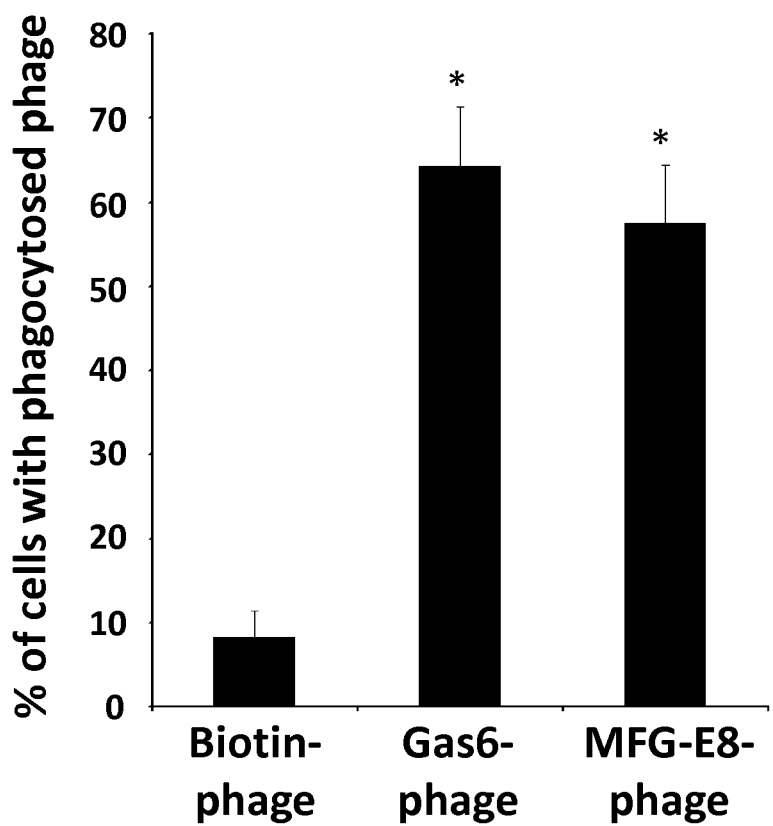
FIG. 23B is a graph showing the percentage of cells with phagocytosed phage. At least 180 cells were analyzed for each group (±s.d., *p<0.001, vs. Biotin-phage, n>180).
Figure 24A:
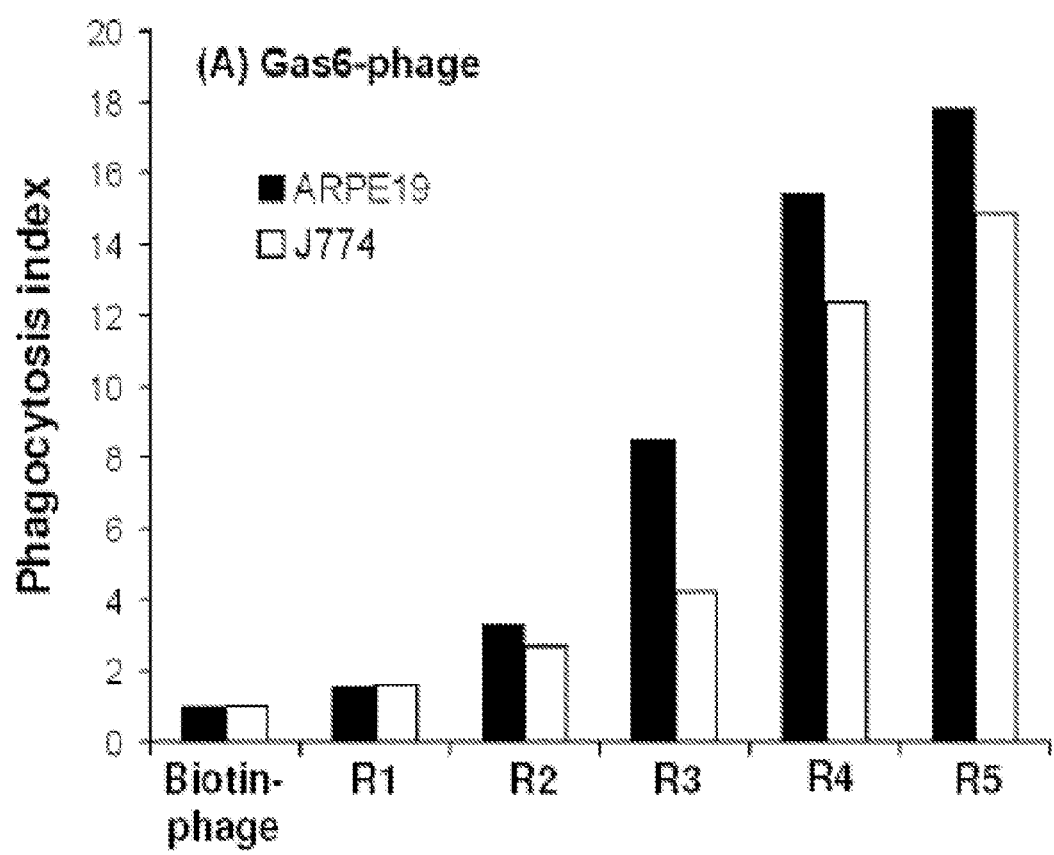
FIGS. 24A to 24C show the enrichment of Gas6-phage and MFG-E8-phage by phagocytosis. Gas6-phage or MFG-E8 phage was diluted with Biotin-phage at a pfu ratio of 1:1,000,000. The diluted phages were precipitated, incubated with ARPE19 or J774, phagocytosed, recovered by cell lysis, amplified in BLT5615, and used as inputs for the next round of selection. A total of five rounds of selection were performed. Total internalized phages for diluted Gas6-phage (FIG. 24A) and MFG-E8-phage (FIG. 24B) were quantified by plaque assay at each round. Biotin-phage was included as a negative control. The data are the representative of five independent experiments.
Figure 24B:
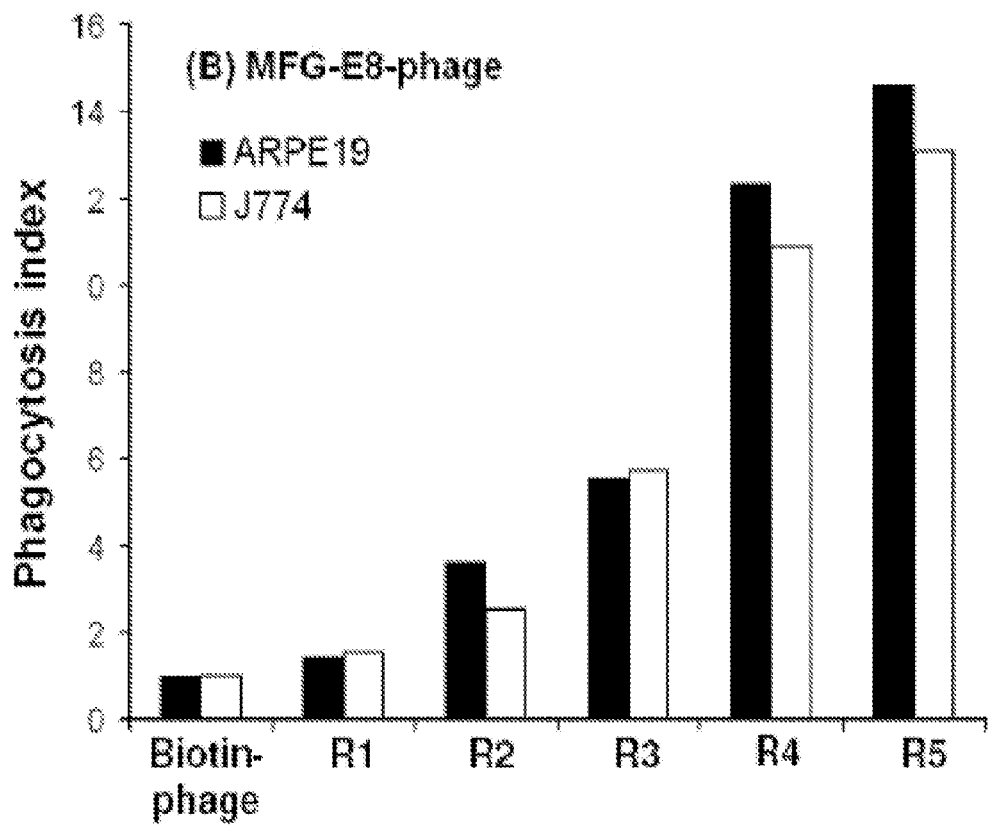
Figure 24C:
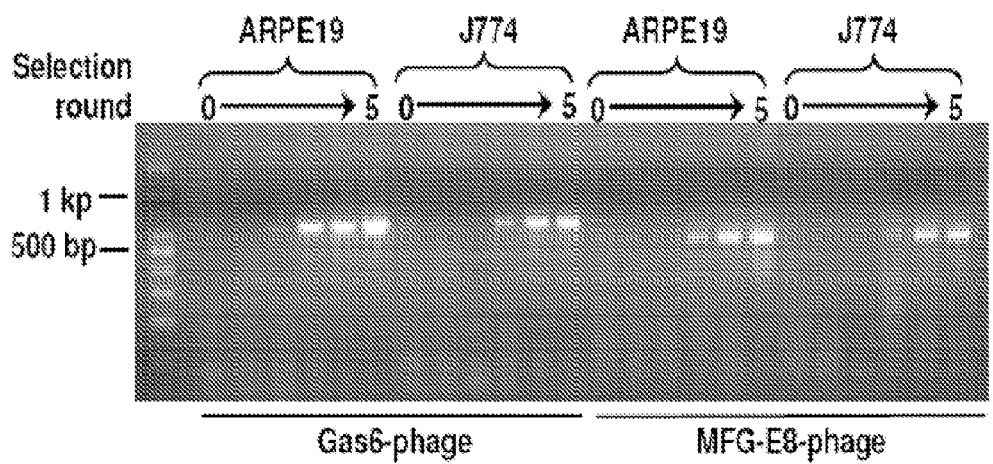

The stripping efficiency was analyzed by comparing the total surface-bound phages before and after stripping without phagocytosis. The results revealed that more than 99.98% of surface-bound phages were stripped off (FIG. 22B), suggesting an excellent stripping efficiency. A parallel experiment revealed that ~11.5% of the total bound phages was phagocytosed.

Since all the phages used in phagocytosis had C-terminal biotinylation tag, internalized phages in ARPE19 cells were conveniently visualized with streptavidin-FITC. Confocal microscopy analysis revealed that Gas6-phage and MFG-E8-phage, but not Biotin-phage, were internalized (FIG. 28A). Compared with 8% of ARPE19 cells with internalized Biotin-phage, 66% and 57% of the cells had intracellular Gas6-phage and MFG-E8-phage (FIG. 28B), respectively. These data suggest that Gas6 and MFG-E8 displayed on phage surface specifically stimulated phage phagocytosis in the phagocytes.

Enrichment of Gas6-Phage and MFG-E8-Phage by Phagocytosis Selection:

The higher internalization capacity of Gas6-phage and MFG-E8-phage evidences that they should be enrichable by multiple rounds of phagocytosis selection. As an illustration, Gas6-phage or MFG-E8 phage were diluted with Biotin-phage at a pfu ratio of 1:1,000,000. Diluted phages were added to J774 cells or ARPE19 cells to analyze the possible enrichment of Gas6-phage and MFG-E8 phage. The total phagocytosed phages were drastically increased at Round 3-5 (FIGS. 29A and B). Enriched phages were analyzed by PCR using gene-specific primers. After 3-5 rounds of phagocytosis selection, Gas6-phage and MFG-E8 phage were detected by PCR, whereas both phages were not detectable in the diluted phage mixture before the selection (FIG. 29C). Additional selections further enriched both phages. These results showed that Gas6-phage and MFG-E8-phage were substantially enriched with multiple rounds of phagocytosis selection in J774 and ARPE19 cells.

Discussion:

Binding of eat-me signals on apoptotic cells to phagocytic receptors on phagocytes triggers signaling cascades in phagocytes and facilitates engulfment and ingestion of apoptotic cells. This process not only leads to the removal of apoptotic cells, but also results in suppression of inflammation and immune tolerance to self-proteins. Despite its importance, eat-me signals on apoptotic cells have received relatively little attention. One of the reasons is that it was, heretofore, a daunting challenge to identify unknown eat-me signals. Limited number of eat-me signals, including PS, Gash, MFG-E8, calreticulin, ICAM3, were identified on a case-by-case basis. The only strategy, prior to this invention, was to functionally clone signaling molecules in phagocytosis was to chemically-induced random genetic mutations in *C. elegans*, coupled with morphological screening for accumulation of unengulfed cell corpse by optics microscopy and cloning of the mutated genes. This approach has yielded a number of genes involved in two independent signaling pathways of the engulfment in *C. elegans*. However, this strategy is technically complicated and time-consuming. More importantly, these approaches were not applicable to other animals, which are not transparent for live screening of accumulated cell corpse by optics microscopy. Unlike mammals, *C. elegans* lacks professional phagocytes. Random genetic mutation is not a feasible approach for functional cloning of eat-me signals for mammalian phagocytes.

Several previous studies identified short peptides and scFvs from phage display random peptide libraries and scFv libraries in different cancer cell lines, however, phage display was not a feasible approach for functional cloning of unknown eat-me signals. Cell internalization or endocytosis is a complicated process and includes both phagocytosis (cell eating) and pinocytosis (cell drinking) (Liu, J. & Shapiro, J. I. Endocytosis and signal transduction: basic science update. *Biol Res Nurs* 5, 117-28 (2003)). In general, phagocytosis arbitrarily refers to internalization of large particles (>200 nm), whereas pinocytosis refers to internalization of smaller particles or cell surface-bound ligands or molecules through different mechanisms. For example, the molecular mechanism of pinocytosis induced by epidermal growth factor (EGF) binding to EGF receptor (EGF-R) on non-phagocytes is very different than those for PS-, Gas6-, or MFG-E8-mediated phagocytosis of apoptotic cells in professional phagocytes. Internalization of EGF-expressing phage by binding to EGF-R on non-phagocytes does not necessarily validate the feasibility of phage display for phagocytosis study in professional phagocytes. In this regard, we characterized the phagocytosis of Gas6- and MFG-E8-expressing phages in professional phagocytes and non-phagocytes. The results indicated that phages expressing eat-me signals can bind to both phagocytes and non-phagocytes. However, only phagocytes can phagocytose phages expressing eat-me signals. These evidence that binding of eat-me signals to their cognate phagocytic receptors does not always trigger phagocytosis. Downstream signaling pathways in phagocytes, including receptor signaling, cytoskeleton protein rearrangement and engulfment, also play roles in the uptake. The data herein, also demonstrated that multiple rounds of phagocytosis selection result in enrichment of phages expressing eat-me signals, opening the opportunity for possible functional cloning of eat-me signals by phage display.

Mammals have developed professional phagocytes to facilitate the removal of apoptotic cells or cellular debris. Besides the well-known macrophages, microglia in the central nerve system (CNS), RPE cells in the retina and Sertoli cells in the testis are the well-characterized specialized phagocytes. Most known eat-me signals were identified and characterized in macrophages. Little is known about eat-me signals in other phagocytes. For example, RPE phagocytosis is important for the maintenance of visual function. Photoreceptor outer segments (POS), which convert light to electrical impulses, are susceptible to photo-oxidation damage. As a part of repair process, photoreceptors shed the damaged POS at the tip of the outer segments in a diurnal rhythm. RPE cells underneath photoreceptors within close contact to the POS play a pivotal role in the POS regeneration by ingesting and recycling shed POS vesicles through phagocytosis. The importance of RPE phagocytosis has been implicated in the retinal degeneration model of RCS rats, whose defect in the removal of shed POS is due to a genetic mutation in Mer receptor tyrosine kinase on RPE cells. To identify unknown eat-me signals in RPE cells, we have recently generated an open-reading-frame (ORF) phage display cDNA library from mouse eye. Phagocytosis selection of the library by phage display resulted in the identification of nine putative eat-me signals, as described in Example #3. Among them was Gas6 (43Q-148R), which substantiates the functional cloning strategy for unbiased discovery of endogenous eat-me signals. Mutations in two novel eat-me signals associated with photoreceptor degeneration with unknown mechanism. The characterization of phage display as a valuable tool to study eat-me signals in this study lay a groundwork for functional cloning of eat-me signals in phagocytosis in various professional phagocytes.

In conclusion, it has been demonstrated in this study that two well-characterized eat-me signals displayed on phage surface can stimulate phagocytosis of the cognate phage by professional phagocytes, leading to the specific enrichment of the phage. These results evidence that phage display is a feasible approach for functional cloning of unknown eat-me signals.

OTHER EMBODIMENTS

It is to be understood that while the invention has been described in conjunction with the detailed description thereof, the foregoing description is intended to illustrate and not limit the scope of the invention. Other aspects, advantages, and modifications are within the scope of the following claims.

All references cited herein, are incorporated herein by reference. Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract will allow the reader to quickly ascertain the nature of the technical disclosure. It is submitted with the understanding that it will not be used to interpret or limit the scope or meaning of the following claims.

What is claimed is:

1. A method of identifying molecular interactions between molecules comprising:
   generating a diverse library of open reading frame (ORF) polynucleotides and ligating the ORF polynucleotides into a T7 phage display vector;
   wherein generating said diverse library of ORF polynucleotides comprises:
   isolating total RNA from a cell;
   generating orientation-directed cDNAs using tagged random primers;
   purifying and ligating the cDNAs into the T7 phage display vector,
   wherein the cDNAs comprise OFR polynucleotides, wherein the OFR polynucleotides ligated into the T7 phage display vector comprises a polynucleotide encoding a T7 capsid 10B fusion protein, wherein the polynucleotide encoding the T7 capsid 10B fusion protein comprises a T7 capsid 10B fused to the N-terminus of an ORF polynucleotide and a tag molecule fused to the C-terminus of the ORF polynucleotide, wherein said T7 capsid 10B tag is expressed on the C-terminus of the T7 capsid 10B fusion protein when the ORF polynucleotide is inserted in-frame;

converting the ligated T7 phage vector into T7 dual display phage by transforming *E. coli* to produce T7 dual display phage, wherein the *E. coli* express a T7 capsid 10A fusion protein, wherein the T7 capsid 10A fusion protein comprises T7 capsid 10A with a C-terminal tag, wherein the T7 dual phage display both the T7 capsid 10A fusion protein and the T7 capsid 10B fusion protein;

selecting the T7 dual display phage comprising expressed open reading frames, wherein the T7 dual display phage display both the T7 10A capsid tag and the T7 10B capsid tag for detection of open reading frame expressing phage, wherein the T7 10A capsid tag is detected by a tag binding partner which specifically binds to the T7 10A capsid tag, wherein the T7 10B capsid tag is detected by a tag binding partner which specifically binds to the T7 10B capsid tag;

screening the T7 dual display phage for binding to a specific ligand, wherein T7 dual display phage containing an open reading frame is specifically enriched by binding to the specific ligand and eluted via enzyme cleavage; and, identifying molecular interactions between the expressed open reading frame and the specific ligand.

2. The method of claim 1, wherein the T7 10B capsid C-terminal tag is selected from the group consisting of a poly histidine tag, poly-histidine-glycine tag, influenza HA tag, Herpes Simplex virus glycoprotein D (gD) tag, c-myc tag, FLAG tag, Strep-tag, biotin tag, V5 tag, S tag, HSV tag, T7 tag, CBD tag and GST tag.

3. The method of claim 1, wherein the T7 10B capsid tag binding partner comprises antibodies, aptamers, oligonucleotides, enzymes, or peptides.

4. The method of claim 3, wherein the T7 10B capsid tag binding partner comprises a detectable moiety comprising: a radioisotope, a metal chelator, an enzyme, as substrate, a cofactor, an inhibitor, a fluorescent compound, a bioluminescent compound, a magnetic particle or a chemiluminescent compound.

5. The method of claim 1, wherein the screening the T7 dual display phage for binding to molecules is a high throughput assay.

* * * * *

SEQUENCE LISTING

```
<160> NUMBER OF SEQ ID NOS: 51

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Gln Lys Leu Ile Ser Glu Glu Asp Leu
1               5                   10

<210> SEQ ID NO 3
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Pro Tyr Asp Val Pro Asp Tyr Ala
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Thr Asp Ile Glu Met Asn Arg Leu Gly Lys
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Pro Glu Leu Ala Pro Glu Asp Pro Glu Asp
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Lys Pro Ile Pro Asn Pro Leu Leu Gly Leu Asp Ser Thr
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Tyr Lys Asp Asp Asp Asp Lys
1               5

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tagcggccgc taatgacttc caagccgcat tc                                    32
```

```
<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agctcgagct cgcaggccag cttgctgtc                                        29

<210> SEQ ID NO 10
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gcggatccgc ggccgctata actcgagggt agtgggagcg gattaaatga tatatttgag      60
gcacaaaaaa ttgaatggca ttaagaattc aagcttgtcg acgc                      104

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgggatccgc ggccgctata actcgagggt agtgggagcg gattaaatg                  49

<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agtgggagcg gattaaatga tatatttgag gcacaaaaaa ttgaatg                    47

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acgtcgacaa gcttgaattc ttaatgccat tcaattttt gtgcctc                     47

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccaaagaatc ggttgttgaa                                                  20
```

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agcaaactac gctgctctga                                                    20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
actgtaagga atccagtcgg a                                                  21

<210> SEQ ID NO 17
<211> LENGTH: 152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
cgggatccgc tggaagtgct gtttcagggc ccgggcagcg gttcaggctc gcggccgcta        60
gatatctaac tcgagggtag tgggagcgga ttaaatgata tatttgaggc acaaaaaatt       120
gaatggcatt aagaattcaa gcttgtcgac gt                                     152

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(20)
<223> OTHER INFORMATION: a, c, t, g, unknown or other

<400> SEQUENCE: 18
gcgccgcgac cnnnnnnnnn                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(20)
<223> OTHER INFORMATION: a, c, t, g, unknown or other

<400> SEQUENCE: 19
ggccggcctc cnnnnnnnnn                                                    20

<210> SEQ ID NO 20
<211> LENGTH: 34

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aactagataa gaatagcggc cgcgcgccgc gacc                                    34

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aactagataa gaatagcggc cgcagcgccg cgacc                                   35

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aactagataa gaatagcggc cgcaagcgcc gcgacc                                  36

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aatgatctcg agggccggcc tcc                                                23

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aatgatctcg agtggccggc ctcc                                               24

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aatgatctcg agtaggccgg cctcc                                              25

<210> SEQ ID NO 26
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 26
ccaagcggac cagattatcg                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gagcgcatat agttcctcct                                              20

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgcggatatc tcggtagtg                                               19

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atgaattctc tagagtcgag gaatactgtt tcctgtgtg                         39

<210> SEQ ID NO 30
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gcggatccgc ggccgctata actcgagggt agtgggagcg gattaaatga tatatttgag   60
gcacaaaaaa ttgaatggca ttaagaattc aagcttgtcg acaa                  104

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cagcggccgc tggaccagtg caccccaaac cct                                33

<210> SEQ ID NO 32
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 32
acctcgaggg gggtggcatg ctccacag                                         28

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cagcggccgc tgatgcaggt ctcccgtgtg ctg                                   33

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtctcgagac agcccagcag ctccaggcg                                        29

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcccactcct gcccgcctgt                                                  20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gggtggggac ggcagtattg                                                  20

<210> SEQ ID NO 37
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(75)
<220> FEATURE:
<221> NAME/KEY: CDS
<222> LOCATION: (79)..(138)

<400> SEQUENCE: 37 gtg atg ctc ggg gat ccg ctg gaa gtg ctg ttt cag ggc ccg ggc agc        48
Val Met Leu Gly Asp Pro Leu Glu Val Leu Phe Gln Gly Pro Gly Ser
1               5                   10                  15
```

```
ggt tca ggc tcg cgg ccg cta gat atc taa ctc gag ggt agt ggg agc      96
Gly Ser Gly Ser Arg Pro Leu Asp Ile     Leu Glu Gly Ser Gly Ser
            20                  25                      30 gga tta aat gat ata ttt gag gca caa aaa att gaa tgg cat            138
Gly Leu Asn Asp Ile Phe Glu Ala Gln Lys Ile Glu Trp His
        35                  40                  45 taagaattca agcttgtcga gtaa                                         162

<210> SEQ ID NO 38
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Met Leu Gly Asp Pro Leu Glu Val Leu Phe Gln Gly Pro Gly Ser
1               5                   10                  15

Gly Ser Gly Ser Arg Pro Leu Asp Ile
            20                  25

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Glu Gly Ser Gly Ser Gly Leu Asn Asp Ile Phe Glu Ala Gln Lys
1               5                   10                  15

Ile Glu Trp His
            20

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Gly Val Lys Lys Lys
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Gly Val Lys Ala Ala
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 42

Lys Gly Lys Gly Lys Lys Lys
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Gly Lys Gly Lys Ala Ala
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Gly Ala Gly Lys Lys Lys
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Gly Ala Gly Ala Lys Lys
1               5

<210> SEQ ID NO 46
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(27)
<220> FEATURE:
<221> NAME/KEY: CDS
<222> LOCATION: (31)..(90)

<400> SEQUENCE: 46 gtg atg ctc ggg gat ccg cgg ccg cta taa ctc gag ggt agt ggg agc      48
Val Met Leu Gly Asp Pro Arg Pro Leu     Leu Glu Gly Ser Gly Ser
1               5                       10              15 gga tta aat gat ata ttt gag gca caa aaa att gaa tgg cat              90
Gly Leu Asn Asp Ile Phe Glu Ala Gln Lys Ile Glu Trp His
             20                  25 taagaattca agcttgtcga g                                             111

<210> SEQ ID NO 47
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 47

Val Met Leu Gly Asp Pro Arg Pro Leu
1               5

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Glu Gly Ser Gly Ser Gly Leu Asn Asp Ile Phe Glu Ala Gln Lys
1               5                   10                  15

Ile Glu Trp His
            20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggagctgtcg tattccagtc                                              20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aacccctcaa gacccgttta                                              20

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 51

His His His His His His His His
1               5
```